(12) United States Patent
Hewawasam et al.

(10) Patent No.: US 7,601,686 B2
(45) Date of Patent: Oct. 13, 2009

(54) HEPATITIS C VIRUS INHIBITORS

(75) Inventors: Piyasena Hewawasam, Middletown, CT (US); Min Ding, Glastonbury, CT (US); Li-Qiang Sun, Glastonbury, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/481,536

(22) Filed: Jul. 6, 2006

(65) Prior Publication Data

US 2007/0010455 A1 Jan. 11, 2007

Related U.S. Application Data

(60) Provisional application No. 60/698,172, filed on Jul. 11, 2005.

(51) Int. Cl.
*A61K 38/00* (2006.01)
(52) U.S. Cl. .......................................................... 514/2
(58) Field of Classification Search ........................ None
See application file for complete search history.

(56) References Cited

U.S. PATENT DOCUMENTS

| 2005/0153877 A1 | 7/2005 | Miao et al. |
| 2006/0172950 A1 | 8/2006 | Wang et al. |
| 2006/0199773 A1 | 9/2006 | Sausker et al. |

FOREIGN PATENT DOCUMENTS

| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/060926 | 8/2002 |
| WO | WO 03/053349 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | * 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | * 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |

OTHER PUBLICATIONS

U.S. Appl. No. 11/591,253, filed Nov. 1, 2006, D'Andrea, et al.
U.S. Appl. No. 11/415,722, filed May 2, 2006, Wenying Li.
U.S. Appl. No. 11/546,505, filed Oct. 11, 2006, Carini, et al.
Lauer, G.M. and Walker, B.D., "Hepatitis C Virus Infection", *N. Engl. J. Med.*, 2001, 345, 41-52.
Poupart, M.-A., Cameron, D.R., Chabot, C., Ghiro, E., Goudreau, N., Boulet, S., Poirier, M., and Tsantrizos, Y.S., "Solid-Phase Synthesis of Peptidomimetic Inhibitors for the Hepatitis C Virus NS3 Protease", *J. Org. Chem.*, 2001, 66, 4743-4751.

* cited by examiner

*Primary Examiner*—Cecilia Tsang
*Assistant Examiner*—Thomas S Heard
(74) *Attorney, Agent, or Firm*—Pamela A. Mingo

(57) ABSTRACT

The present disclosure relates to tripeptide compounds, compositions and methods for the treatment of hepatitis C virus (HCV) infection. Also disclosed are pharmaceutical compositions containing such compounds and methods for using these compounds in the treatment of HCV infection.

23 Claims, No Drawings

HEPATITIS C VIRUS INHIBITORS

CROSS REFERENCE TO RELATED APPLICATION

This application claims priority from U.S. Provisional Application Ser. No. 60/698,172, filed Jul. 11, 2005.

The present disclosure is generally directed to antiviral compounds, and more specifically directed to compounds which inhibit the functioning of the NS3 protease (also referred to herein as "serine protease") encoded by Hepatitis C virus (HCV), compositions comprising such compounds and methods for inhibiting the functioning of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to cleave at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with another compound having anti-HCV activity, e.g., a compound which is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a first aspect of the present disclosure is provided a compound of Formula (I)

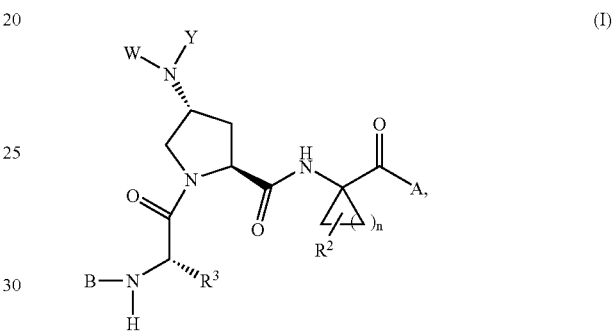

(I)

or an enantiomer, diastereoisomer, or a pharmaceutically acceptable salt thereof, wherein A is alkoxy, hydroxy, —N(H)SO$_m$R$^1$, or

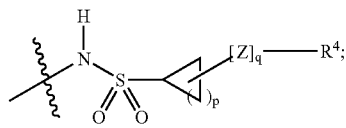

m is 1 or 2;
p is 1, 2 or 3;
q is 0 or 1;
R$^1$ is alkyl, aryl, cycloalkyl, (cycloalkyl)alkyl, heterocyclyl, or —NR$^7$R$^8$;
R$^4$ is alkyl, aryl, arylalkyl, cycloalkenyl, cycloalkyl, halo, heterocyclyl, or trialkylsilyl; wherein the alkyl is optionally substituted with alkenyl, alkoxy, alkynyl, aryl, arylalkyl, aryloxy, cycloalkenyl, cycloalkyl, halo, heterocyclyl, or hydroxy; provided that when R$^4$ is halo or trialkylsilyl then q is 0;
R$^7$ and R$^8$ are each independently alkoxy, alkyl, aryl, arylalkyl, cycloalkyl, (cycloalkyl)alkyl, haloalkyl, heteroaryl, or heteroarylalkyl;
Z is

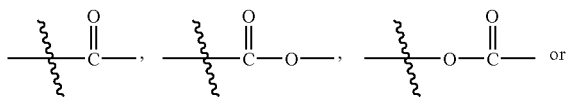

or

-continued

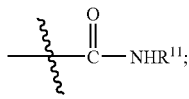

wherein each group is drawn with its left end attached to the cycloalkyl ring and its right end attached to R⁴

R¹¹ is hydrogen, alkenyl, alkyl, or aryl, each optionally substituted with alkoxy, amido, amino, cyano, halo, nitro, or phenyl;

n is 1 or 2;

R² is hydrogen, alkenyl, alkyl, or cycloalkyl, each optionally substituted with one to three halo groups;

W is hydrogen, alkyl, or alkylcarbonyl; wherein the alkyl can be optionally substituted with alkoxy, amino, carboxy, cyano, or halo;

Y is —C(=O)R⁹, —C(=O)OR⁹, —C(O)N(R¹⁰)R⁹, —C(=S)N(R¹⁰)R⁹, —C(NH)N(R¹⁰)R⁹, —S(O)₂R⁹, —S(O)₂ N(R¹⁰)R⁹, arylalkyl, heterocyclyl, or heterocyclylalkyl; provided that when W is hydrogen, Y is other than aryl, arylalkyl, or heterocyclyl;

R⁹ and R¹⁰ are independently hydrogen, alkyl, aryl, arylalkyl, heterocyclyl, or heterocyclylalkyl, wherein the alkyl is optionally substituted with alkoxy, amino, cyano, carboxy, or halo; or R⁹ and R¹⁰, together with the nitrogen atom to which they are attached, form a three- to seven-membered ring optionally containing zero to two additional heteroatoms selected from nitrogen, oxygen, and sulfur;

R³ is hydrogen, alkenyl, alkoxy, alkyl, alkylamino, alkylsulfanylalkyl, alkylsulfinylalkyl, alkylsulfonylalkyl, alkynyl, aryl, arylalkyl, carboxyalkyl, cyanoalkyl, cycloalkenyl, cycloalkenylalkyl, cycloalkyl, (cycloalkyl)alkyl, haloalkyl, heterocyclylalkyl, or hydroxyalkyl, wherein the cycloalkyl and cycloalkyl part of the (cycloalkyl)alkyl can be optionally substituted with alkenyl, alkoxy, alkyl, alkylaminoalkyl, or hydroxy;

B is hydrogen, alkyl, aryl, heteroaryl, heterocyclyl, R⁵—(C=O)—, R⁵(C=O)—, R⁵—N(R⁶)—C(=O)—, R⁵—N(R⁶)—C(=S)—, R⁵SO₂—, or R⁵—N(R⁶)—SO₂—;

R⁵ is
(i) alkyl optionally substituted with alkoxy, alkylamino, alkylcarbonyl, amido, (lower alkyl)amido, amino, carboxy, dialkylamino, formyl, one to three halo groups, hydroxy, OC(=O)alkyl, phenyl, or phenyloxy, wherein the phenyloxy is optionally substituted with halo or alkoxy;
(ii) cycloalkyl or (cycloalkyl)alkyl, wherein the cycloalkyl and the cycloalkyl part of the (cycloalkyl)alkyl can be optionally substituted with alkoxycarbonyl, alkylamino, amido, (lower alkyl)amido, amino, carboxy, dialkylamino, or hydroxy;
(iii) aryl, arylalkyl, heteroaryl, or heteroarylalkyl, all optionally substituted with alkyl, amido, (lower alkyl) amido, alkylamino, amino, dialkylamino, halo, hydroxy, or nitro;
(iv) heterocyclyl or heterocyclylalkyl, wherein the heterocyclyl and the heterocyclyl part of the heterocyclylalkyl are optionally substituted with alkyl, alkylamino, amido, (lower alkyl)amido, amino, dialkylamino, or hydroxy;
(v) bicyclo(1.1.1)pentane; or
(vi) —C(=O)Oalkyl, alkenyl, or alkynyl; and R⁶ is hydrogen or alkyl optionally substituted with one to three halo groups.

In a first embodiment of the first aspect of the present disclosure is provided a compound of Formula (I) wherein A is alkoxy, hydroxy, or —N(H)SO$_m$R¹;

m is 2;

R¹ is alkyl, aryl, cycloalkyl, (cycloalkyl)alkyl, or heterocyclyl;

n is 1;

R² is alkenyl, alkyl, or cycloalkyl, each optionally substituted with one to three halo groups;

W is hydrogen or alkyl;

Y is —C(=O)R⁹, —C(=O)OR⁹, —C(O)N(R¹⁰)R⁹, —C(=S)N(R¹⁰)R⁹, —S(O)₂R⁹;

R⁹ and R¹⁰ are independently hydrogen, alkyl, aryl, arylalkyl, heterocyclyl, or heterocyclylalkyl;

R³ is alkenyl, alkoxy, or alkyl;

B is hydrogen, alkyl, R⁵—(C=O)—, R⁵(C=O)—, or R⁵—N(R⁶)—C(=O)—;

R⁵ is (cycloalkyl)alkyl or alkyl, wherein the alkyl is optionally substituted with alkoxy, alkylamino, amino, carboxy, dialkylamino, one to three halo groups, hydroxy, or phenyl; and R⁶ is hydrogen.

In a second aspect of the present disclosure is provided a compound of Formula (II)

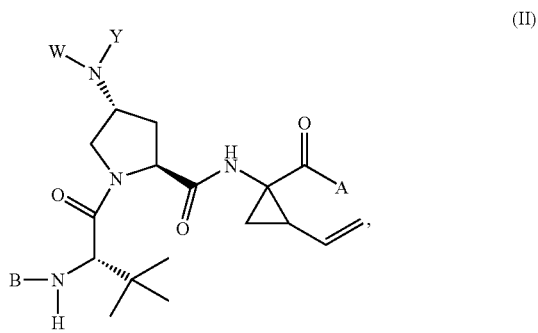

or an enantiomer, diastereomer, or pharmaceutically acceptable salt theref, wherein A is hydroxy, or —N(H)SO₂R¹;

R¹ is cycloalkyl;

W is hydrogen or alkyl;

Y is —C(=O)R⁹, —C(=O)OR⁹, —C(O)N(R¹⁰)R⁹, —C(=S)N(R¹⁰)R⁹, —S(O)₂R⁹;

R⁹ and R¹⁰ are independently hydrogen, aryl, arylalkyl, heterocyclyl, or heterocyclylalkyl;

B is R⁵—(C=O)—, or R⁵O(C=O)—; and

R⁵ is (cycloalkyl)alkyl or alkyl.

In a third aspect of the present disclosure is provided a compound of Formula (III)

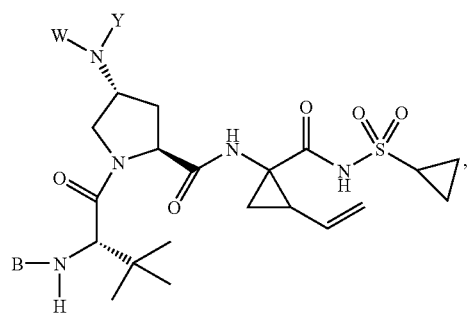
(III)

or an enantiomer, diastereomer, or pharmaceutically acceptable salt theref, wherein W is hydrogen or alkyl;

Y is —C(=O)R$^9$, —C(=O)OR$^9$, —C(O)N(R$^{10}$)R$^9$, —C(=S)N(R$^{10}$)R$^9$, —S(O)$_2$R$^9$;

R$^9$ and R$^{10}$ are independently hydrogen, aryl, arylalkyl, heterocyclyl, or heterocyclylalkyl;

B is R$^5$—(C=O)—; and

R$^5$ is (cycloalkyl)alkyl.

In a fourth aspect of the present disclosure is provided a compound which is

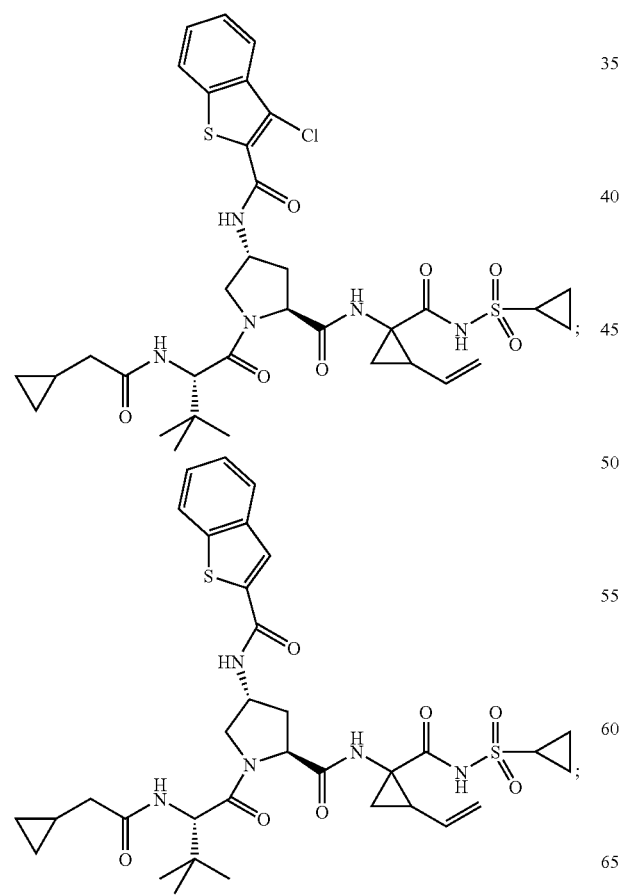

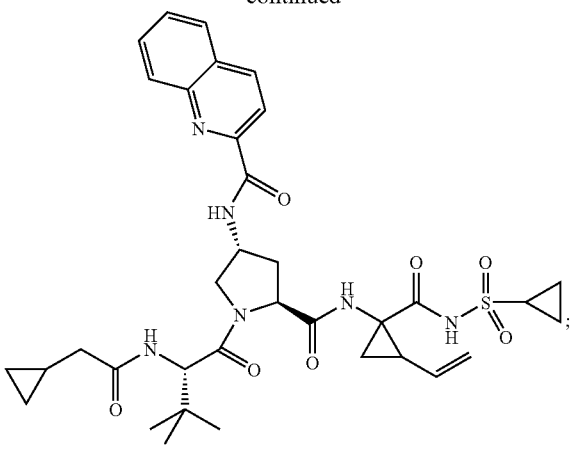

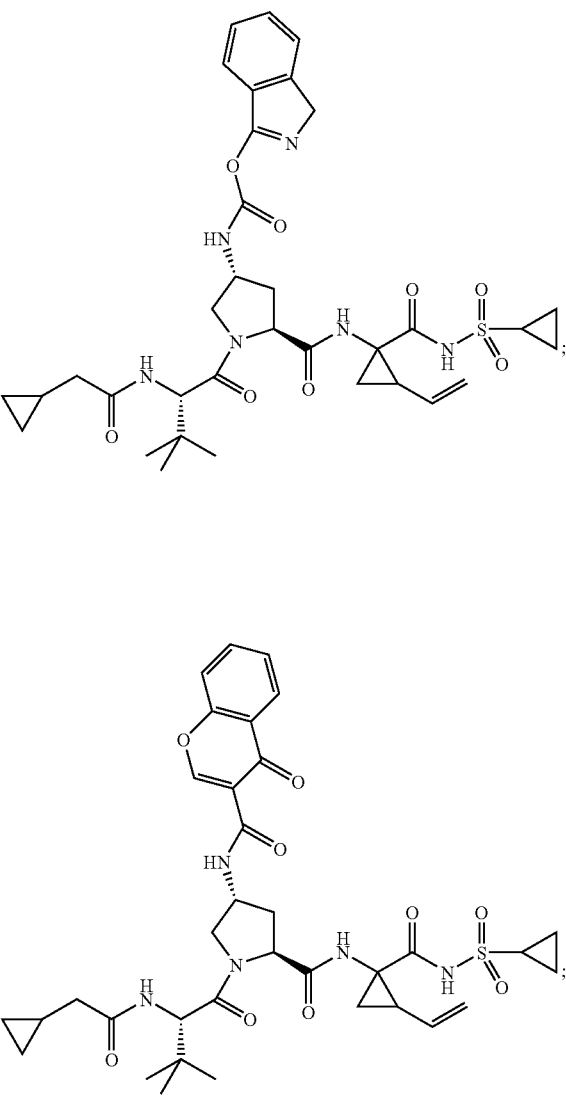

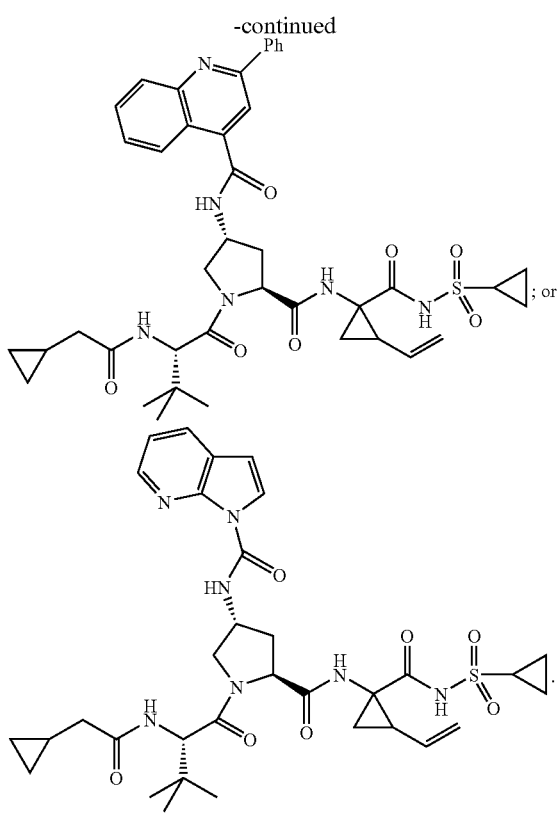

In a fifth aspect of the present disclosure is provided a composition comprising a compound of formula (I), or a pharmaceutically acceptable salt thereof, and a pharmaceutically acceptable carrier. In a first embodiment of the fifth aspect of the present disclosure the composition further comprises an interferon and ribavirin.

In a second embodiment of the fifth aspect of the present disclosure is provided a composition comprising a compound of formula (I), or a pharmaceutically acceptable salt thereof, a second compound having anti-HCV activity, and a pharmaceutically acceptable carrier. In a third embodiment of the fifth aspect of the present disclosure the second compound having anti-HCV activity is an interferon. In a fourth embodiment of the fifth aspect of the present disclosure the interferon is selected from interferon alpha 2B, pegylated interferon alpha, consensus interferon, interferon alpha 2A, and lymphoblastiod interferon tau.

In a fifth embodiment of the fifth aspect of the present disclosure is provided a composition comprising a compound of formula (I), or a pharmaceutically acceptable salt thereof, a second compound having anti-HCV activity, and a pharmaceutically acceptable carrier, wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5′-monophospate dehydrogenase inhibitor, amantadine, and rimantadine.

In a sixth embodiment of the fifth aspect of the present disclosure is provided a composition comprising a compound of formula (I), or a pharmaceutically acceptable salt thereof, a second compound having anti-HCV activity, and a pharmaceutically acceptable carrier, wherein the second compound having anti-HCV activity is a small molecule compound.

In a sixth embodiment of the fifth aspect of the present disclosure is provided a composition comprising a compound of formula (I), or a pharmaceutically acceptable salt thereof, a second compound having anti-HCV activity, and a pharmaceutically acceptable carrier, wherein the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a sixth aspect of the present disclosure is provided a method of inhibiting the function of HCV serine protease comprising contacting the HCV serine protease with the compound of formula (I) or a pharmaceutically acceptable salt thereof.

In a seventh aspect of the present disclosure is provided a method of treating an HCV infection in a patient, comprising administering to the patient a therapeutically effective amount of the compound of formula (I) or a pharmaceutically acceptable salt thereof. In a first embodiment of the seventh aspect of the present disclosure the compound is effective to inhibit the function of the HCV serine protease.

In a second embodiment of the seventh aspect of the present disclosure is provided a method of treating an HCV infection in a patient, comprising administering to the patient a therapeutically effective amount of the compound of formula (I) or a pharmaceutically acceptable salt thereof and administering a second compound having anti-HCV activity prior to, after, or simultaneously with the compound of formula (I) or a pharmaceutically acceptable salt thereof. In a third embodiment of the seventh aspect of the present disclosure the second compound having anti-HCV activity is an interferon. In a fourth embodiment of the seventh aspect of the present disclosure the interferon is selected from interferon alpha 2B, pegylated interferon alpha, consensus interferon, interferon alpha 2A, and lymphoblastiod interferon tau.

In a fifth embodiment of the seventh aspect of the present disclosure is provided a method of treating an HCV infection in a patient, comprising administering to the patient a therapeutically effective amount of the compound of formula (I) or a pharmaceutically acceptable salt thereof and administering a second compound having anti-HCV activity prior to, after, or simultaneously with the compound of formula (I) or a pharmaceutically acceptable salt thereof, wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5′-monophospate dehydrogenase inhibitor, amantadine, and rimantadine.

In a sixth embodiment of the seventh aspect of the present disclosure is provided a method of treating an HCV infection in a patient, comprising administering to the patient a therapeutically effective amount of the compound of formula (I) or a pharmaceutically acceptable salt thereof and administering a second compound having anti-HCV activity prior to, after, or simultaneously with the compound of formula (I) or a pharmaceutically acceptable salt thereof, wherein the second compound having anti-HCV activity is a small molecule.

In a seventh embodiment of the seventh aspect of the present disclosure is provided a method of treating an HCV infection in a patient, comprising administering to the patient a therapeutically effective amount of the compound of formula (I) or a pharmaceutically acceptable salt thereof and administering a second compound having anti-HCV activity prior to, after, or simultaneously with the compound of formula (I) or a pharmaceutically acceptable salt thereof, wherein the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In an eighth embodiment of the seventh aspect of the present disclosure is provided a method of treating an HCV infection in a patient, comprising administering to the patient a therapeutically effective amount of the compound of formula (I) or a pharmaceutically acceptable salt thereof and administering a second compound having anti-HCV activity prior to, after, or simultaneously with the compound of formula (I) or a pharmaceutically acceptable salt thereof, wherein the second compound having anti-HCV activity is effective to inhibit the function of target in the HCV life cycle other than the HCV serine protease.

Other aspects of the invention may include suitable combinations of embodiments and aspects disclosed herein.

Yet other aspects and embodiments may be found in the description provided herein.

Unless otherwise specifically noted herein, the terms set forth below will have the following definitions.

In certain instances the number of carbon atoms in any particular group is denoted before the recitation of the group. For example, the term "$C_{2-6}$ alkenyl" denotes an alkenyl group containing from two to six carbon atoms, and the term "$C_{7-14}$ (alkylaryl)," refers to an alkylaryl group containing a total of seven to fourteen carbon atoms.

As used herein, the singular forms "a", "an", and "the" include plural reference unless the context clearly dictates otherwise.

The term "alkenyl," as used herein, refers to a straight or branched chain hydrocarbon of two to eight carbon atoms containing at least one carbon-carbon double bond.

The term "alkoxy," as used herein, refers to an alkyl group attached to the parent molecular moiety through an oxygen atom. Representative alkoxy groups include, for example, methoxy, ethoxy, propoxy, butoxy, and tert-butoxy.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon of one to eight carbon atoms. Representative alkyl groups include, for example, methyl, ethyl, propyl, butyl, tert-butyl, hexyl, and 2-methylpropyl. The term "lower alkyl," as used herein, refers to an alkyl group having from one to six carbon atoms.

The term "alkylamino," as used herein, refers to —NHR$^a$, wherein R$^a$ is an alkyl group.

The term "alkylaminoalkyl," as used herein, refers to an alkyl group substituted with one, two, or three alkylamino groups.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfanylalkyl," as used herein, refers to an alkyl group substituted with one, two, or three alkylsulfanyl groups.

The term "alkylsulfinyl," as used herein, refers to an alkyl group attached to the parent molecular moiety through a sulfinyl group.

The term "alkylsulfinylalkyl," as used herein, refers to an alkyl group substituted with one, two, or three alkylsulfinyl groups.

The term "alkylsulfonyl," as used herein, refers to an alkyl group attached to the parent molecular moiety through a sulfonyl group.

The term "alkylsulfonylalkyl," as used herein, refers to an alkyl group substituted with one, two, or three alkylsulfonyl groups.

The term "alkynyl," as used herein, refers to a straight or branched chain hydrocarbon of two to eight carbon atoms containing at least one carbon-carbon triple bond.

The term "amido," as used herein, refers to —C(=O)NH$_2$.

The term "(lower alkyl)amido," as used herein, refers to —C(=O)NR$^a$R$^b$; wherein one of R$^a$ and R$^b$ is C$_{1-6}$ alkyl and the other is selected from hydrogen and C$_{1-6}$ alkyl.

The term "amino," as used herein, refers to —NH$_2$.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl. Unless otherwise stated, the aryl groups of the present disclosure can be optionally substituted with one, two, three, four, or five substituents independently selected from alkenyl, alkoxy, alkyl, alkylamino, amido, (lower alkyl)amido, amino, a second aryl group, cyano, cycloalkyl, carboxy, dialkylamino, halo, haloalkoxy, haloalkyl, heteroaryl, heterocyclyl, hydroxy, nitro, and oxo; wherein the second aryl group, the heteroaryl, and the heterocyclyl can be further optionally substituted with one, two, three, four, or five substituents independently selected from alkenyl, alkoxy, alkyl, halo, cyano, nitro, and oxo.

The term "arylalkyl," as used herein, refers to an aryl group attached to the parent molecular moiety through an alkyl group.

The term "aryloxy," as used herein, refers to an aryl group attached to the parent molecular moiety through an oxygen atom.

The term "carboxy," as used herein, refers to —CO$_2$H.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkenyl," as used herein, refers to a non-aromatic, partially unsaturated monocyclic, bicyclic, or tricyclic ring system having three to fourteen carbon atoms and zero heteroatoms. Representative cycloalkenyl groups include, for example, cyclohexenyl, octahydronaphthalenyl, and norbornylenyl.

The term "cycloalkenylalkyl," as used herein, refers to an alkyl group substituted with one, two, or three cycloalkenyl groups.

The term "cycloalkyl," as used herein, refers to a saturated monocyclic, bicyclic, or tricyclic hydrocarbon ring system having three to fourteen carbon atoms and zero heteroatoms.

Representative cycloalkyl groups include, for example, cyclopropyl, cyclopentyl, bicyclo[3.1.1]heptyl, and adamantyl.

The term "(cycloalkyl)alkyl," as used herein, refers to an alkyl group substituted with one, two, or three cycloalkyl groups.

The term "dialkylamino," as used herein, refers to —NR$^a$R$^b$, wherein R$^a$ and R$^b$ are the same or different C$_{1-8}$ alkyl groups.

The term "formyl," as used herein, refers to —C(=O)H.

The terms "halo" and "halogen," as used herein, refers to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative heteroaryl groups include, for example, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. Unless otherwise stated, the heteroaryl groups of the present disclosure can be optionally substituted with one, two, three, four, or five substituents independently selected from alkenyl, alkoxy, alkyl, alkylamino, amido, (lower alkyl)amido, amino, aryl, carboxy, dialkylamino, halo, haloalkoxy, haloalkyl, a second heteroaryl, heterocyclyl, hydroxy, nitro, and oxo; wherein the aryl, the second heteroaryl, and the heterocyclyl can be further optionally substituted with one, two, three, four, or five substituents independently selected from alkenyl, alkoxy, alkyl, halo, nitro, and oxo.

The term "heteroarylalkyl," as used herein, refers to an alkyl group substituted with one, two, or three heteroaryl groups.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group; and tricyclic groups in which a bicyclic system is fused to a phenyl group, a monocyclic cycloalkenyl group, a monocyclic cycloalkyl group, or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. Unless otherwise stated, the heterocyclyl groups of the present disclosure can be optionally substituted with one, two, three, four, or five substituents independently selected from alkenyl, alkoxy, alkyl, alkylamino, amido, (lower alkyl)amido, amino, aryl, carboxy, dialkylamino, halo, haloalkoxy, haloalkyl, heteroaryl, a second heterocyclyl, hydroxy, nitro, and oxo; wherein the aryl, the heteroaryl, and the second heterocyclyl can be further optionally substituted with one, two, three, four, or five substituents independently selected from alkenyl, alkoxy, alkyl, halo, nitro, and oxo.

The term "heterocyclylalkyl," as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "nitro," as used herein, refers to —NO$_2$.

The term "oxo," as used herein, refers to =O or —O$^\ominus$.

The term "sulfinyl," as used herein, refers to —S(O)—.

The term "sulfonyl," as used herein, refers to —SO$_2$—

The term "trialkylsilyl," as used herein, refers to —SiR$_3$, wherein each R is an alkyl group. The three alkyl groups may be the same or different.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylnorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

The compounds of the present disclosure may exist as prodrugs. The term "prodrug," as used herein, refers to derivatives of the compounds of the disclosure which have chemically or metabolically cleavable groups and become, by solvolysis or under physiological conditions, the compounds of the disclosure which are pharmaceutically active in vivo. A prodrug of a compound may be formed in a conventional manner with a functional group of the compounds such as with an amino, hydroxy, or carboxy group when present. The prodrug derivative form often offers advantages of solubility, tissue compatibility, or delayed release in a mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

As used herein, the term "anti-HCV activity" means the compound is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

The term "compounds of the disclosure", and equivalent expressions, are meant to embrace compounds of formula (I), and pharmaceutically acceptable enantiomers, diastereomers, salts, and solvates, e.g. hydrates, thereof. Similarly, references to intermediates are meant to embrace their salts, and solvates, where the context so permits.

As used herein, the term "small molecule compound" means a compound having a molecular weight of less than 1,500 daltons, typically less than 1000 daltons.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "substituted" as used herein includes substitution at from one to the maximum number of possible sites on the group unless otherwise specifically stated.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

The following figure shows the designations for the compounds of the present disclosure.

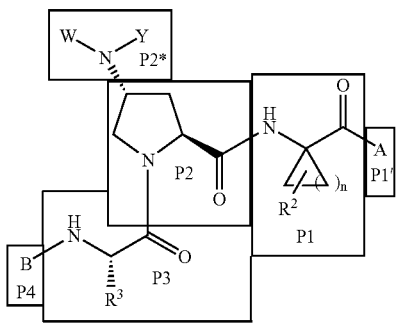

Asymmetric centers exist in the compounds of the present disclosure. For example, the compounds may include P1 cyclopropyl element of formula

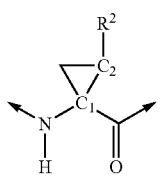

P1 wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R^2$ is configured either syn to the amide or syn to the carbonyl as shown below.

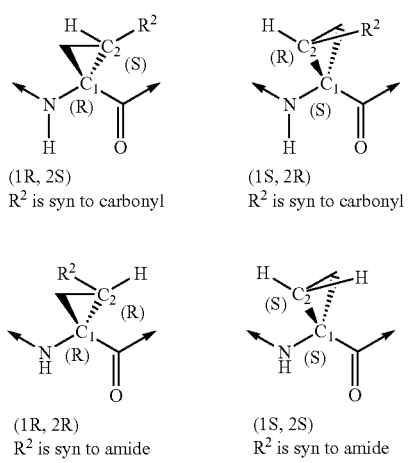

It should be understood that the disclosure encompasses all stereochemical isomeric forms, or mixtures thereof, which possess the ability to inhibit HCV protease. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, typically between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Typical unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are typically applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Certain illustrative HCV inhibitor compounds which can be administered with the compounds of the present disclosure include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |

TABLE 1-continued

| Brand Name | Type of Inhibitor or Target | Source Company |
|---|---|---|
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present disclosure, including particularly in the illustrative schemes and examples which follow, are well-known to those skilled in the art. Some of the abbreviations used are as follows: DMAP or 4-DMAP for 4-dimethylaminopyridine; CDI for 1,1'-carbonyldiimidazole; EDAC for 1-(3-dimethylaminopropyl)-3-ethylcarbodiimide hydrochloride; THF for tetrahydrofuran; DBU for 1,8-diazabicyclo[5.4.0]undec-7-ene; BOC or Boc for tert-butoxycarbonyl; TFA for trifluoroacetic acid; HATU for O-(7-azabenzotriazol-1-yl)-N,N,N',N'-tetramethyluronium hexafluorophosphate; PyBOP for benzotriazol-1-yl-oxy-tris-pyrrolidino-phosphoniumhexafluorophosphate; Me for methyl; tBu or t-Bu for tert-butyl; FMOC or Fmoc for N-(9-fluorenylmethoxycarbonyl); Et for ethyl; TBME for tert-butyl methyl ether; RT for room temperature; DMSO for dimethylsulfoxide; DI for de-ionized; OAc for acetate; DPPA for diphenylphosphoryl azide; TBAF for tetrabutylammonium fluoride; n-BuLi for n-butyllithium; tBuLi for tert-butyllithium; DEA for diethylamine; EtOH for ethanol; PyAOP for (7-azabenzotriazole-1-yloxy)tripyrrolidinophosphonium hexafluorophosphate; DIEA for diisopropylethylamine; HOBt for 1-hydroxybenzotriazole hydrate; HBTU for O-benzotriazol-1-yl-N,N,N',N'-tetramethyluronium hexafluorophosphate; Cp for cyclopropyl; and Et$_3$N for triethylamine.

The starting materials useful to synthesize the compounds of the present disclosure are known to those skilled in the art and can be readily manufactured or are commercially available.

The following methods set forth below are provided for illustrative purposes and are not intended to limit the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The compounds of the present disclosure may, for example, be synthesized according to a general process as illustrated in Scheme I (wherein CPG is a carboxy protecting group and APG is an amino protecting group).

Scheme I

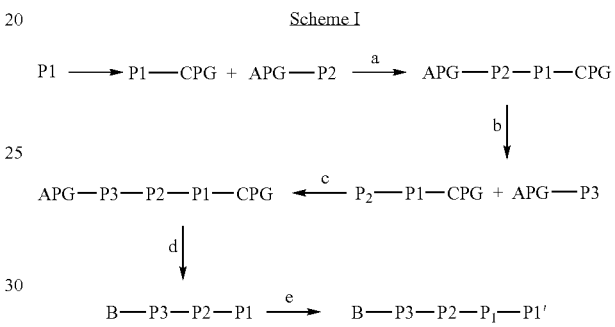

Briefly, the P1', P1, P2, P3 and P4 can be linked by well known peptide coupling techniques. The P1', P1, P2, P3 and P4 groups may be linked together in any order as long as the final compound corresponds to peptides of the disclosure. For example, P3 can be linked to P2-P1; or P1 linked to P3-P2.

Generally, peptides are elongated by deprotecting the α-amino group of the N-terminal residue and coupling the unprotected carboxy group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxy of one reactant with the free amino group of the other reactant in the present of a coupling agent to form a linking amide bond. Descriptions of such coupling agents are found in general textbooks on peptide chemistry, for example, M. Bodanszky, "Peptide Chemistry", 2$^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 minutes and 24 hours.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York and "The Peptides: Analysis, Synthesis, Biology", Vol. 3, Academic Press, New York (1981).

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl.

In one embodiment the α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20-22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenyhnethyl (Trityl) moiety can be used to protect the sulfide containing side chain of cysteine.

Once the elongation of the peptide is completed all of the protecting groups are removed. These procedures are well known to those skilled in the art.

Further, the following guidance may be followed in the preparation of compounds of the present disclosure. For example, to form a compound where B is $R^6$—C(=O)— or $R^6SO_2$—, a protected P3 or the whole peptide or a peptide segment is coupled to an appropriate acyl chloride or sulfonyl chloride respectively, that is either commercially available or for which the synthesis is well known in the art.

In preparing a compound where B is $R^6O(C=O)$—, a protected P3 or the whole peptide or a peptide segment is coupled to an appropriate chloroformate that is either commercially available or for which the synthesis is well known in the art. For Boc-derivatives $(Boc)_2O$ is used.

For example:

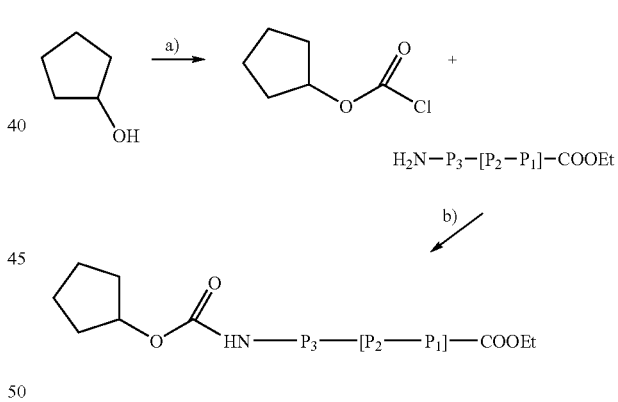

Cyclopentanol is treated with phosgene to furnish the corresponding chloroformate.

The chloroformate is treated with the desired $NH_2$-tripeptide in the presence of a base such as triethylamine to provide the cyclopentylcarbamate.

In preparing a compound where B is $R^6$—$N(R^7)$—C(=O)— or $R^6$—$N(R^7)$—C(=S)—, a protected P3 or the whole peptide or a peptide segment is treated with phosgene followed by amine as described in *Syn. Lett.* February 1995; (2); 142-144 or is reacted with the commercially available isocyanate and a suitable base such as triethylamine.

In preparing a compound where B is $R^6$—$N(R^7)$—$SO_2$—, a protected P3 or the whole peptide or a peptide segment is treated with either a freshly prepared or commercially available sulfamyl chloride followed by amine as described in WO 98/32748.

The α-carboxy group of the C-terminal residue is usually protected as an ester (CPG) that can be cleaved to give the carboxylic acid. Protecting groups that can be used include: 1) alkyl esters such as methyl, trimethylsilylethyl and tert-butyl, 2) aryllkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R^1SO_2NH_2$ (prepared by treatment of $R^1SO_2Cl$ in ammonia saturated tetrahydrofuran solution) in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, effectively assembling the tripeptide P1'-P1-P2-P3-APG. Typically, in this process, 1-5 equivalents of P1' coupling agents are used.

Furthermore, if the P3 protecting group APG is removed and replaced with a P4 moiety by the methods described above, and the resulting α-carboxylic acid resulting from cleavage (resulting from cleavage by mild acid, mild base treatment or mild reductive means) is coupled with a $R^1SO_2NH_2$ (prepared by treatment of $R^1SO_2Cl$ in ammonia saturated tetrahydrofuran solution or alternative methods described herein) in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, the tripeptide P1'-P1-P2-P3-P4 is prepared. Typically, in this process, 1-5 equivalents of P1' coupling agents are used.

Scheme II further shows the general process wherein compounds of Formula (I) are constructed by the coupling of tripeptide carboxylic acid (1) of Formula (I) with a P1' sulfonamide. Said coupling reaction requires treatment of carboxylic acid (1) with a coupling reagent such as carbonyldiimidazole in a solvent such as THF, which can be heated to reflux, followed by the addition of the formed derivative of (1), to the P1' sulfonamide, in a solvent such as THF or dichloromethane in the presence of a base such as DBU.

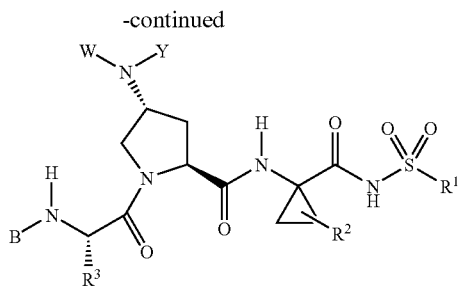

An alternative process for the construction of compounds of Formula (I) is shown in Scheme III. Therein the P1' sulfonamide element is coupled to the P1 element using the process employed in Scheme 1. The resulting P1-P1' moiety can then be deprotected at its amino terminus. In this general example a Boc protecting group is employed but one skilled in the art would recognize that a number of suitable amino protecting groups could be employed in this process. Said Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme III. The coupling of said HCl amine salt (3) with the carboxy terminus a P4-P3-P2 intermediate can be achieved using coupling reagents, such as HATU, in solvents such as dichloromethane to provide compounds of Formula (I) (4).

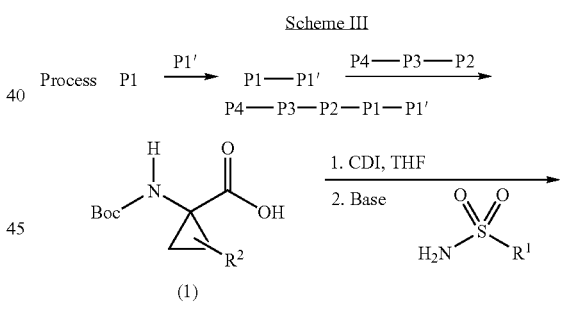

Scheme II

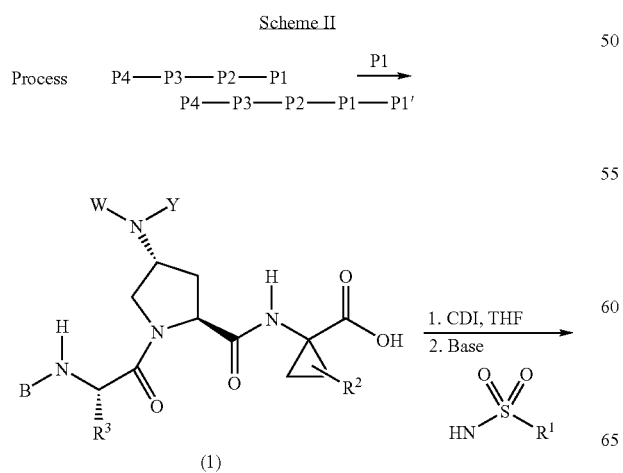

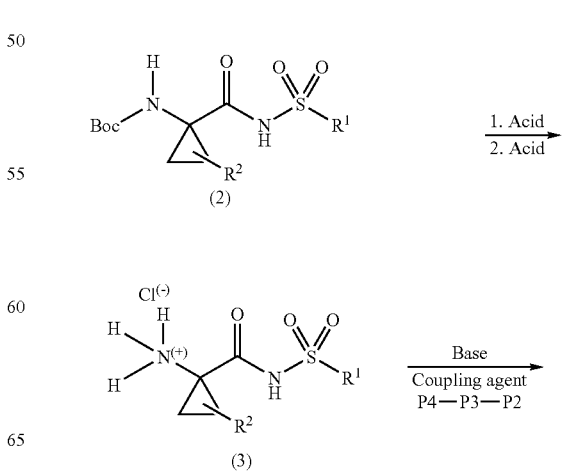

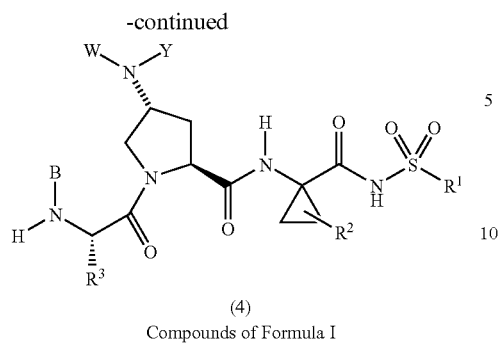

(4)
Compounds of Formula I

An alternative process for the construction of compounds of Formula (I) is shown in Scheme IV. The hydrochloride salt of the P1-P1' terminal amine (1) is coupled to the free carboxy group of the P2 element using coupling agents such as PyBOP, in the presence of a base such as diisopropyl amine, and in a solvent such as dichloromethane. The resulting P2-P1-P1' intermediate can be converted to compounds of Formula (I) in a two step process wherein the first step is deprotection of the P2 amine terminus using an acid such as TFA in a solvent such as dichloromethane. The resulting trifluoroacetic acid salt can be coupled with the carboxy terminus of the P4-P3 element using standard coupling agents such as PyBOP in the presence of base such as diisopropyl amine, and using solvents such dichloromethane to provide compounds of Formula (I) (4).

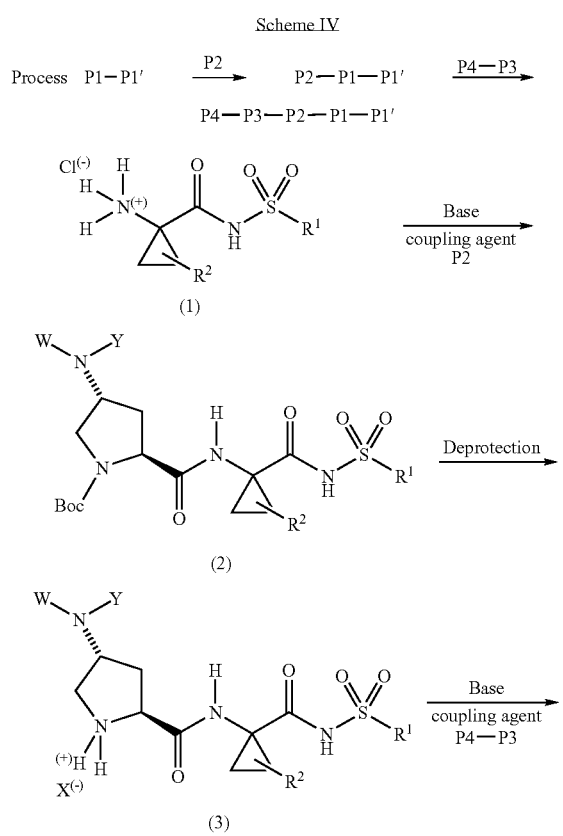

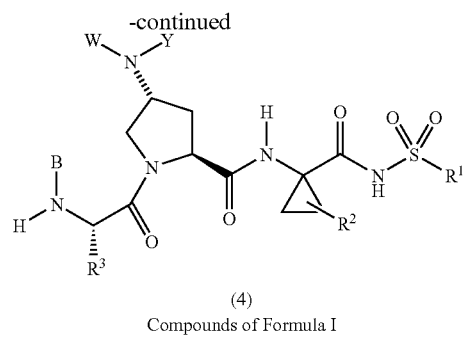

(4)
Compounds of Formula I

The P4-P3-P2 intermediate utilized in the above schemes can be constructed as previously described with a further description of this process shown in general Scheme V. Therein the free carboxy terminus of the P4-P3 intermediate (1), can be coupled to the amino terminus of the P2 element to provide the P4-P3-P2 dipeptide (2). The carboxy terminus of the P4-P3-P2 intermediate can be deprotected by saponification of the ester group to provide P4-P3-P2 as the free carboxylic acid (3). Intermediates like (3) can be converted to compounds of Formula (I) using the methods described herein.

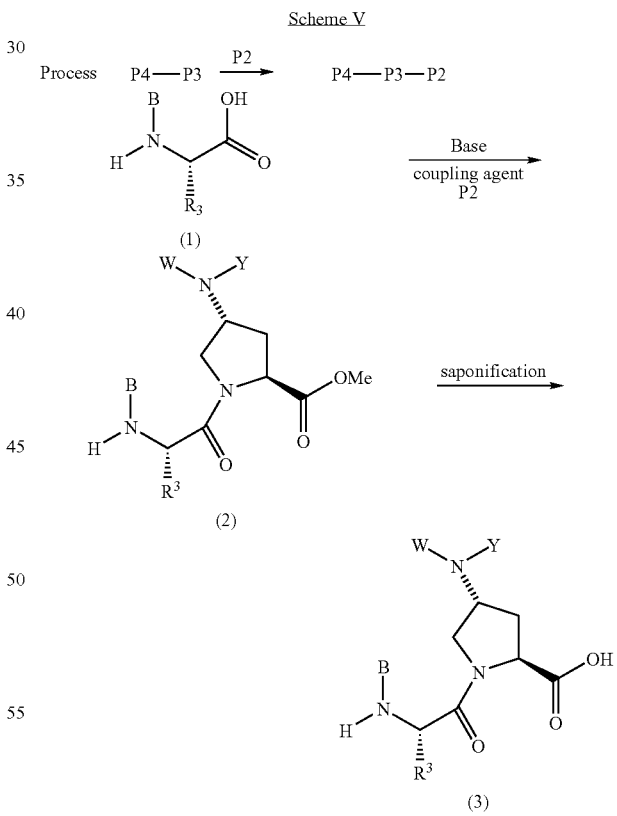

Compounds of Formula (I) can also be converted into other compounds of Formula (I) as described herein. An example of such a process is shown in Scheme VI wherein a compound of Formula (I) (1) which bears a Boc group at the P4 position is converted in a compound of Formula (I) (3) wherein said compound bears a urea group at the P4 position. The conversion of (1) to (3) can be carried out in a two step process the first of which is the conversion of (1) to amine (2) by treatment of (1) with an acid such as TFA in a solvent such as dichloromethane. The resulting amine TFA salt can be treated with an isocyanate in the presence of one equivalent of base to provide a compound of Formula (I) (3) wherein the P3 moiety is capped with a urea. As previously noted one skilled in the art will recognize that intermediate (2) can be used as starting materials for the preparation of compounds of Formula (I) wherein the P3 group is capped with an amide or a sulfonamide, or thiourea, or a sulfamide. The construction of said compounds of Formula (I) can be achieved using standard conditions for the formation of said P4 functionalities from amines.

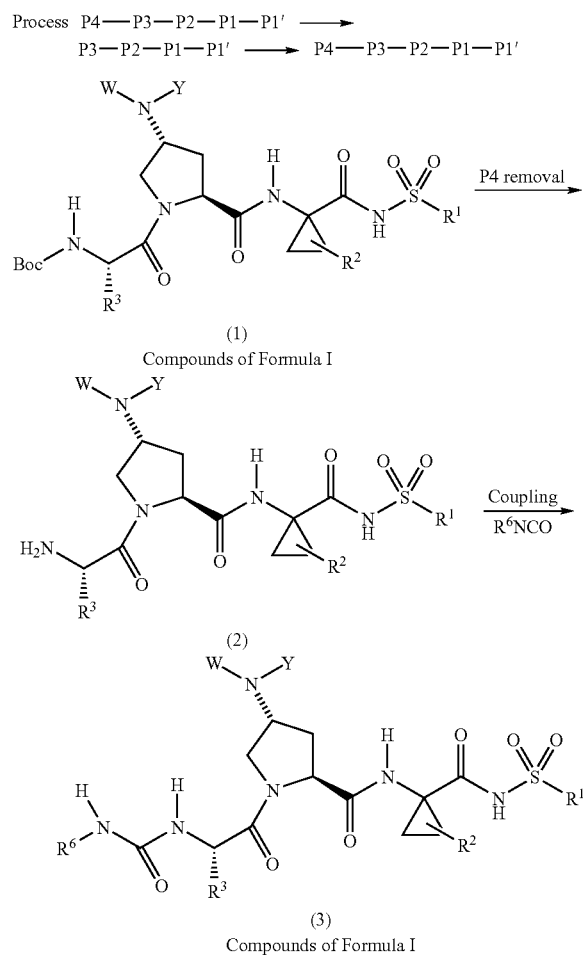

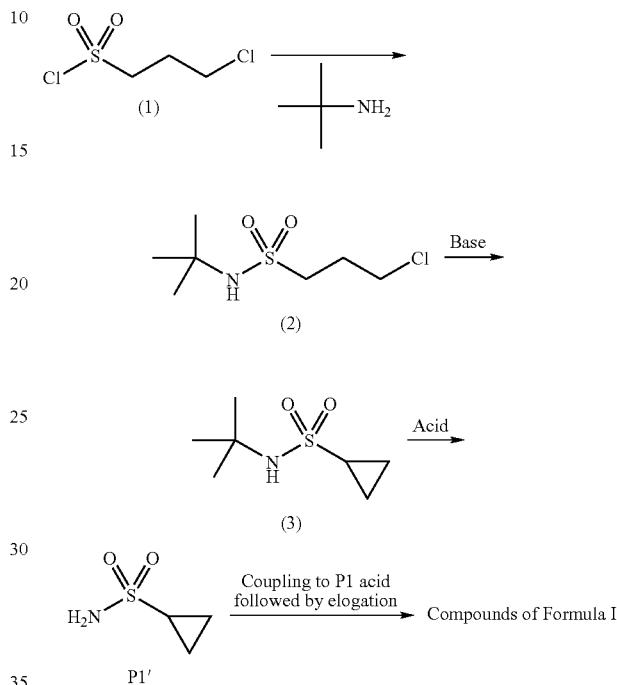

cycloalkylsulfonamide by treatment with two equivalents of a base such as butyl lithium in a solvent such as THF at low temperature. The resulting cycloalkylsulfonamide can be deprotected by treatment with an acid to provide the desired unprotected cycloalkylsulfoamide.

Additionally, compounds of Formula (I) can be prepared in which the cycloalkyl moiety of a P1' cycloalkyl sulfonamide group is optionally substituted. Said compounds can be prepared by using the general process outlined in Scheme VIII wherein a suitably protected cyclopropylsulfoamide(1) is treated with strong base to affect deprotonation. At least two equivalents of base is required to deprotonate both the sulfonamide nitrogen and the C1-(alpha) position of the cyclopropyl group. Subsequent addition of an electrophile to a solution of the anion of (1) provides the C1-(alpha) functionalized cyclopropylsulfonamide (2). Intermediate 2 is then deprotected to provide a C1-substituted cyclopropylsulfonamide as described herein.

In the construction of compounds of Formula (I), the P1' terminus is incorporated into the molecules using one of the general processes outlined above and described in more detail below. In some examples the P1' elements, that is the cycloalkyl- or alkylsulfonamides, are commercially available or can be prepared from the corresponding alkyl- or cycloalkylsulfonyl chloride, by treating said sulfonyl chloride with ammonia. Alternatively, these sulfonamides can be synthesized using the general process outline in Scheme VII. Therein commercially available 3-chloropropylsulfonyl chloride (1) is converted to a suitable protected sulfonamide as for example by treatment with tert-butyl amine. The sulfonamide obtained (2) is then converted to the corresponding

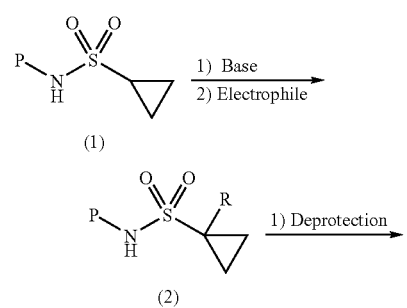

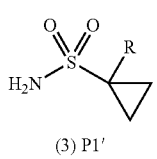

(3) P1'

Coupling to P1 acid
followed by elogation

Compounds of Formula I

The P1 elements utilized in generating compounds of Formula (I) are in some cases commercially available, but are otherwise synthesized using the methods described herein and subsequently incorporated into compounds of Formula (I) using the methods described herein. The substituted P1 cyclopropylamino acids can be synthesized following the general process outline in Scheme IX.

Treatment of commercially available or easily synthesized imine (1) with 1,4-dihalobutene (2) in presence of a base produces, provides the resulting imine (3). Acid hydrolysis of 3 then provides 4, which has an allyl substituent syn to the carboxy group as a major product. The amine moiety of 4 can protected using a Boc group to provide the fully protected amino acid 5. This intermediate is a racemate which can be resolved by an enzymatic process wherein the ester moiety of 5 is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, one stereoisomer for integration into compounds of Formula (I) is 5a which houses the (1R,2S) stereochemistry. In the presence of the enzyme, this enantiomer does not undergo ester cleavage and thereby this enantiomer 5a is recovered from the reaction mixture. The other enantiomer, 5b, which houses the (1S,2R) stereochemistry undergoes ester cleavage, i.e., hydrolysis, to provide the free acid 6. Upon completion of this reaction, the ester 5a can be separated from the acid product 6 by routine methods such as, for example, aqueous extraction methods or chromatography.

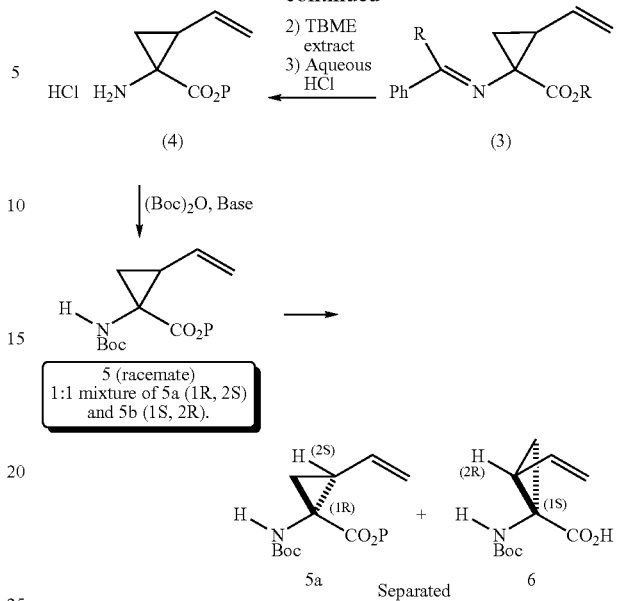

Procedures for making P2 intermediates and compounds of Formula (I) are shown in the schemes below. It should be noted that in many cases reactions are depicted for only one position of an intermediate. However, it is to be understood that such reactions could be used to impart modifications to other positions within this intermediate. Moreover, said intermediates, reaction conditions and methods given in the specific examples are broadly applicable to compounds with other substitution patterns. The general schemes outlined below are followed with examples herein. Both general and specific examples are non-limiting. For example, compounds of the present disclosure can be made via intermediate (1) of Scheme X. One skilled in the art would readily recognize that intermediate (1) is available using the above described procedures. This intermediate can then be converted to compounds of Formula (I) by the process shown, wherein the Fmoc group of (1) is deprotected under standard conditions to provide the amine intermediate (2). The amine is then subjected to a base such as diisopropylamine, or triethylamine in a solvent such as dichloromethane or THF followed by the addition of an acylating agent or a sulfonalating to provide compounds of Formula 1. It should be noted that the acylating agents used include but are not limited to acyl chlorides, carbamoyl chlorides, and isocyanates. Alternatively, the amine of intermediate (2) can be coupled with a carboxylic acid to provide functionalized amides.

Scheme IX

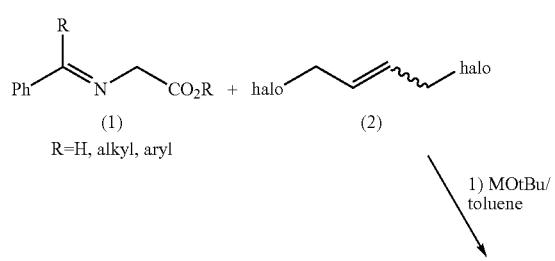

Scheme X

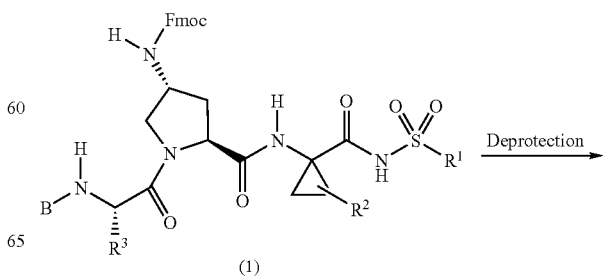

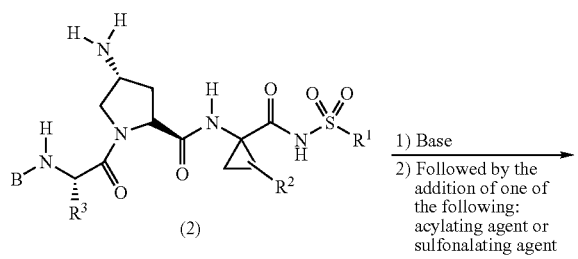

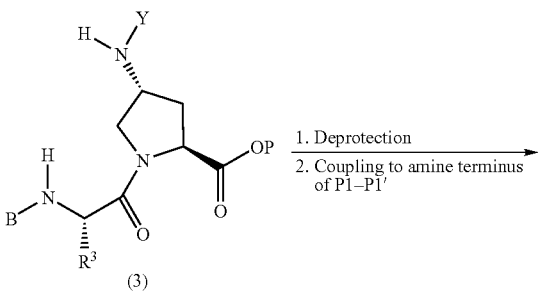

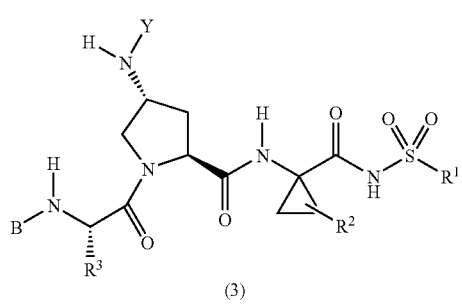

Compounds of Formula I

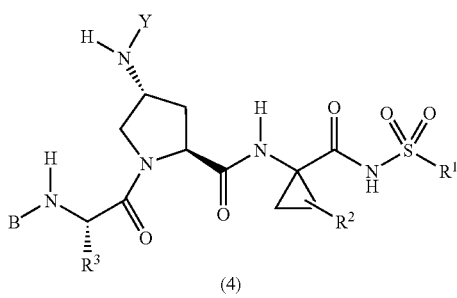

Compounds of Formula I

The transformations described for the formation of compounds of Formula (I) from intermediate 1 of Scheme X can also be used on intermediate fragments described above as for example a P4-P3-P2 fragment wherein the proline P2 carboxylic acid group is suitably protected as shown in Scheme XI.

Scheme XI

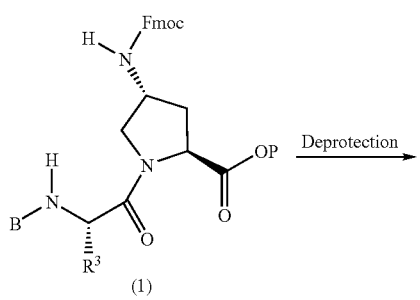

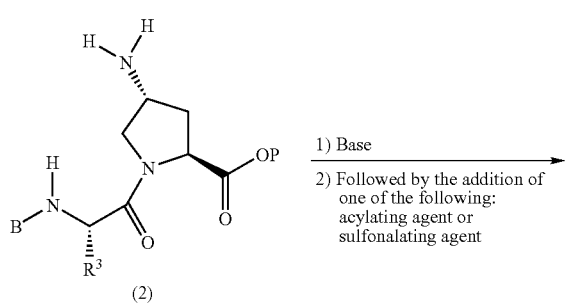

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts ($\delta$) are reported in parts per million. Flash chromatography was carried out on silica gel ($SiO_2$) according to Still's flash chromatography technique (*J. Org. Chem.* 1978, 43, 2923).

Section A: Preparation of Intermediates

Section A.I: Preparation of P1 Intermediates

The P1 intermediates described in this section may be used to prepare compounds of Formula (I) by the methods described herein.

Example 1

Racemic (1R,2S)/(1S,2R)-1-amino-2-vinylcyclopropane carboxylic acid ethyl ester hydrochloride was prepared (Method A and Method B) and chiral resolution of this racemate for the preparation of N-(1R,2S)-1-amino-2-vinylcyclopropane carboxylic acid ethyl ester hydrochloride (Method C) was carried out.

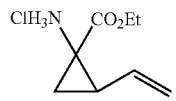

The named compound was made racemic by each of the following Methods A and B. This racemate could also be resolved to provide chiral Boc-(1R,2S)-1-amino-2-vinylcyclopropyl carboxylic acid ester which was deprotected under acid conditions to provide (1R,2S)-1-amino-2-vinylcyclopropane carboxylic acid ester hydrochloride (Method C).

Method A

A.1) Preparation of N-Benzyl Imine of Glycine Ethyl Ester

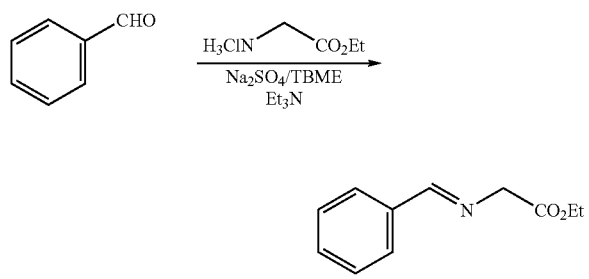

Glycine ethyl ester hydrochloride (303.8 g, 2.16 mol) was suspended in tert-butylmethyl ether (1.6 L). Benzaldehyde (231 g, 2.16 mol) and anhydrous sodium sulfate (154.6 g, 1.09 mol) were added and the mixture cooled to 0° C. using an ice-water bath. Triethylamine (455 mL, 3.26 mol) was added dropwise over 30 minutes and the mixture stirred for 48 hours at room temperature. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO$_3$ (1 L) and brine (1 L). The solution was dried over MgSO$_4$, filtered, and concentrated in vacuo to provide 392.4 g of the N-benzylimine product as a thick yellow oil that was used directly in the next step. $^1$H NMR (CDCl$_3$, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

A.2) Preparation of racemic N-Boc-(1R,2S)/(1S,2R)-1-amino-2-vinylcyclopropane carboxylic acid ethyl ester

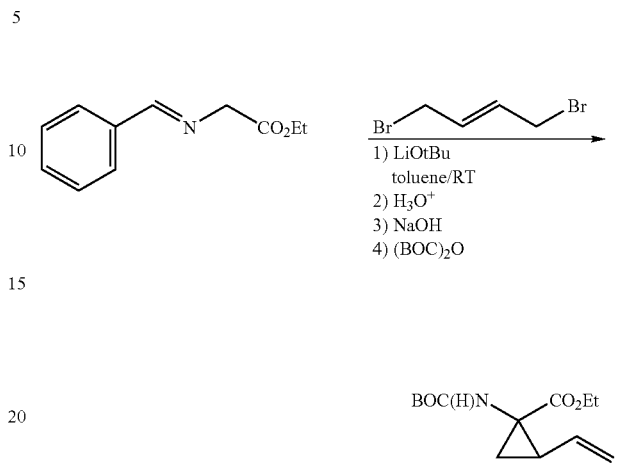

To a suspension of lithium tert-butoxide (84.06 g, 1.05 mol) in dry toluene (1.2 L), was added dropwise a mixture of the N-benzylimine of glycine ethyl ester (100.4 g, 0.526 mol) and trans-1,4-dibromo-2-butene (107.0 g, 0.500 mol) in dry toluene (0.6 L) over 60 minutes. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 hours. The organic phase was separated and extracted with water (0.8 L). The aqueous phases were then combined, saturated with salt (700 g), TBME (1 L) was added and the mixture cooled to 0° C. The stirred mixture was then adjusted to pH 14 by the dropwise addition of 10 N NaOH, the organic layer separated, and the aqueous phase extracted with TBME (2×500 mL). The combined organic extracts were dried (MgSO$_4$), filtered, and concentrated to a volume of 1 L. To this solution of free amine was added di-tert-butyldicarbonate (131.0 g, 0.6 mol) and the mixture stirred 4 days at room temperature. Additional di-tert-butyldicarbonate (50 g, 0.23 mol) was added to the reaction, the mixture refluxed for 3 hours, and was then allowed cool to room temperature overnight. The reaction mixture was dried over MgSO$_4$, filtered, and concentrated in vacuo to provide 80 g of crude material. This residue was purified by flash chromatography (2.5 Kg of SiO$_2$, eluted with 1% to 2% methanol/CH$_2$Cl$_2$) to provide 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M−1)

A.3) Preparation of Racemic (1R,2S)/(1S,2R) 1-amino-2-vinylcyclopropane carboxylic acid ethyl ester hydrochloride

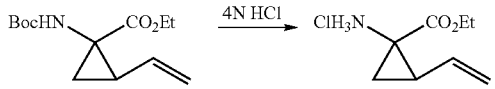

N-Boc-(1R,2S)/(1S,2R)-1-amino-2-vinylcyclopropane carboxylic acid ethyl ester (9.39 g, 36.8 mmol) was dissolved in 4 N HCl/dioxane (90 mL, 360 mmol) and was stirred for 2 hours at room temperature. The reaction mixture was concentrated to supply (1R,2S)/(1S,2R)-1-amino-2-vinylcyclopropane carboxylic acid ethyl ester hydrochloride in quantitative yield (7 g, 100%). $^1$H NMR (methanol-$d_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26-4.34 (m, 2H), 5.24 (dd, 10.3, 1.3 Hz, 1H) 5.40 (d, J=17.2, 1H), 5.69-5.81 (m, 1H).

Method B: Preparation of Racemic N-Boc-1-amino-2-vinylcyclopropane carboxylic acid ethyl ester hydrochloride

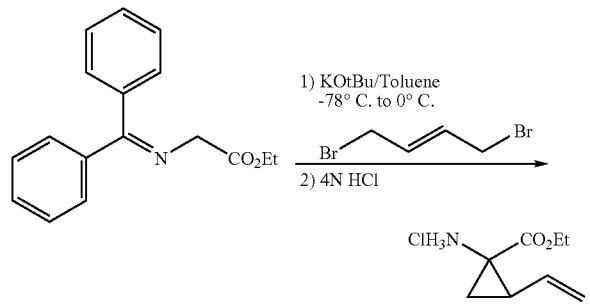

To a solution of potassium tert-butoxide (11.55 g, 102.9 mmol) in THF (450 mL) at −78° C. was added the commercially available N,N-dibenzylimine of glycine ethyl ester (25.0 g, 93.53 mmol) in THF (112 mL). The reaction mixture was warmed to 0° C., stirred for 40 minutes, and was then cooled back to −78° C. To this solution was added trans-1,4-dibromo-2-butene (20.0 g, 93.50 mmol), the mixture stirred for 1 hour at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in diethyl ether (530 mL), 1N HCl solution (106 mL, 106 mmol) was added, and the resulting biphasic mixture was stirred for 3.5 hours at room temperature. The layers were separated and the aqueous layer was washed with diethyl ether (2×) and basified with a saturated NaHCO$_3$ solution. The desired amine was extracted with diethyl ether (3×) and the combined organic extract was washed with brine, dried (MgSO$_4$), filtered, and concentrated in vacuo to obtain the free amine. This material was treated with a 4N HCl solution in dioxane (100 mL, 400 mmol) and concentrated to provide (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Method C: Resolution of N-Boc-(1R,2S)/(1S,2R)-1-amino-2-vinylcyclopropane carboxylic acid ethyl ester

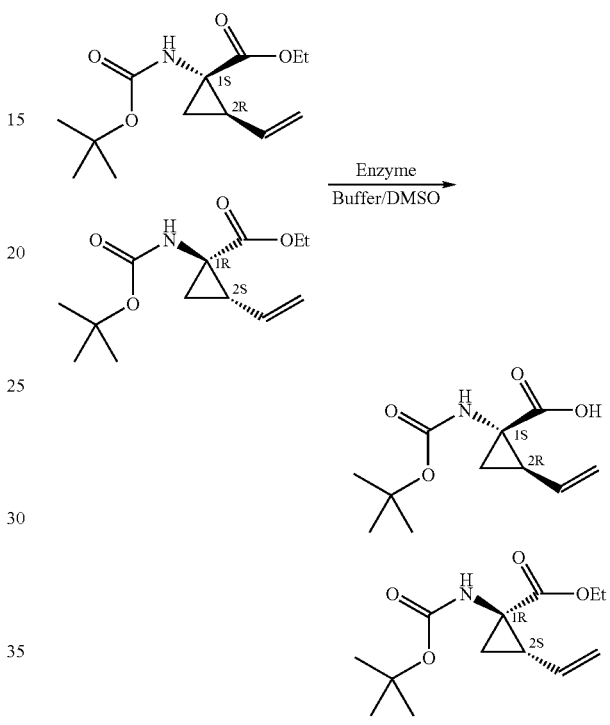

racemate: 1:1 mixture of (1R, 2S) and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 minutes. The reaction temperature was then maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and concentrated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee").

The aqueous layer from the extraction process was then acidified to pH 2 with 50% H$_2$SO$_4$ and extracted with MTBE (2×2 L). The MTBE extract was washed with water (3×100 mL) and concentrated to give the acid as light yellow solid (42.74 g; purity: 99% @ 210 nm, containing no ester).

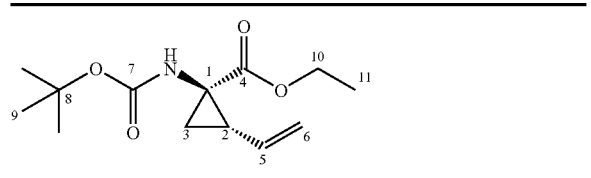

1R, 2S-ester 1S, 2R-acid

|  | ester | acid |
|---|---|---|
| High Resolution Mass Spec | (+) ESI, C$_{13}$H$_{22}$NO$_4$, [M + H]$^+$, calcd. 256.1549, found 256.1542 | (−) ESI, C$_{11}$H$_{16}$NO$_4$, [M − H]$^-$, calcd. 226.1079, found 226.1089 |

NMR observed chemical shift
Solvent: CDCl$_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) |  | 1.51, (br) |  |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) |  | 5.12(d, J = 10.5 Hz) |  |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B

To 0.5 mL 100 mM Heps.Na buffer (pH 8.5) in a well of a 24 well plate (capacity: 10 mL/well), 0.1 mL of Savinase 16.0 L (protease from *Bacillus clausii*) (Novozymes North America Inc.) and a solution of the racemic N-Boc-(1R,2R)/(1S,2S)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% as following: 0.1 mL of the reaction mixture was removed and mixed well with 1 mL ethanol; after centrifugation, 10 microliter ("μL") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μL of the supernatant was analyzed with the chiral HPLC and enantio-excess of the ester was determined to be 100%.

Resolution C

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 μL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 μL of the supernatant was analyzed with the chiral HPLC and enantio-excess of the ester was determined to be 100%.

Samples analysis was carried out in the following manner:
1) Sample preparation: About 0.5 mL of the reaction mixture was mixed well with 10 volume of ethanol. After centrifugation, 10 μl of the supernatant was injected onto HPLC column.
2) Conversion determination:

Column: YMC ODS A, 4.6×50 mm, S-5 μm

Solvent: A, 1 mM HCl in water; B, CH$_3$CN

Gradient: 30% B for 1 min; 30% to 45% B over 0.5 min; 45% B for 1.5 min; 45% to

30% B over 0.5 minutes.

Flow rate: 2 mL/min

UV Detection: 210 nm

Retention time: acid, 1.2 min; ester, 2.8 minutes.
3) Enantio-excess determination for the ester:

Column: CHIRACEL OD-RH, 4.6×150 mm, S-5 μm

Mobile phase: CH$_3$CN/50 mM HClO$_4$ in water (67/33)

Flow rate: 0.75 mL/min.

UV Detection: 210 nm.

Retention time:

(1S,2R)-1-amino-2-vinylcyclopropane carboxylic acid 5.2 min; Racemate (1R,2S)/(1S,2R)-1-amino-2-vinylcyclopropane carboxylic acid ethyl ester 18.5 minutes and 20.0 min;

(1R,2S)-1-amino-2-vinylcyclopropane carboxylic acid ethyl ester 18.5 minutes.

Resolution D

5 L of 0.3 M sodium phosphate buffer (pH 8) was maintained at 38° C. in a 20 Liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funnel. The reaction temperature was then adjusted to 48° C. After 21 hours, enantio-excess of the ester reached 99.3%. Heating was stopped at 24 hours and the reaction was slowly cooled down to room temperature (about 25° C.) and stirred overnight. The pH of the reaction mixture was adjusted to 8.5 with 10 N NaOH and the mixture was extracted with MTBE (2×4 L). The combined MTBE extract was washed with 5% NaHCO$_3$ (3×400 mL) and water (3×400 mL), and concentrated to give enantiomerically pure N-Boc-(1R,2S)/-1-amino-2-vinylcyclopropane carboxylic acid ethyl ester as light yellow crystal (259 g; purity: 96.9% (210 nm, containing no acid; 100% ee).

Resolution E

10 L of 0.1 M sodium phosphate buffer (pH 8) was maintained at 40° C. in a 20 Liter jacked reactor, stirred at 360 rpm. 1.5 liters of Alcalase 2.4 L (Novozymes North America Inc.) was added to the reactor. When the temperature of the mixture closed to 38° C., the pH was adjusted to 8.0 with 10 N NaOH. room temperature under house vacuum and gave enantiomerically pure N-Boc-(1R,2S)/-1-amino-2-vinylcyclopropane carboxylic acid ethyl ester as colorless long rod crystal (101 g; purity: 97.9% @ 210 nm, containing no acid; 100% ee).

The crystal structure enantiomerically pure N-Boc-(1R, 2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester:

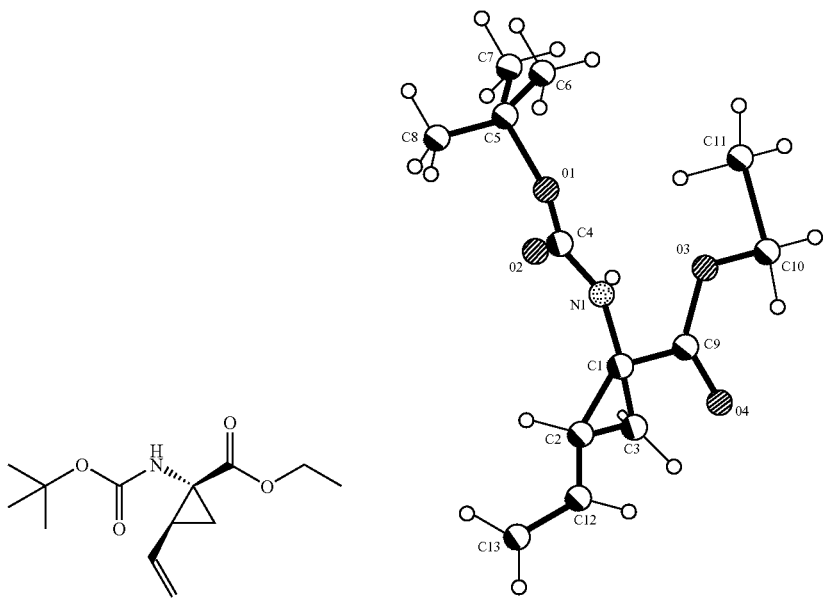

Crystal Data:

Chemical formula: C13H21N1O4
Crystal system: Orthorhombic
Space Group: P2$_1$2$_1$2$_1$
a = 5.2902(1) Å   α = 90.°
b = 13.8946(2) Å  β = 90°
c = 19.9768(3) Å  γ = 90°
V = 1468.40(4) Å$^3$
Z = 4    d$_x$ = 1.155 g cm$^{-3}$
No. of reflections for lattice parameters: 6817
θ range for lattice parameters (°): 2.2-65.2
Absorption coefficient (mm$^{-1}$): 0.700

Experimental:

Crystallization
Crystal source: MTBE
Crystal description: Colorless rod
Crystal size (mm): 0.12 × 0.26 × 0.30
Data Collection
Temperature (K): 293
.θ$_{max}$ (°): 65.2  (Cu Kα)
No. of reflections measured: 7518
No. of independent reflections: 2390 (R$_{int}$ = 0.0776)
No. of observed reflections (I ≧ 2σ.: 2284
Absorption correction (T$_{min}$-T$_{max}$): 0.688-1.000

A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, the pH was adjusted to 8.0 with 10 N NaOH. After 21 hours, the reaction was cooled down to 25° C., the pH of the reaction mixture was adjusted to 8.5 with 10 N NaOH and the mixture was extracted with MTBE (2×5 L). The combined MTBE extract was washed with 5% NaHCO$_3$ (3×500 mL) and water (3×200 mL), and concentrated to give 110 gram of yellow oil. The oil was set at Resolution F 5 L of 0.2 M sodium borate buffer (pH 9) was maintained at 45° C. in a 20 liter jacked reactor, and stirred at 400 rpm. Three liter of DI water and four liters of Savinase 16L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 minutes, via an addition funnel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hours, temperature was lowered to 35° C. At 42 hours, the temperature was raised to 48° C. and the pH was adjusted to 9.0 with 10 N NaOH. Heating was stopped at 48 hours and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO$_3$ (6×300 mL) and water (3×300 mL), and concentrated to give enantiomerically pure N-Boc-(1R,2S)/-1-amino-2-vinylcyclopropane carboxylic acid ethyl ester as light yellow crystal (101A g; purity: 95.9%® 210 nm, containing no acid; 98.6% ee).

Example 2

Chiral (1R,2S)-1-amino-2-vinylcyclopropane carboxylic acid ethyl ester hydrochloride was Prepared

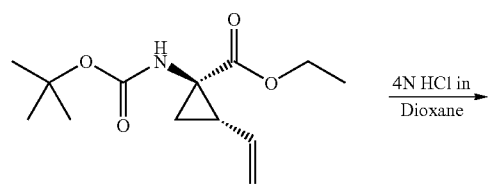

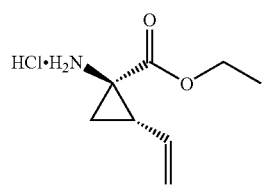

N-Boc-(1R,2S)-1-amino-2-vinylcyclopropanecarboxylic acid ethyl ester (8.5 g, 33.3 mmol) was stirred under an N$_2$ atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). LC-MS (Method A, retention time: 0.58 min), MS m/z 156 (M$^+$+1).

Example 3

N-Boc-(1R,2S)-1-amino-2-cyclopropylcyclopropane carboxylic acid ethyl ester was Prepared

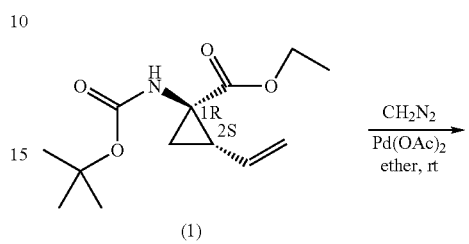

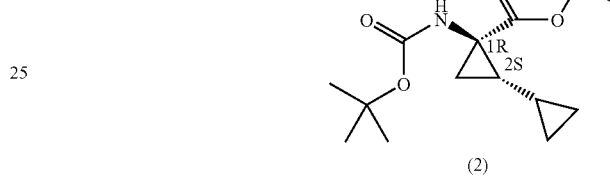

A solution of N-Boc-(1R,2S)-1-amino-2-vinylcyclopropane carboxylic acid (255 mg, 1.0 mmol) in diethyl ether (10 mL) was treated with palladium acetate (5 mg, 0.022 mmol). The orange/red solution was placed under an atmosphere of N$_2$. An excess of diazomethane in ether was added dropwise over the course of 1 hour. The resulting solution was stirred at room temperature for 18 hours. The excess diazomethane was removed using a stream of nitrogen. The resulting solution was concentrated by rotary evaporation to give the crude product. Flash chromatography (10% ethyl acetate/hexane) provided 210 mg (78%) of N-Boc-(1R,2S)-1-amino-2-cyclopropylcyclopropane carboxylic acid ethyl ester as a colorless oil. LC-MS (retention time: 2.13, similar to method A except: gradient time 3 minutes, Xterra MS C18 S7 3.0×50 mm column), MS m/e 270 (M$^+$+1).

Example 4

1-tert-butoxycarbonylamino-cyclopropane-carboxylic acid, Shown Below, is Commercially Available

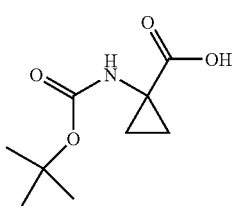

example 5

1-aminocyclobutanecarboxylic acid methyl ester-hydrochloride was Prepared

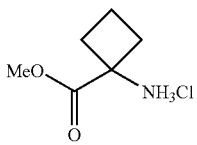

1-Aminocyclobutanecarboxylic acid (100 mg, 0.869 mmol)(Tocris) was dissolved in 10 mL of methanol, HCl gas was bubbled in for 2 hours. The reaction mixture was stirred for 18 hours, and then concentrated in vacuo to give 144 mg of a yellow oil. Trituration with 10 mL of ether provided 100 mg of the desired product as a white solid. $^1$H NMR (CDCl$_3$) δ 2.10-2.25 (m, 1H), 2.28-2.42 (m, 1H), 2.64-2.82 (m, 4H), 3.87 (s, 3H), 9.21 (br s, 3H).

Example 6

Racemic (1R,2R)/(1S,2S) 1-amino-2-ethylcyclopropanecarboxylic acid tert-butyl ester, Shown Below, was Prepared

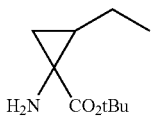

ethyl syn to carboxy

Step 6a: Preparation of 2-Ethylcyclopropane-1,1-dicarboxylic acid di-tert-butyl ester, Shown Below

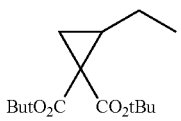

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred for 18 hours at room temperature, a mixture of ice and water was then added. The crude product was extracted with CH$_2$Cl$_2$ (3×) and sequentially washed with water (3×), brine and the organic extracts combined. The organic layer was dried (MgSO$_4$), filtered, and concentrated in vacuo. The resulting residue was flash chromatographed (100 g SiO$_2$, 3% diethyl ether in hexane) to provide the desired product (18.3 g, 67.8 mmol, 73% yield) which was used directly in the next reaction.

Step 6b: Preparation of racemic 2-Ethylcyclopropane-1,1-dicarboxylic acid tert-butyl ester, Shown Below

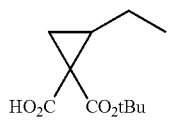

The product of Step 6a (18.3 g, 67.8 mmol) was added to a suspension of potassium tert-butoxide (33.55 g, 299.0 mmol) in dry ether (500 mL) at 0° C., followed by H$_2$O (1.35 mL, 75.0 mmol) and was vigorously stirred overnight at room temperature. The reaction mixture was poured in a mixture of ice and water and washed with ether (3×). The aqueous layer was acidified with a 10% aq. citric acid solution at 0° C. and extracted with ethyl acetate (3×). The combined organic layers were washed with water (2×), brine, dried (MgSO$_4$), filtered, and concentrated in vacuo to provide the desired product as a pale yellow oil (10 g, 46.8 mmol, 69% yield).

Step 6c: Preparation of (1R,2R)/(1S,2S)2-Ethyl-1-(2-trimethylsilanylethoxycarbonylamino)cyclopropane-carboxylic acid tert-butyl ester Shown Below

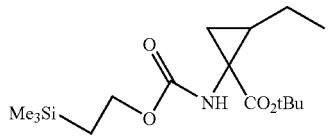

To a suspension of the product of Step 6b (10 g, 46.8 mmol) and 3 g of freshly activated 4 Å molecular sieves in dry benzene (160 mL), was added triethylamine (7.50 mL, 53.8 mmol) and DPPA (11 mL, 10.21 mmol). The reaction mixture was refluxed for 3.5 hours, 2-trimethylsilyl-ethanol (13.5 mL, 94.2 mmol) was then added, and the reaction mixture was refluxed overnight. The reaction mixture was filtered, diluted with diethyl ether, washed with a 10% aqueous citric acid solution, water, saturated aqueous NaHCO$_3$, water (2×), brine (2×), dried (MgSO$_4$), filtered, and concentrated in vacuo. The residue was suspended with 10 g of Aldrich polyisocyanate scavenger resin in 120 mL of CH$_2$Cl$_2$, stirred at room temperature overnight and filtered to provide the desired product (8 g, 24.3 mmol; 52%) as a pale yellow oil: $^1$H NMR (CDCl$_3$) δ 0.03 (s, 9H), 0.97 (m, 5H), 1.20 (bm, 1H), 1.45 (s, 9H), 1.40-1.70 (m, 4H), 4.16 (m, 2H), 5.30 (br s, 1H).

Step 6d: Preparation of racemic (1R,2R)/(1S,2S)1-Amino-2-ethylcyclopropanecarboxylic acid tert-butyl ester, Shown Below

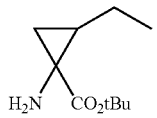

ethyl syn to carboxy

To the product of Step 6c (3 g, 9 mmol) was added a 1.0 M TBAF solution in THF (9.3 mL, 9.3 mmol) and the mixture heated to reflux for 1.5 hours, cooled to room temperature and then diluted with 500 mL of ethyl acetate. The solution was successively washed with water (2×100 mL), brine (2×100 mL), dried (MgSO$_4$), filtered, and concentrated in vacuo to provide the desired intermediate.

Section A.II: Preparation of P1 Prime Intermediates

Example 7

Cyclopropyl sulfonamide was prepared in accordance with Methods A, B and C, shown below.

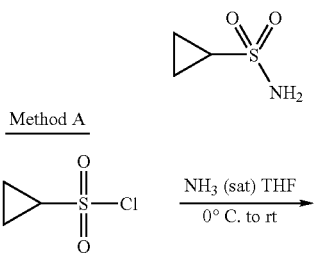

Method A

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to room temperature overnight and stirred one additional day. The mixture was concentrated until 1-2 mL of solvent remained, applied on to 30 g plug of SiO$_2$ (eluted with 30% to 60% ethyl acetate/hexanes) to provide 3.45 g (100%) of cyclopropyl sulfonamide as a white solid. $^1$H NMR (Methanol-d$_4$) δ 0.94-1.07 (m, 4H), 2.52-2.60 (m, 1H); $^{13}$C NMR (methanol-d$_4$) δ 5.92, 33.01. Anal. Calcd. For C$_3$H$_7$NO$_2$S: C, 29.74; H, 5.82; N, 11.56. Found: C, 29.99; H, 5.89, N, 11.50.

Method B

B.1) Cyclization of N-t-butyl-(3-chloro)propylsulfonamide

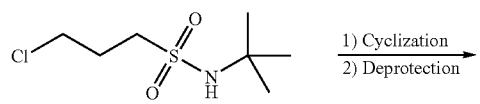

B.2) Preparation of N-tert-Butyl-(3-chloro)propylsulfonamide

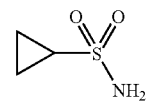

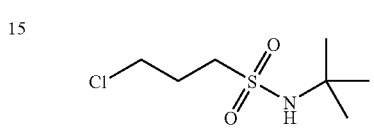

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to room temperature and stirred for 24 hours. The mixture was filtered, and the filtrate was concentrated in vacuo. The residue was dissolved in CH$_2$Cl$_2$ (2.0 L). The resulting solution was washed with 1 N HCl (1.0 L), water (1.0 L), brine (1.0 L) and dried over Na$_2$SO$_4$. The mixture was filtered and concentrated in vacuo to give a slightly yellow solid, which was crystallized from hexane to provide the product as a white solid (316.0 g, 99%). $^1$H NMR (CDCl$_3$) δ 1.38 (s, 9H), 2.30-2.27 (m, 2H), 3.22 (t, J=7.35 Hz, 2H), 3.68 (t, J=6.2 Hz, 2H), 4.35 (b, 1H).

B.3) Preparation of Cyclopropanesulfonic acid tert-butylamide

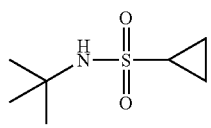

A solution of n-BuLi (86.7 mL, 138.8 mmol, 1.6 M in hexane) was dissolved in dry THF (120 mL) and cooled to −78° C. under a argon atmosphere. To this solution was added a solution of N-tert-butyl-(3-chloro)propylsulfonamide from Step B.2 (14.5 g, 67.8 mmol) in dry THF (160 mL) slowly dropwise over 60 minutes. The dry ice bath was removed and the reaction mixture was allowed to warm to room temperature over a period of 2 hours. The reaction mixture was quenched with glacial acetic acid (3.4 mL), concentrated in vacuo, and partitioned between CH$_2$Cl$_2$ (100 mL) and water (100 mL). The organic phase was washed with aqueous 1N NaOH (150 mL), brine (100 mL), dried (MgSO$_4$), filtered, and concentrated in vacuo to provide the N-tert-Butyl cyclopropylsulfonamide as a waxy off white solid (12 g, 100%): $^1$H NMR (CDCl$_3$) δ 0.98 (m, 2H), 1.17 (m, 2H), 1.38 (s, 9H), 2.45 (m, 1H), 4.45 (br s, 1H). $^{13}$C NMR (CDCl$_3$) δ 6.5, 30.6, 33.5, 54.2. MS (ESI) 176 (M$^+$–H).

B.4) Preparation of cyclopropylsulfonamide

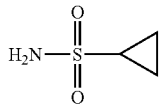

A solution of cyclopropanesulfonic acid tert-butylamide (110.0 g, 0.62 mol) in TFA (500 mL) was stirred at room temperature for 16 hours. The volatile was removed in vacuo. The residue was recrystallized from ethyl acetate/hexane (60 mL/240 mL) to provide the desired product as a white solid (68.5 g, 91%).

$^1$H NMR (DMSO-d$_6$) δ 0.84-0.88 (m, 2H), 0.95-0.98 (m, 2H), 2.41-2.58 (m, 1H), 6.56 (b, 2H).

Method C

C.1) Cyclization of N-Boc-(3-chloro)propylsulfonamide

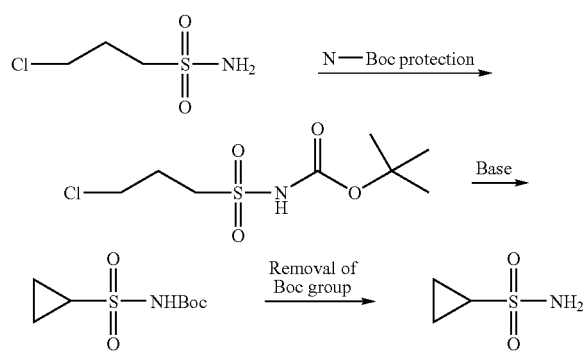

C.2) Preparation of 3-chloropropylsulfonamide

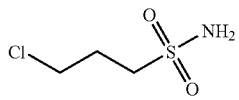

A solution of 3-chloropropanesulfonyl chloride (55 g, 310.7 mmol) was dissolved in THF (200 mL) and added dropwise over 30 minutes to a solution of NH$_4$OH (200 mL) cooled to 0° C. The reaction mixture was warmed to room temperature, stirred 1 hour, and the aqueous layer partioned multiple time with CH$_2$Cl$_2$ (4×500-mL). The combined CH$_2$Cl$_2$ layer was washed with 1 N HCl (150 mL), water (150 mL), dried over MgSO$_4$, filtered, and concentrated in vacuo. The crude solid was recrystallized from the minimum amount of CH$_2$Cl$_2$ in hexanes to provide 3-chloropropylsulfonamide as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

C.3) Preparation of 3-chloropropylsulfonylamine tert-butylcarbamate

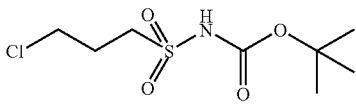

To a solution of 3-chloropropylsulfonamide (30.2 g, 191.5 mmol) (from Step C.2), triethylamine (30.2 mL, 217.0 mmol), and 4-DMAP (2.40 g, 19.6 mmol) in CH$_2$Cl$_2$ (350 mL) cooled to 0° C. was added slowly dropwise a solution of BOC$_2$O (47.2 g, 216.9 mmol) in CH$_2$Cl$_2$ (250 mL) over 30 minutes. The reaction mixture was allowed to warm to room temperature, stirred an additional 3 hours and was partioned with 1 N HCl (300 mL), water (300 mL), brine (300 mL), dried over MgSO$_4$, filtered, and concentrated in vacuo to provide the crude product. This material was triturated with 70 mL of 5% CH$_2$Cl$_2$ in hexanes to provide 3-chloropropylsulfonylamine tert-butylcarbamate as an off-white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

C.4) Preparation of cyclopropylsulfonylamine tert-butyl carbamate

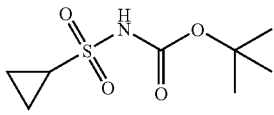

A solution of n-BuLi (74.7 mL, 119.5 mmol, 1.6 M in hexane) was dissolved in dry THF (105 mL) and cooled to −78° C. under a argon atmosphere. To this solution was added a solution of 3-chloropropylsulfonylamine tert-butylcarbamate (14 g, 54.3 mmol) (from Step C.3) in dry THF (105 mL) slowly dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between CH$_2$Cl$_2$ (100 mL) and water (100 mL). The organic phase was washed with brine (100 mL), dried (MgSO$_4$), filtered, and concentrated in vacuo to provide the cyclopropylsulfonylamine tert-butyl carbamate as a waxy off white solid (12.08 g, 100%): $^1$H NMR (CDCl₃) δ 1.10 (m, 2H), 1.34 (m, 2H), 1.50 (s, 9H), 2.88 (m, 1H), 7.43 (s, 1H). ¹³C NMR (CDCl₃) δ 6.21, 28.00, 31.13, 84.07, 149.82.

C.5) Alternative Preparation of Cyclopropylsulfonylamine tert-butyl carbamate

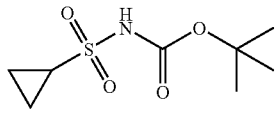

To a solution of cyclopropylsulfonamide (6.0 g, 50.0 mmol) in CH₂Cl₂ (50 mL) was added BOC₂O (13.0 g, 59.0 mmol), triethylamine (7.5 mL, 74 mmol), and 4-DMAP (0.30 g, 2.5 mmol). The reaction mixture was stirred overnight at room temperature, diluted with ethyl acetate (300 mL), partitioned with 1 N HCl (3×100 mL), dried over MgSO₄, filtered, and concentrated in vacuo to provide 9.3 g (85%) of cyclopropylsulfonylamine tert-butylcarbamate.

C.6) Preparation of cyclopropylsulfonamide from cyclopropylsulfonylamine tert-butyl carbamate

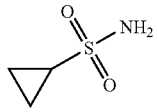

A yield of >95% was routinely obtained of cyclopropylsulfonamide following the same TFA deprotection procedure used above (Method B) for the deprotection of cyclopropanesulfonic acid tert-butylamide except that of cyclopropylsulfonylamine tert-butyl carbamate was used in place of N-tert-butyl-(1-methyl)cyclopropyl-sulfonamide.

Example 8

Substituted cycloalkylsulfonamides were prepared in accordance with Methods A and B, shown below.

Method A

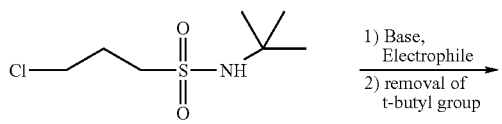

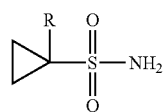

A.1) 1-methylcyclopropylsulfonamide

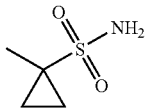

A.1.a) Preparation of N-tert-Butyl-(1-methyl)cyclopropyl-sulfonamide

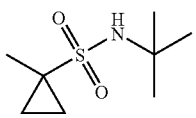

A solution of N-tert-butyl-(3-chloro)propylsulfonamide (4.3 g, 20 mmol) was dissolved in dry THF (100 mL) and cooled to −78° C. To this solution was added n-BuLi (17.6 mL, 44 mmol, 2.5 M in hexane) slowly. The dry ice bath was removed and the reaction mixture was allowed to warm to room temperature over a period of 1.5 hours. This mixture was then cooled to −78° C., and a solution of n-BuLi (20 mmol, 8 mL, 2.5 M in hexane) was added. The reaction mixture was warmed to room temperature, recooled to −78° C. over a period of 2 hours and a neat solution of methyl iodide (5.68 g, 40 mmol) added. The reaction mixture was allowed to warm to room temperature overnight, quenched with saturated NH₄Cl (100 mL) at room temperature. It was extracted with ethyl acetate (100 mL). The organic phase was washed with brine (100 mL), dried (MgSO₄), filtered, and concentrated in vacuo to give a yellow oil which was crystallized from hexane to provide the product as a slightly yellow solid (3.1 g, 81%): ¹H NMR (CDCl₃) δ 0.79 (m, 2H), 1.36 (s, 9H), 1.52 (m, 2H), 1.62 (s, 3H), 4.10 (br s, 1H).

A.1.b) Preparation of 1-methylcyclopropylsulfonamide

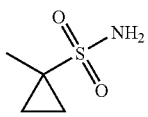

A solution of N-tert-butyl-(1-methyl)cyclopropylsulfonamide (1.91 g, 10 mmol) (Step A.1.a) was dissolved in TFA (30 mL), and the reaction mixture stirred at room temperature for 16 hours. The solvent was removed in vacuo to give a yellow oil which was crystallized from ethyl acetate/hexane (1:4, 40 mL) to yield 1-methylcyclopropylsulfonamide as a white solid (1.25 g, 96%): ¹H NMR (CDCl₃) δ 0.84 (m, 2H), 1.41

(m, 2H), 1.58 (s, 3H), 4.65 (br s, 2H). Anal. Calcd. For C₄H₉NO₂S: C, 35.54; H, 6.71; N, 10.36. Found: C, 35.67; H, 6.80; N, 10.40.

A.2) 1-Benzylcyclopropylsulfonamide

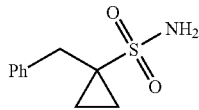

A.2.a) Preparation of N-tert-Butyl-(1-benzyl)cyclopropyl-sulfonamide

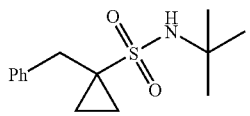

This compound was obtained in 60% yield using the procedure described for the synthesis of N-tert-butyl-(1-methyl)cyclopropylsulfonamide except 1.05 equivalents of benzyl bromide were used, followed by trituration with 10% ethyl acetate in hexane: ¹H NMR (CDCl₃) δ 0.92 (m, 2H), 1.36 (m, 2H), 1.43 (s, 9H), 3.25 (s, 2H), 4.62 (br s, 1H), 7.29-7.36 (m, 5H).

A.2.b) Preparation of 1-Benzylcyclopropylsulfonamide

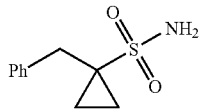

This compound was obtained in 66% yield from N-tert-butyl(1-benzyl)cyclopropylsulfonamide using the procedure described for the synthesis of 1-methylcyclopropylsulfonamide, followed by recrystallization from the minimum amount of 10% ethyl acetate in hexane: ¹H NMR (CDCl₃) δ 0.90 (m, 2H), 1.42 (m, 2H), 3.25 (s, 2H), 4.05 (s, 2H), 7.29 (m, 3H), 7.34 (m, 2H); ¹³C NMR (CDCl₃) δ 11.1, 36.8, 41.9, 127.4, 128.8, 129.9, 136.5.

A.3) 1-Propylcyclopropylsulfonamide

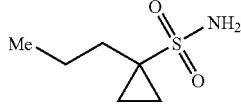

A.3.a) Preparation of N-tert-butyl-(1-benzyl)cyclopropyl-sulfonamide

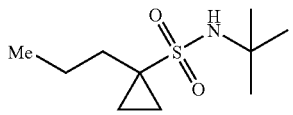

This compound was prepared using the process described for the preparation of 1-methylcyclopropylsulfonamide except propyl halide was utilized in place of methyl iodide in the second step of the process.

A.4) 1-Allylcyclopropylsulfonamide

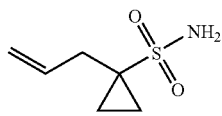

A.4.a) Preparation of N-tert-Butyl-(1-allyl)cyclopropylsulfonamide

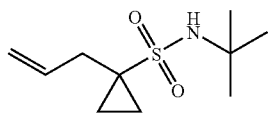

This compound, N-tert-butyl-(1-allyl)cyclopropylsulfonamide, was obtained in 97% yield according to the procedure described in the synthesis of N-tert-Butyl-(1-methyl)cyclopropylsulfonamide except 1.25 equivalents of allyl bromide were used as electrophile. The compound was taken directly into the next reaction without purification: ¹H NMR (CDCl₃) δ 0.83 (m, 2H), 1.34 (s, 9H), 1.37 (m, 2H), 2.64 (d, J=7.3 Hz, 2H), 4.25 (br s, 1H), 5.07-5.10 (m, 2H), 6.70-6.85 (m, 1H).

A.4.b) Preparation of 1-allylcyclopropylsulfonamide

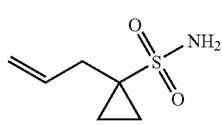

This compound, 1-allylcyclopropylsulfonamide, was obtained in 40% yield from N-tert-butyl-(1-allyl)cyclopropylsulfonamide (from Step A.4.a) according to the procedure described in the synthesis of 1-methylcyclopropylsulfonamide. The compound was purified by column chromatography over SiO₂ using 2% methanol in CH₂Cl₂ as the eluent: ¹H NMR (CDCl₃) δ 0.88 (m, 2H), 1.37 (m, 2H), 2.66 (d, J=7.0

Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

A.5) 1-(1-cyclohexenyl)cyclopropyl-sulfonamide

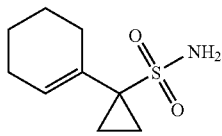

A.5.a) Preparation of N-tert-Butyl-[1-(1-hydroxy)cyclohexyl]-cyclopropylsulfonamide

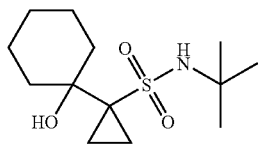

This compound was obtained in 84% yield using to the procedure described for the synthesis of N-tert-butyl-(1-methyl)cyclopropylsulfonamide except 1.30 equivalents of cyclohexanone were used, followed by recrystallization from the minimum amount of 20% ethyl acetate in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (br s, 1H), 4.55 (br s, 1H).

A.5.b) Preparation of 1-(1-cyclohexenyl)cyclopropyl-sulfonamide

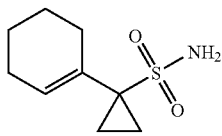

This compound, 1-(1-cyclohexenyl)-cyclopropylsulfonamide was obtained in 85% yield from N-tert-butyl-[1-(1-hydroxy)cyclohexyl]-cyclopropylsulfonamide (from Step A.5.a) using the procedure described for the synthesis of 1-methylcyclopropylsulfonamide, followed by recrystallization from the minimum amount of ethyl acetate and hexane: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$−1).

A.6) 1-benzoylcyclopronylsulfonamide

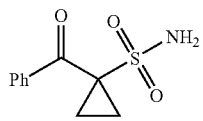

A.6.a) Preparation of N-tert-Butyl-(1-benzoyl)cyclopropyl-sulfonamide

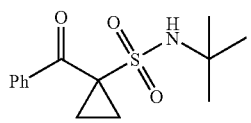

This compound was obtained in 66% yield using the procedure described for the synthesis of N-tert-butyl-(1-methyl)cyclopropylsulfonamide except 1.2 equivalents of methyl benzoate was used as the electrophile. The compound was purified by column chromatography over SiO$_2$ using 30% to 100% CH$_2$Cl$_2$ in hexane: $^1$H NMR (CDCl$_3$) δ 1.31 (s, 9H), 1.52 (m, 2H), 1.81 (m, 2H), 4.16 (br s, 1H), 7.46 (m, 2H), 7.57 (m, 1H), 8.05 (d, J=8.5 Hz, 2H).

A.6.b) Preparation of 1-benzoylcyclopropylsulfonamide

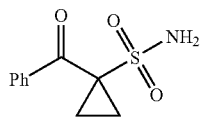

This compound was obtained in 87% yield from N-tert-butyl(1-benzoyl)cyclopropyl-sulfonamide (from Step A.6.a) using the procedure described for the synthesis of 1-methylcyclopropylsulfonamide, followed by recrystallization from the minimum amount of ethyl acetate in hexane: $^1$H NMR (DMSO-d$_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-d$_6$) δ 12.3, 48.4, 128.1, 130.0, 133.4, 135.3, 192.0.

A.7) 1-(Phenylamino-carboxy)cyclopropylsulfonamide

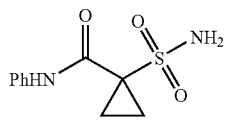

A.7.a) Preparation of N-tert-Butyl-(1-phenylaminocarboxy)-cyclopropylsulfonamide

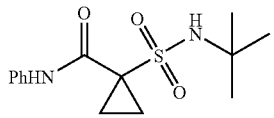

This compound was obtained in 42% yield using the procedure described for the synthesis of N-tert-butyl-(1-methyl)cyclopropylsulfonamide using 1 equivalent of phenylisocyanate, followed by recrystallization from the minimum amount of ethyl acetate in hexane $^1$H NMR (CDCl$_3$) δ 1.38 (s, 9H), 1.67-1.71 (m, 4H), 4.30 (br s, 1H), 7.10 (t, J=7.5 Hz, 1H), 7.34 (t, J=7.5 Hz, 2H), 7.53 (t, J=7.5 Hz, 2H).

A.7.b) Preparation of 1-(Phenylamino-carboxy)cyclopropylsulfonamide

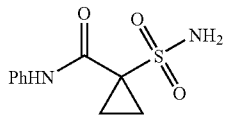

This compound 1-(phenylaminocarboxy)cyclopropylsulfonamide, was obtained in 75% yield from N-tert-butyl(1-phenylaminocarboxy)cyclopropylsulfonamide (from Step A.7.a) using the procedure described for the synthesis of 1-methylcyclopropylsulfonamide, followed by recrystallization from the minimum amount of ethyl acetate in hexane: $^1$H NMR (CDCl$_3$) δ 1.70 (m, 2H), 1.75 (m, 2H), 4.85 (s, 2H), 7.16 (t, J=7.6 Hz, 1H), 7.35 (t, J=7.6 Hz, 2H), 7.53 (d, J=8.2 Hz, 2H), 9.25 (s, 1H).

Method B: Preparation of Substituted Cycloalkylsulfonamides

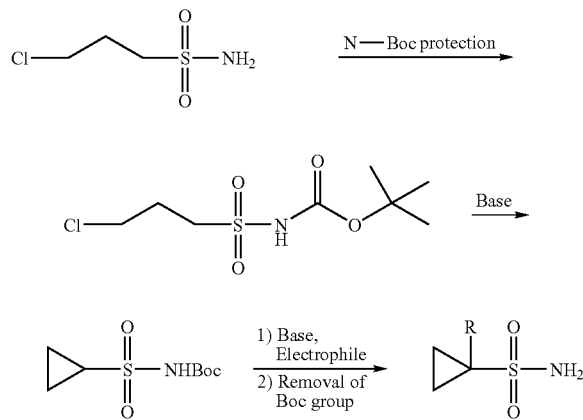

B.1) 1-methoxymethylcyclopropylsulfonamide

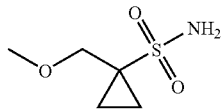

B.1.a) Preparation of 1-methoxymethylcyclopropylsulfonylamine tert-butylcarbamate

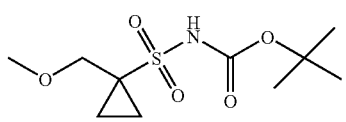

To a solution of cyclopropylsulfonylamine tert-butylcarbamate (1.0 g, 4.5 mmol) dissolved in THF (30 mL) cooled to −78° C., was added n-BuLi (6.4 mL, 10.2 mmol, 1.6 M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to provide 1-methoxy-methylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

B.1.b) Preparation of 1-methoxymethylcyclopropylsulfonamide

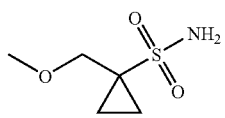

A solution of 1-methoxymethylcyclopropylsulfonylamine tert-butylcarbamate (1.14 g, 4.30 mmol) (from Step B.1.a) was dissolved in a solution of 50% TFA/CH$_2$Cl$_2$ (30 mL) and was stirred at room temperature for 16 hours. The solvent was removed in vacuo and the residue chromatographed over 80 g of SiO$_2$ (eluting with 0% to 60% ethyl acetate/hexanes to provide 1-methoxymethylcyclopropylsulfonamide as a white solid (0.55 g, 77% overall over two steps): $^1$H NMR (CDCl$_3$)

δ 0.95 (m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$).

B.2) 1-cyclopropylmethylcyclopropylsulfonamide

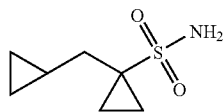

B.2.a) Preparation of 1-cyclopropylmethylcyclopropylsulfonylamine tert-butylcarbamate

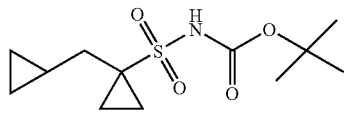

This compound was obtained in 92% yield according to the procedure described in the synthesis of 1-methoxymethylcyclopropylsulfonylamine tert-butylcarbamate (Step B.1.a) except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

B.2.b) Preparation of 1-cyclopropylmethylcyclopropylsulfonamide

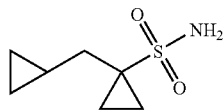

This compound was obtained in 65% yield from 1-cyclopropylmethylcyclopropylsulfonylamine tert-butylcarbamate (from Step B.2.a) according to the procedure described for the synthesis of 1-methoxymethylcyclopropylsulfonamide (Step B.1.b). The compound was purified by column chromatography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

B.3) 1-propylcarbamoylcyclopropanesulfonamide

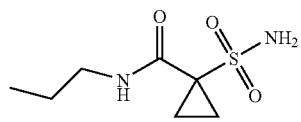

B.3.a) Preparation of 1-propylcarbamoylcyclopropanesulfonamide tert-butylcarbamate

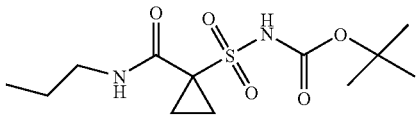

This compound was obtained in a crude 100% yield according to the procedure described for the synthesis of 1-methoxymethylcyclopropylsulfonylamine tert-butylcarbamate (Step B.1.a) except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

B.3.b) Preparation of 1-propylcarbamoylcyclopropanesulfonamide

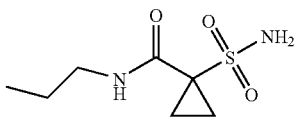

This compound was obtained in an optimized 50% yield from 1-propylcarbamoylcyclopropanesulfonamide tert-butylcarbamate (from Step B.3.a) according to the procedure described for the synthesis of 1-methoxymethylcyclopropylsulfonamide (Step B.1.b), except that no chromatography was used as the material was recrystallized from the minimum amount of CH$_2$Cl$_2$/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

B.4) 1-(3,5-dimethylisoxazol-4yl)carbamoylcyclopropanesulfonamide

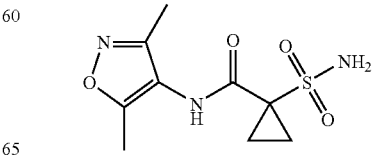

B.4.a) Preparation of 1-(3,5-dimethylisoxazol-4-yl) carbamoylcyclopropanesulfonamide tert-butylcarbamate

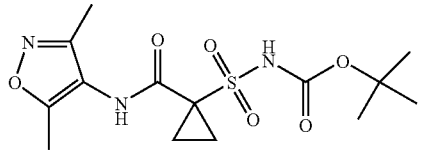

This compound was obtained in a crude 100% yield according to the procedure described for the synthesis of 1-methoxymethylcyclopropylsulfonylamine tert-butylcarbamate (Step B.1.a) except that 1.20 equivalents of 3,5-dimethylisoxazole-4-isocyanate was used as the electrophile. The compound was taken directly into the next reaction without purification.

B.4.b) Preparation of 1-(3,5-dimethylisoxazol-4yl) carbamoylcyclopropanesulfonamide

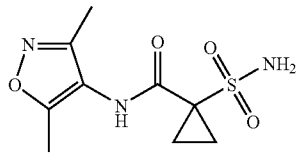

This compound was obtained in 50% yield (580 mg) from 1.62 g (4.52 mmol) of 1-(3,5-dimethylisoxazol-4-yl)carbamoylcyclo-propanesulfonamide tert-butylcarbamate (from Step B.4.a) using 30 mL (120 mmol) of 4N HCl/dioxanes, stirring overnight, concentration and chromatography over a Biotage 40M column (eluting with 0% to 5% methanol/ $CH_2Cl_2$: $^1H$ NMR (methanol-$d_4$) δ 1.57 (m, 2H), 1.61 (m 2H), 2.15 (s, 3H), 2.30 (s, 3H), 4.84 (s, 3H); $^{13}C$ NMR (methanol-$d_4$) δ 9.65, 10.94, 15.01, 46.11, 114.82, 159.45, 165.55, 168.15; LRMS m/z 260 ($M^++H$).

Examples 9-14

Cycloalkyl (and alkyl) sulfonamides were prepared from cyloalkyl (and alkyl) bromides.

Example 9

Preparation of cyclobutylsulfonamide from cylobutylbromide

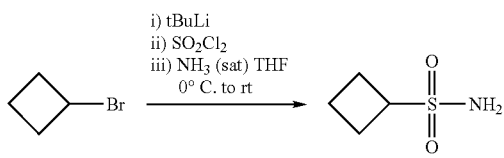

To a solution of 5.0 g (37.0 mmol) of cyclobutyl bromide in 30 mL of anhydrous diethyl ether (diethyl ether) cooled to –78° C. was added 44 mL (74.8 mmol) of 1.7M tert-butyl lithium in pentanes and the solution slowly warmed to –35° C. over 1.5 hours. This mixture was cannulated slowly into a solution of 5.0 g (37.0 mmol) of freshly distilled sulfuryl chloride in 100 mL of hexanes cooled to –40° C., warmed to 0° C. over 1 hour and carefully concentrated in vacuo. This mixture was redissolved in diethyl ether, washed once with some ice-cold water, dried ($MgSO_4$) and concentrated carefully. This mixture was redissolved in 20 mL of THF, added dropwise to 500 mL of saturated $NH_3$ in THF and was allowed to stir overnight. The mixture was concentrated in vacuo to a crude yellow solid and was recrystallized from the minimum amount of $CH_2Cl_2$ in hexanes with 1-2 drops of methanol to provide 1.90 g (38%) of cyclobutylsulfonamide as a white solid. $^1H$ NMR ($CDCl_3$) δ 1.95-2.06 (m, 2H), 2.30-2.54 (m, 4H), 3.86 (p, J=8 Hz, 1H), 4.75 (br s, 2H); $^{13}C$ NMR ($CDCl_3$) δ 16.43, 23.93, 56.29. HRMS m/z (M–H)$^-$ calcd for $C_4H_8NSO_2$: 134.0276, found 134.0282.

Example 10

Preparation of cyclopentyl sulfonamide

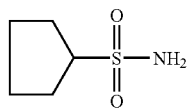

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to –78° C. The mixture was warmed to 0° C. over 1 hour and was then carefully concentrated in vacuo. This mixture was redissolved in diethyl ether (200 mL), washed once with some ice-cold water (200 mL), dried ($MgSO_4$), filtered, and concentrated carefully. This mixture was redissolved in 35 mL of THF, added dropwise to 500 mL of saturated $NH_3$ in THF and was allowed to stir overnight. The mixture was concentrated in vacuo to a crude yellow solid, the residue filtered through 50 g of silica gel using 70% ethyl acetate-hexanes as the eluent and the solution was then concentrated. The residue was recrystallized from the minimum amount of $CH_2Cl_2$ in hexanes with 1-2 drops of methanol to provide 2.49 g (41%) of cyclopentylsulfonamide as a white solid. $^1H$ NMR ($CDCl_3$) δ 1.58-1.72 (m, 2H), 1.74-1.88 (m, 2H), 1.94-2.14 (m, 4H), 3.48-3.59 (m, 1H), 4.80 (br s, 2H); $^{13}C$ NMR ($CDCl_3$) δ 25.90, 28.33, 63.54; MS m/e 148 (M–H)$^-$.

Example 11

Preparation of cyclohexyl sulfonamide

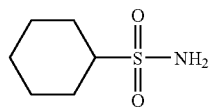

A solution of 18.5 mL (37.0 mmol) of 2M cyclohexylmagnesium chloride (TCI Americas) in diethyl ether was added dropwise to a solution of 3.0 mL (37.0 mmol) freshly distilled sulfuryl chloride in 100 mL of hexanes cooled to –78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and was concentrated. The residue was recrystallized from the minimum amount of CH$_2$Cl$_2$ in hexanes with 1-2 drops of methanol to provide 1.66 g (30%) of cyclohexylsulfonamide as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (br s, 2H); $^{13}$$^C$H NMR (CDCl$_3$) δ 25.04, 25.04, 26.56, 62.74; MS m/e 162 (M-1)$^-$.

Example 12

Preparation of neopentylsulfonamide

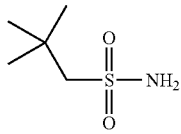

Following the procedure for the preparation of cyclohexyl sulfonamide, 49 mL (37 mmol) of 0.75M neopentylmagnesium chloride (Alfa) in ether was converted to 1.52 g (27%) of neopentylsulfonamide as a white solid. $^1$H NMR (CDCl$_3$) δ 1.17 (s, 9H), 3.12 (s, 2H), 4.74 (br s, 2H); $^{13}$C NMR (CDCl$_3$) δ 29.46, 31.51, 67.38; MS m/e 150 (M-1)$^-$.

Example 13

Preparation of cyclobutylcarbinyl-sulfonamide

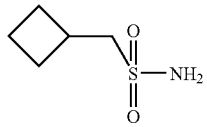

A solution of 12.3 g (83 mmol) of cyclobutylcarbinyl bromide (Aldrich) and 13.7 g (91 mmol) of sodium iodide in 150 mL of acetone was refluxed overnight and then cooled to room temperature. The inorganic solids were filtered off and the acetone and cyclopropylcarbinyl iodide (8.41 g, 46%) distilled off at ambient and 150 torr at 80° C., respectively.

A solution of 4.0 g (21.98 mmol) of cyclobutylcarbinyl iodide in 30 mL of anhydrous diethyl ether (diethyl ether) cooled to –78° C. was cannulated into a solution of 17 mL (21.98 mmol) of 1.3M sec-butyl lithium in cyclohexanes and the solution was stirred for 5 minutes. To this mixture was cannulated a solution of 3.0 g (21.98 mmol) of freshly distilled sulfuryl chloride in 110 mL of hexanes cooled to –78° C., the mixture warmed to room temperature over 1 hour and was then carefully concentrated in vacuo. This mixture was redissolved in diethyl ether, washed once with some ice-cold water, dried (MgSO$_4$), filtered, and concentrated carefully. This mixture was redissolved in 30 mL of THF, added dropwise to 500 mL of saturated NH$_3$ in THF and was allowed to stir overnight. The mixture was concentrated in vacuo to a crude yellow solid and was recrystallized from the minimum amount of CH$_2$Cl$_2$ in hexanes with 1-2 drops of methanol to provide 1.39 g (42%) of cyclobutyl carbinylsulfonamide as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2H), 4.74 (br s, 2H); $^{13}$C NMR (CDCl$_3$) δ 19.10, 28.21, 30.64, 60.93; MS m/e 148 (M-1)$^-$. (Retention time: 1.73, method B), 818 (M$^+$+H)

Example 14

Preparation of cyclopropylcarbinyl-sulfonamide

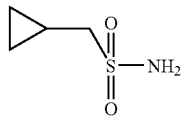

Using the procedure employed for the preparation of cyclobutylcarbinylsulfonamide, cyclopropylcarbinylsulfonamide was prepared from cyclopropylcarbinyl bromide (Aldrich) (see also JACS 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (br s, 2H); $^{13}$C NMR (CDCl$_3$) δ 4.33, 5.61, 59.93; MS m/e 134 (M-1).

Example 14.1

General Procedure for the Preparation of Sulfamides

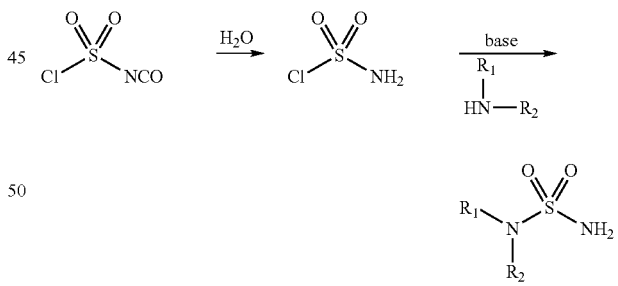

The intermediate sulfamoyl chloride was prepared by addition of water (1 equiv) in THF to a cold (–20° C.) stirred solution of chlorosulfonyl isocyanate (1 equiv) in THF and the resulting solution allowed to warm to 0° C. To this solution was added anhydrous Et$_3$N (1 equiv) followed by requisite secondary amine (1 equiv). The reaction mixture was warmed to room temperature, then filtered and the filtrate was rotary evaporated to afford the desired sulfamides. Said sulfamide was then coupled to a carboxylic acid to provide the desired acylsulfamide.

Specific Procedure for the Preparation of an Acylsulfamide Intermediate

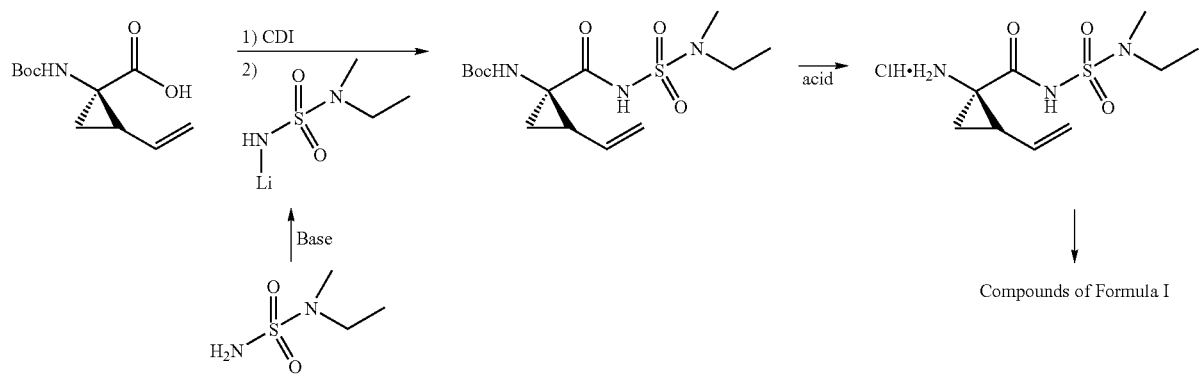

To a solution of (1R,2S) 1-tert-butoxycarbonylamino-2-vinyl-cyclopropanecarboxylic acid (217 mg, 1.194 mmol) in THF (5 mL), CDI (290 mg, 1.791 mmol) was added and the reaction mixture was heated under reflux for 45 min. In another round-bottomed flask, LiHMDS (1.0 M solution in hexanes, 2.4 mL, 2.4 mmol) was added to a solution of N-ethylmethylsulfamide (330 mg, 2.388 mmol) in THF (5 mL) and the reaction mixture was stirred at rt for 1 h. Two reaction mixtures were added together and stirred at rt for 2 h. Water was added to quench the reaction and the reaction solution was extracted with EtOAc. The oraganic layer was separated and dried over $MgSO_4$. Evaporation of solvent gave crude product which was purified by Prep. HPLC to afford desired N-acylsulfamide. N-acylsulfamide was then dissolved in 4N HCl solution in dioxane (2 mL) and stirred at rt for 4 h. Evaporation of solution give brownish oil as HCl salt. (112 mg, 33% yield). $^1$H NMR (400 Mz, $CD_3OD$) δ 1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H).

LC-MS (retention time: 0.883 min.), MS m/z 270 (M+Na$^+$).

Section B: Preparation of Compounds of Formula (I)

It should be noted that in some examples the compounds of Formula (I) that are prepared using a homochiral P1 amino acid fragment. This amino acid fragment was isolated in homochiral form from the corresponding racemate using chiral chromatography as described herein. It should be noted that each enantiomer from the resolved P1 amino acid racemate is converted to a compound of Formula (I) in the sections outlined below.

It should also be noted that in some examples the compounds of Formula (I) are prepared using a racemic mixture of the P1 amino acid fragment. In these examples the compounds of Formula (I) are generated as a mixture of diastereoisomers epimeric at the contiguous chiral centers present in the P1 amino acid fragment as noted herein. The present disclosure encompasses all diastereomers and enantiomers of the compounds of Formula (I).

Scheme 1

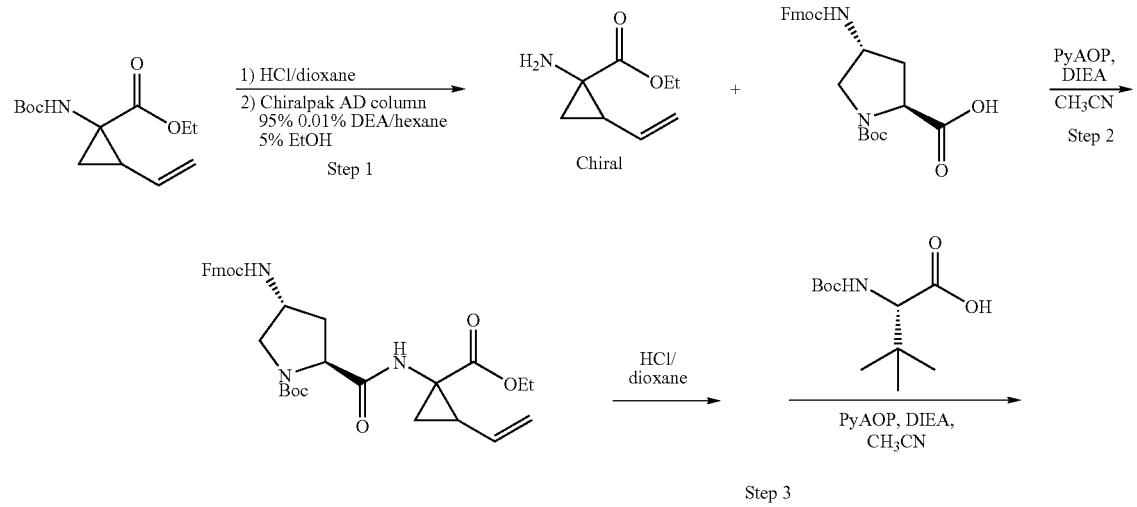

Step 3

-continued
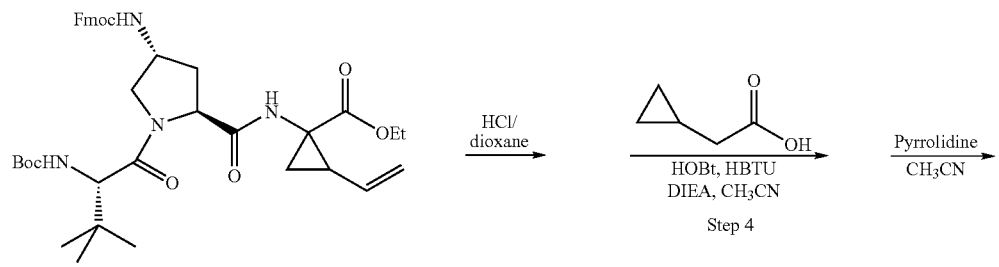
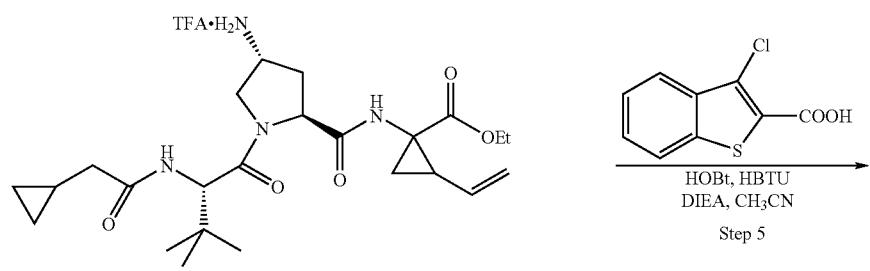
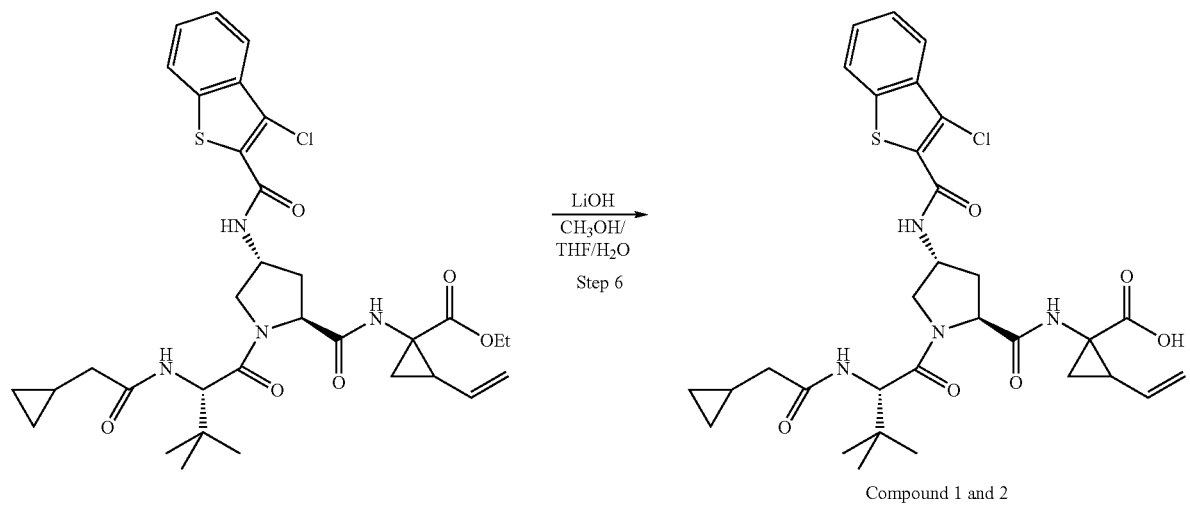
Compound 1 and 2

Examples 15 and 16

Compound 1 and Compound 2 were prepared as follows.

Compound 1 and 2

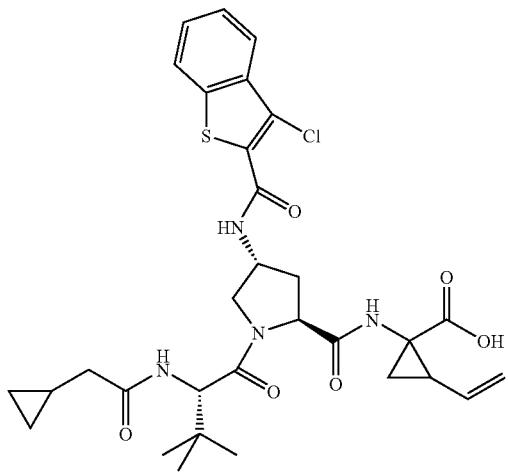

Step 1: Preparation of the racemic 1-amino-2-vinylcyclopropane carboxylic acid ethyl ester hydrochloride and the Separation of the Two Enantiomers

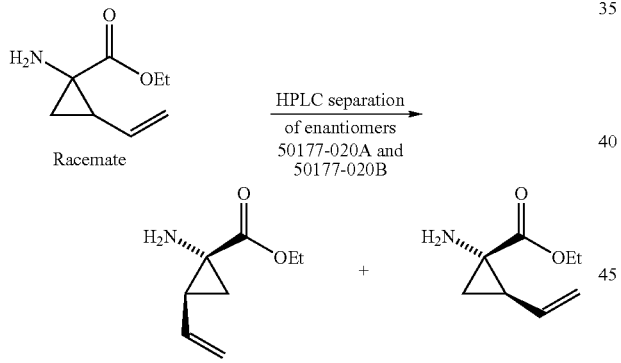

Boc-1-amino-2-vinylcyclopropane carboxylic acid ethyl ester (1.50 g, 5.88 mmol) was dissolved in 4N HCl/dioxane (10 mL, 40 mmol) and was stirred overnight at room temperature. The reaction mixture was concentrated to supply racemic 1-amino-2-vinylcyclopropane carboxylic acid ethyl ester hydrochloride as a brownish oil (1.04 g, 92%). The two enantiomers were then separated by chiral HPLC. Conditions: Chiralpak AD column, 50×500 mm, 20 μM; 95% 0.01% DEA/hexane:5% ethanol as solvent; flow rate:75 mL/min; stop time:45 min; abs=207 nm; maximum load: 300 mg. After separation, 210 mg of enantiomer 50177-020A (retention time=25 min) and 235 mg of enantiomer 50177-020B (retention time=32 min) were collected. 50177-020: $^1$H NMR(DMSO-d$_6$, 500 MHz) δ 8.80(s, br, 3H), 5.64 (m, 1H), 5.38 (d, J=17.1 Hz, 1H), 5.21(d, J=10.4 Hz, 1H), 4.21 (m, 2H), 2.34 (m, 1H), 1.68(m, 2H), 1.23 (t, J=7.2 Hz, 3H).; LC-MS (retention time 0.64 min), MS m/z 156(MH$^+$).

Step 2: 2-(1-Ethoxycarbonyl-2-vinyl-cyclopropylcarbamoyl)-4-(9H-fluoren-9-yl-methoxycarbonylamino)-pyrrolidine-1-carboxylic acid tert-butyl ester)

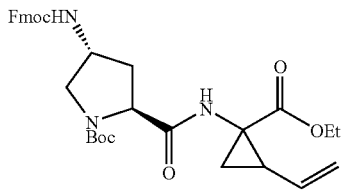

To a solution of Fmoc(2S,4R)-4-amino-1-boc-pyrrolidine-2-carboxylic acid (0.453 g, 1 mmol) in acetonitrile (10 mL), enantiomer 50177-020A (0.2 g, 1.29 mmol), DIEA (0.26 mL, 1.5 mmol) and coupling reagent PyAOP (0.78 g, 1.5 mmol) were added. The reaction mixture was stirred at room temperature for overnight. Then it was concentrated, washed with water and extracted with ethyl acetate twice. The organic layers were combined and washed with brine, and dried over MgSO$_4$, and filtered. Evaporation of solvent gave a yellowish oil which was then purified by flash column chromatography (silica gel, 3:1 ethyl acetate:hexanes) to provide a colorless oil as a single diastereoisomer. 50177-024A (0.528 g, 90% yield): $^1$H NMR(CD$_3$OD, 500 MHz) δ 7.79 (d, J=7.3 Hz, 2H), 7.64 (d, J=7.6 Hz, 2H), 7.39 (m, 2H), 7.31 (m, 2H), 5.74 (m, 1H), 5.30 (d, J=17.1 Hz, 1H), 5.11(d, J=10.4 Hz, 1H), 4.38 (m, 2H), 4.0-4.3 (m, 6H), 3.77 (m, 1H), 2.15-2.25 (m, 3H), 1.75 (m, 1H), 1.42-1.46 (m, 9H), 1.30(m, 1H), 1.22(t, J=7.0 Hz, 3H). LC-MS (retention time: 1.803 minutes.), MS m/z 590 (MH$^+$). The above procedure was repeated using enantiomer 50177-020 B in place of enantiomer 50177-020 A to provide, as a single diastereoisomer, 50177-024B (0.43 g, 73% yield): $^1$H NMR(CD$_3$OD, 500 MHz) δ 7.79 (d, J=7.6 Hz, 2H), 7.64 (d, J=7.6 Hz, 2H), 7.39 (m, 2H), 7.31 (m, 2H), 5.73 (m, 1H), 5.30 (dd, J=17.1 Hz, 1.5 Hz, 1H), 5.10(m, 1H), 4.38 (m, 2H), 4.0-4.3 (m, 6H), 3.73 (m, 1H), 2.10-2.25 (m, 3H), 1.8 (m, 1H), 1.41-1.45 (m, 9H), 1.40(m, 1H), 1.22(m, 3H). LC-MS (retention time: 1.800 minutes.), MS m/z 590 (MH$^+$).

Step 3: 1-{[1-(2-tert-Butoxycarbonylamino-3,3-dimethylbutyryl)-4-(9H-fluoren-9-ylmethoxycarbonylamino)-pyrrolidine-2-carbonyl]-amino}-2-vinyl-cyclopropane-carboxylic acid ethyl ester

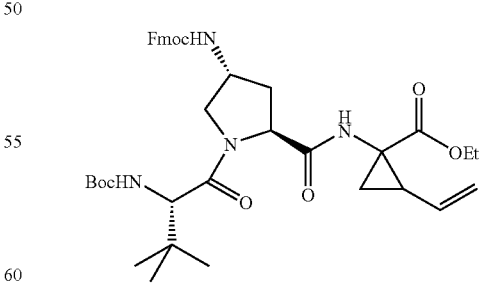

Preparation of 50177-026 50177-027

To 50177-024A (0.52 g, 0.882 mmol), 4N HCl in dioxane (3 mL) was added. The reaction mixture was stirred at room temperature for 4 hours. Then it was concentrated and acetonitrile (10 mL) was added. N-Boc-tert-leucine (0.245 g, 1.058 mmol), DIEA (0.38 mL, 2.205 mmol) and PyAOP (0.69 g, 1.323 mmol) were added. The reaction mixture was stirred at room temperature for overnight. Then it was concentrated, washed with water and extracted with ethyl acetate twice. The organic layers were combined and washed with brine, and dried over MgSO$_4$, and filtered. Evaporation of solvent gave a yellowish oil which was then purified by flash column chromatography (silica gel, 2:1 ethyl acetate:hexanes) to provide a colorless oil as pure compound (0.508 g, 82% yield). 50177-026: $^1$H NMR(CDCl$_3$, 300 MHz) δ 7.76 (d, J=7.3 Hz, 2H), 7.59-7.66(m, 3H), 7.39 (t, J=7.3 Hz, 2H), 7.30 (m, 2H), 6.13 (m, 1H), 5.74 (m, 1H), 5.28 (dd, J=17.5 Hz, 1.8 Hz, 1H), 5.13(m, 2H), 4.67 (m, 1H), 4.33 (m, 2H), 4.0-4.2 (m, 5H), 3.67 (m, 1H), 2.69 (m, 1H), 2.23 (m, 1H), 2.10 (m, 1H), 1.85 (dd, J=8.4 Hz, 5.5 Hz, 1H), 1.41 (s, 9H), 1.39(m, 1H), 1.20(t, J=7.3 Hz, 3H), 1.06(s, 9H). LC-MS (retention time: 1.990 minutes.), MS m/z 703 (MH$^+$).

To 50177-024B (0.43 g, 0.729 mmol), 4N HCl in dioxane (3 mL) was added. The reaction mixture was stirred at room temperature for 4 hours. Then it was concentrated and acetonitrile (10 mL) was added. N-Boc-tert-leucine (0.202 g, 0.875 mmol), DIEA (0.32 mL, 1.823 mmol) and PyAOP (0.57 g, 1.094 mmol) were added. The reaction mixture was stirred at room temperature for overnight. Then it was concentrated, washed with water and extracted with ethyl acetate twice. The organic layers were combined and washed with brine, and dried over MgSO$_4$ and filtered. Evaporation of solvent gave a yellowish oil which was then purified by flash column chromatography (silica gel, 2:1 ethyl acetate:hexanes) to provide a colorless oil as pure compound (0.47 g, 92% yield). 50177-027: $^1$H NMR(CDCl$_3$, 500 MHz) δ 7.76 (d, J=7.6 Hz, 2H), 7.62 (d, J=7.3 Hz, 1H), 7.58 (d, J=7.3 Hz, 1H), 7.47(s, 1H), 7.39 (t, J=7.6 Hz, 2H), 7.30 (t, J=7.3 Hz, 2H), 6.05 (m, 1H), 5.73 (m, 1H), 5.26 (d, J=17.1 Hz, 1H), 5.12(m, 2H), 4.68 (m, 1H), 4.35 (m, 2H), 4.0-4.2 (m, 5H), 3.66 (m, 1H), 2.67 (m, 1H), 2.26 (m, 1H), 2.05 (m, 1H), 1.88 (dd, J=8.2 Hz, 5.8 Hz, 1H), 1.43 (m, 1H), 1.41 (s, 9H), 1.22(t, J=7.3 Hz, 3H), 1.03(s, 9H). LC-MS (retention time: 1.970 minutes.), MS m/z 703 (MH$^+$).

Step 4: 1-({4-Amino-1-[2-(2-cyclopropyl-acetylamino)-3,3-dimethyl-butyryl]-pyrrolidine-2-carbonyl}-amino)-2-vinyl-cyclopropanecarboxylic acid ethyl ester

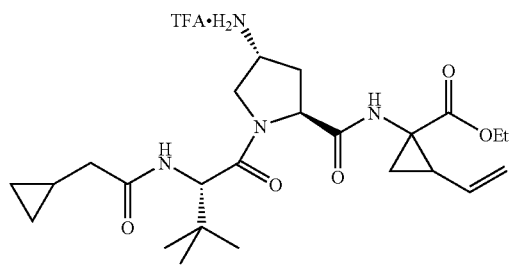

Preparation of 50177-028 50177-029

To 50177-026 (0.506 g, 0.72 mmol), 4N HCl in dioxane (3 mL) was added. The reaction mixture was stirred at room temperature for 4 hours. Then it was concentrated and acetonitrile (10 mL) was added. Cyclopropylacetic acid (0.108 g, 1.08 mmol), DIEA (0.63 mL, 3.6 mmol) and coupling reagent HOBt (0.165 g, 1.08 mmol) and HBTU (0.41 g, 1.08 mmol) were added. The reaction mixture was stirred at room temperature for overnight. Then it was concentrated, washed with water and extracted with ethyl acetate twice. The organic layers were combined and washed with brine, and dried over MgSO$_4$ and filtered. Evaporation of solvent gave a yellowish oil which was then dissolved in acetonitrile (10 mL). Pyrrolidine (1.5 mL) was added. The reaction mixture was stirred at room temperature for overnight. Then it was concentrated and the residue was purified by Prep. HPLC column to provide yellowish oil as TFA salt (0.3 g, 72% yield. 50177-028: $^1$H NMR(CD$_3$OD, 500 MHz) δ 8.76 (s, 1H), 7.89 (d, J=7.3 Hz, 1H), 5.78 (m, 1H), 5.26 (dd, J=17.1 Hz, 1.8 Hz, 1H), 5.10 (dd, J=10.1 Hz, 1.8 Hz, 1H), 4.61 (m, 1H), 4.42 (m, 1H), 4.05-4.16 (m, 5H), 2.40 (m, 1H), 2.30 (m,1H), 2.1-2.2 (m, 3H), 1.71 (dd, J=8.2 Hz, 5.2 Hz, 1H), 1.41 (dd, J=9.8 Hz, 5.2 Hz, 1H), 1.23(t, J=7.0 Hz, 3H), 1.08(s, 9H), 1.01 (m, 1H), 0.53(m, 2H), 0.20 (m, 2H). LC-MS (retention time: 1.357 minutes.), MS m/z 463 (MH$^+$).

To 50177-027 (0.47 g, 0.67 mmol), 4N HCl in dioxane (3 mL) was added. The reaction mixture was stirred at room temperature for 4 hours. Then it was concentrated and acetonitrile (10 mL) was added. Cyclopropylacetic acid (0.1 g, 1.0 mmol), DIEA (0.58 mL, 3.35 mmol) and coupling reagent HOBt (0.153 g, 1.0 mmol) and HBTU (0.38 g, 1.0 mmol) were added. The reaction mixture was stirred at room temperature for overnight. Then it was concentrated, washed with water and extracted with ethyl acetate twice. The organic layers were combined and washed with brine, and dried over MgSO$_4$ and filtered. Evaporation of solvent gave a yellowish oil which was then dissolved in acetonitrile (10 mL). Pyrrolidine (1.5 mL) was added. The reaction mixture was stirred at room temperature for overnight. Then it was concentrated and the residue was purified by Prep. HPLC column to provide yellowish solid as TFA salt (0.33 g, 85% yield). 50177-029: $^1$H NMR(CD$_3$OD, 500 MHz) δ 8.93 (s, 1H), 7.89 (d, J=7.3 Hz, 1H), 5.72 (m, 1H), 5.30 (dd, J=17.1 Hz,1.5 Hz, 1H), 5.11 (dd, J=10.4 Hz, 1.8 Hz,1H), 4.59 (m, 1H), 4.41 (m, 1H), 4.02-4.18 (m, 5H), 2.43 (m, 1H), 2.30 (m, 1H), 2.15-2.25 (m, 3H), 1.81 (dd, J=7.6 Hz, 5.2 Hz, 1H), 1.41 (dd, J=9.5 Hz, 5.5 Hz, 1H), 1.23(t, J=7.0 Hz, 3H), 1.06(s, 9H), 1.01 (m, 1H), 0.52(m, 2H), 0.19 (m, 2H). LC-MS (retention time: 1.327 minutes.), MS m/z 463 (MH$^+$).

Step 5: 1-({4-[(3-Chloro-benzo[b]thiophene-2-carbonyl)-amino]-1-[2-(2-cyclopropyl-acetylamino)-3,3-dimethy-1-butyryl]-pyrrolidine-2-carbonyl}-amino)-2-vinyl-cyclopropanecarboxylic acid ethyl ester

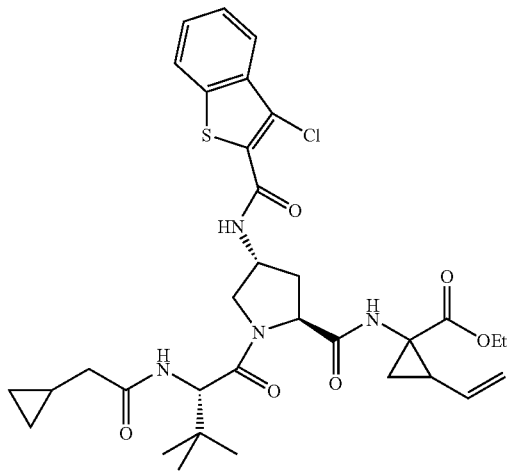

To a solution of 50177-028 (or 50177-029)(115 mg, 0.2 mmol) in acetonitrile (10 mL), 3-chlorobenzo[b]thiophene-2-carboxylic acid (63.8 mg, 0.3 mmol), DIEA (0.175 mL, 1.0 mmol) and coupling reagent HOBt (46 mg, 0.3 mmol) and HBTU (114 mg, 0.3 mmol) were added. The reaction mixture was stirred at room temperature for overnight. Then it was concentrated, washed with water and extracted with ethyl acetate twice. The organic layers were combined and washed with brine, and dried over MgSO$_4$ and filtered. Evaporation of solvent gave a yellowish oil which was purified by Prep. HPLC column to give pure compound. 50177-031A(light yellowish oil, 90 mg, 68% yield): $^1$H NMR(CD$_3$OD, 500 MHz) δ 8.70 (s, 1H), 8.44 (d, J=4.6 Hz, 1H), 7.94 (m, 1H), 7.90 (m, 1H), 7.74 (d, J=7.9 Hz, 1H), 7.55(m, 2H), 5.78 (m, 1H), 5.27 (d, J=16.8 Hz, 1H), 5.09 (d, J=10.4 Hz, 1H), 4.79 (m, 1H), 4.59 (t, J=7.4 Hz, 1H), 4.54 (d, J=7.9 Hz, 1H), 4.04-4.24 (m, 4H), 2.44 (m, 1H), 2.33 (m, 1H), 2.19 (m, 1H), 2.12 (m, 2H), 1.71 (m, 1H), 1.42 (dd, J=9.2 Hz, 5.2 Hz, 1H), 1.25 (t, J=7.0 Hz, 3H), 1.09 (s, 9H), 1.01 (m, 1H), 0.42 (m, 2H), 0.12 (m, 2H). LC-MS (retention time: 1.747 minutes.), MS m/z 657 (MH$^+$).

The above procedure was repested using 50177-029 in place of 50177-028 to provide 50177-031B as a yellowish oil, 84 mg, 64% yield: $^1$H NMR(CD$_3$OD, 500 MHz) δ 8.87 (s, 1H), 8.44 (d, J=6.1 Hz, 1H), 7.94 (m, 1H), 7.89 (m, 1H), 7.73 (d, J=7.9 Hz, 1H), 7.55(m, 2H), 5.72 (m, 1H), 5.30 (d, J=16.8 Hz, 1H), 5.10 (d, J=10.4 Hz, 1H), 4.77 (m, 1H), 4.57 (t, J=7.4 Hz, 1H), 4.53 (m, 1H), 4.05-4.25 (m, 4H), 2.49 (m, 1H), 2.37 (m, 1H), 2.21 (m, 1H), 2.12 (dd, J=7.0 Hz, 2.8 Hz, 2H), 1.81 (dd, J=7.6 Hz, 5.2 Hz, 1H), 1.45 (dd, J=9.2 Hz, 5.2 Hz, 1H), 1.26 (t, J=7.3 Hz, 3H), 1.08 (s, 9H), 0.91 (m, 1H), 0.43(m, 2H), 0.13 (m, 2H). LC-MS (retention time: 1.747 minutes.), MS m/z 657 (MH$^+$).

Step 6: 1-({4-[(3-Chloro-benzo[b]thiophene-2-carbonyl)-amino]-1-[2-(2-cyclopropyl-acetylamino)-3,3-dimethyl-butyryl]-pyrrolidine-2-carbonyl}-amino)-2-vinyl-cyclopropanecarboxylic acid To a solution of 50177-031A (100 mg, 0.152 mmol) in THF (5 mL), methanol (2.7 mL) and water (0.7 mL) mixture, lithium hydroxide monohydrate (96 mg, 2.28 mmol) was added. The reaction mixture was stirred at room temperature for overnight. Then it was acidified with 1N HCl solution and concentrated. The residue was washed with water and collected as an off-white solid (75 mg, 78% yield). Compound 1 (50177-047): $^1$H NMR(CD$_3$OD, 300 MHz) δ 7.93 (m, 1H), 7.90 (m, 1H), 7.74 (d, J=8.4 Hz, 1H), 7.55 (m, 2H), 5.83 (m, 1H), 5.27 (d, J=16.5 Hz, 1H), 5.09 (dd, J=10.6 Hz, 2.2 Hz, 1H), 4.76 (m, 1H), 4.60 (t, J=7.3 Hz, 1H), 4.53 (d, J=8.1 Hz, 1H), 4.02-4.15 (m, 2H), 2.39 (m, 2H), 2.17 (m, 1H), 2.11 (d, J=7.0 Hz, 2H), 1.70 (dd, J=8.1 Hz, 5.1 Hz, 1H), 1.42 (dd, J=9.5 Hz, 5.1 Hz, 1H), 1.06 (s, 9H), 0.90 (m, 1H), 0.41 (m, 2H), 0.11 (m, 2H).): LC-MS (retention time: 1.463 minutes.), MS m/z 629 (MH$^+$).

To a solution of 50177-031B (101 mg, 0.154 mmol) in THF (5 mL), methanol (2.7 mL) and water (0.7 mL) mixture, lithium hydroxide monohydrate (97 mg, 2.3 mmol) was added. The reaction mixture was stirred at room temperature for overnight. Then it was acidified with 1N HCl solution and concentrated. The residue was washed with water and collected as an off-white solid (94 mg, 97% yield). Compound 2 (50177-042): $^1$H NMR(CD$_3$OD, 500 MHz) δ:8.82 (s, 1H), 8.42 (m, 1H), 7.94 (m, 1H), 7.89 (m, 1H), 7.55 (m, 2H), 5.77 (m, 1H), 5.30 (dd, J=17.1 Hz, 1.5 Hz, 1H), 5.10 (dd, J=10.4 Hz, 1.5 Hz, 1H), 4.76 (m, 1H), 4.58 (m, 1H), 4.53 (m, 1H), 4.12 (m, 1H), 4.06 (m, 1H), 2.48 (m, 1H), 2.39 (m, 1H), 2.20 (m, 1H), 2.11 (dd, J=7.0 Hz, 3.1 Hz, 2H), 1.79 (dd, J=7.5 Hz, 5.2 Hz, 1H), 1.45 (dd, J=9.5 Hz, 4.9 Hz, 1H), 1.07 (s, 9H), 0.91 (m, 1H), 0.42 (m, 2H), 0.12 (m, 2H). LC-MS (retention time: 1.633 minutes.), MS m/z 629 (MH$^+$).

Examples 17 and 18

Compounds 3 and 4 were prepared as follows.

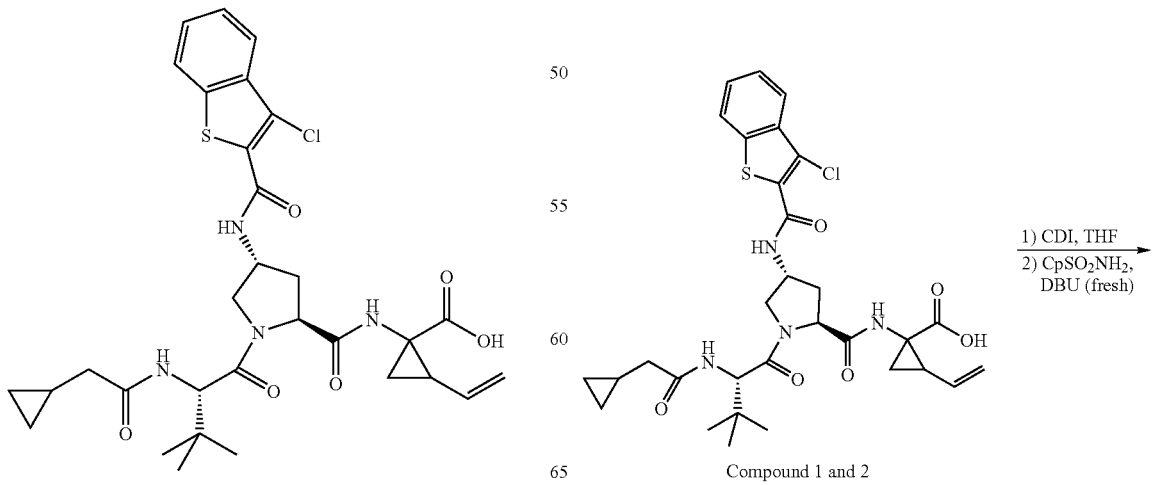

Compound 1 and 2

-continued

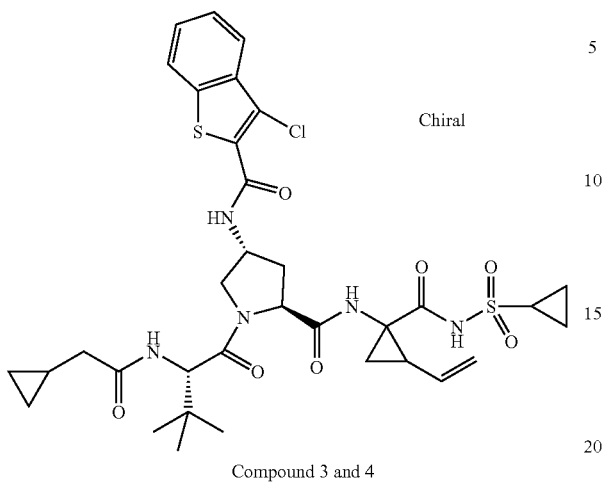

Compound 3 and 4

To a solution of Compound 1 (35 mg, 0.0556 mmol) in THF (5 mL) was added CDI (13.5 g, 0.0834 mmol) under nitrogen. The resulting solution was stirred and refluxed for 1 hour and allowed to cool down to room temperature. Cyclopropylsulfonamide (16.8 mg, 0.139 mmol), prepared by treatment of commercially available cyclopropylsulfonyl chloride with saturated ammonia in THF, was added in one portion before the addition of DBU (0.021 mL, 0.139 mmol). The reaction was stirred for 24 hours, washed with 1N HCl solution, and extracted three time with ethyl acetate. The combined organic layers were washed with brine, dried over $MgSO_4$, filtered, and concentrated. The residue was purified by flash column chromatography (silica gel, ethyl acetate with 1% methanol) to provide a white solid as final product (8 mg, 20% yield).

Compound 3 (50177-060, 50177-048): $^1$H NMR(CD$_3$OD, 300 MHz) δ:7.93 (m, 1H), 7.89 (m, 1H), 7.84 (d, J=8.8 Hz, 1H), 7.55 (m, 2H), 5.75 (m, 1H), 5.30 (dd, J=17.2 Hz, 1.5 Hz, 1H), 5.13 (dd, J=10.2 Hz, 1.8 Hz, 1H), 4.74 (m, 1H), 4.61 (d, J=8.4 Hz, 1H), 4.49 (t, J=8.1 Hz, 1H), 4.04-4.15(m, 2H), 2.94 (m, 1H), 2.44 (m, 1H), 2.23 (m, 2H), 2.13 (d, J=7.3 Hz, 2H), 1.89 (dd, J=8.1 Hz, 5.5 Hz, 1H), 1.43 (dd, J=9.5 Hz, 5.5 Hz, 1H), 1.24 (m, 2H), 1.00-1.12 (m, 11H), 0.94 (m, 1H), 0.45 (m, 2H), 0.14 (m, 2H). LC-MS (retention time: 2.177 minutes.), MS m/z 732 (MH$^+$).

To a solution of Compound 2 (25 mg, 0.04 mmol) in THF (5 mL) was added CDI (9.7 g, 0.06 mmol) under nitrogen. The resulting solution was stirred and refluxed for 1 hour and allowed to cool down to room temperature. Cyclopropylsulfonamide (12.1 mg, 0.1 mmol), prepared by treatment of commercially available cyclopropylsulfonyl chloride with saturated ammonia in THF, was added in one portion before the addition of DBU (0.015 mL, 0.1 mmol). The reaction was stirred for 24 hours, washed with 1N HCl solution, and extracted three time with ethyl acetate. The combined organic layers were washed with brine, dried over MgSO$_4$, filtered, and concentrated. The residue was purified by flash column chromatography (silica gel, ethyl acetate with 1% methanol) to provide a white solid as final product (14 mg, 48% yield).

Compound 4 (50177-044): $^1$H NMR(CD$_3$OD, 300 MHz) δ:7.94 (m, 1H), 7.88 (m, 1H), 7.76 (d, J=8.1 Hz, 1H), 7.54 (m, 2H), 5.81 (m, 1H), 5.29 (d, J=-17.2 Hz, 1H), 5.10 (d, J=10.2 Hz, 1H), 4.78 (m, 1H), 4.58 (d, J=8.8 Hz, 1H), 4.52 (t, J=7.7 Hz, 1H), 4.08 (m, 2H), 2.85 (m, 1H), 2.43 (m, 2H), 2.20 (m, 1H), 2.13 (d, J=7.3 Hz, 2H), 1.85 (dd, J=8.1 Hz, 5.1 Hz, 1H), 1.36 (dd, J=9.5 Hz, 5.1 Hz, 1H), 1.12-0.88 (m, 14H), 0.46 (m, 2H), 0.14 (m, 2H). LC-MS (retention time: 2.113 minutes.), MS m/z 732 (MH$^+$).

Preparation of Intermediate 1:

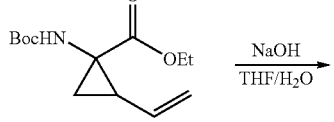

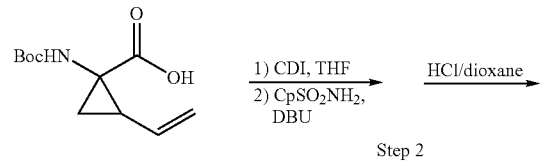

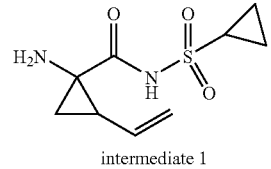

intermediate 1

Step 1:

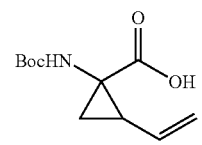

To a solution of racemic N-Boc-(1R,2S)/(1S,2R)-1-amino-2-vinyl-cyclopropane carboxylic acid ethyl ester (0.21 g, 0.82 mmol) in THF, 1N NaOH solution (10 mL) was added. The reaction mixture was stirred at room temperature for overnight. Then it was extracted with ether and the aqueous layer was acidified with 1N HCl solution. It was then extracted with ethyl acetate and the organic layer was separated. It was then washed with brine and dried over MgSO$_4$ and filtered. Evaporation of solvent gave a white solid (0.115 g, 61% yield) as a mixture of diastereoisomers.

48110-086: $^1$H NMR(DMSO-d$_6$, 500 MHz) δ 7.54 (s, 1H), 5.68 (m, 1H), 5.22 (dd, J=17.2 Hz,1.5 Hz, 1H), 5.04 (dd, J=10.2 Hz, 2.2 Hz, 1H), 2.05 (m, 1H), 1.50 (m, 1H), 1.36 (s, 9H), 1.25 (m, 1H). LC-MS (retention time: 1.143 minutes.), MS m/z 250 (M+Na$^+$).

Step 2: Preparation of Intermediate 1.

Intermediate 1

A 1:1 Mixture of Diastereoisomers

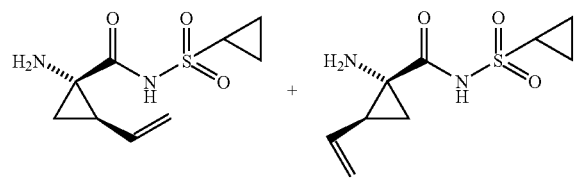

Also represented as:

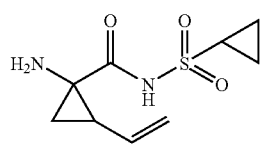

To a solution of N-Boc-(1R,2S)/(1S,2R)-1-amino-2-vinyl-cyclopropane carboxylic acid (4.3 g, 18.9 mmol) in THF (50 mL) was added CDI (4.60 g, 28.35 mmol) under nitrogen. The resulting solution was stirred and refluxed for 1 hour and allowed to cool down to room temperature. Cyclopropylsulfonamide (2.98 g, 24.6 mmol), prepared by treatment of commercially available cyclopropylsulfonyl chloride with saturated ammonia in THF, was added in one portion before the addition of DBU (5.65 mL, 37.8 mmol). The reaction was stirred for 24 hours, washed with 1N HCl solution, and extracted three time with ethyl acetate. The combined organic layers were washed with brine, dried over MgSO$_4$, filtered, and concentrated to yield (1-cyclo-propanesulfonylaminocarbonyl-2-vinyl-cyclopropyl)carbamic acid tert-butyl ester as yellow solid. (48110-179)

The crude compound was then dissolved in 4 N HCl/dioxane (30 mL) and stirred at room temperature overnight. The reaction mixture was concentrated and the residue was purified by Prep. HPLC column to supply reddish solid as TFA salt of Intermediate 1 (2.55 g, 39% two steps).

Intermediate I (also referred to as 48110-182): $^1$H NMR δ:5.82 (m, 1H), 5.37 (d, J=17.1 Hz, 1H), 5.29 (d, J=10.4 Hz, 1H), 2.95 (m, 1H), 2.26 (dd, J=18.0 Hz, 8.2 Hz, 1H), 2.01 (t, J=7.3 Hz, 1H), 1.57 (dd, J=10.1 Hz, 7.3 Hz, 1H), 1.19 (m, 2H), 1.02 (m, 2H). LC-MS (retention time: 0.243 minutes.), MS m/z 231 (MH$^+$).

Example 19

Compound 5 was prepared as follows.

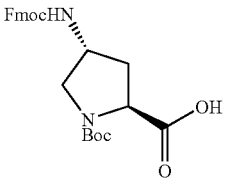 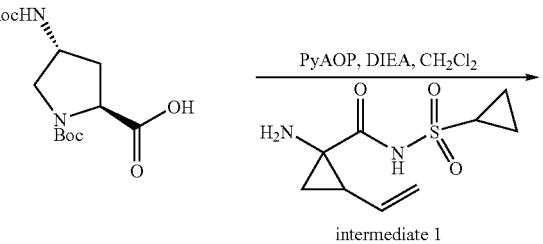

intermediate 1

Step 1

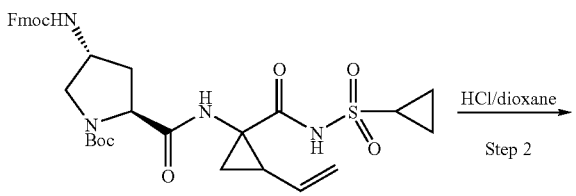

Step 2

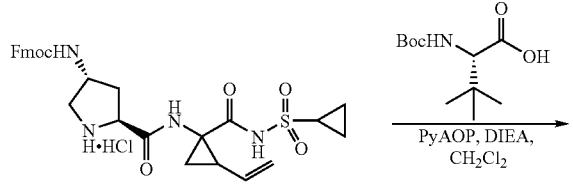

intermediate 3    Step 3

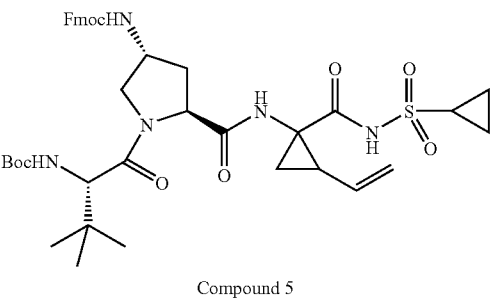

Compound 5

Step 1:

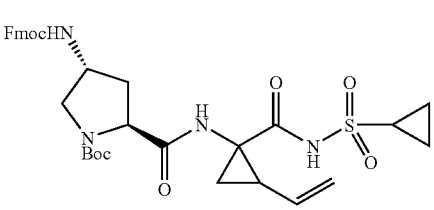

481110-157

To a solution of Fmoc-(2S,4R)-4-amino-1-boc-pyrrolidine-2-carboxylic acid (1.0 g, 2.21 mmol) in CH₃CN (10 mL) was added intermediate 1 (0.825 g, 3.09 mmol), DIEA (0.714 g, 5.53 mmol) and the coupling reagent PyAOP (1.73 g, 3.32 mmol). The solution was stirred at room temperature overnight. Then it was concentrated, washed with water and extracted with ethyl acetate twice. The combined organic layers were washed with brine, dried over MgSO₄, filtered, and concentrated to give a yellow oil. It was purified by flash column eluting with 20% hexane in ethyl acetate to yield 481110-157 an off-white solid as 1:1 diasteromers (1.48 g, 100% yield).

481110-157: ¹H NMR(CD₃OD, 300 MHz) δ 7.80 (d, J=7.3 Hz, 2H), 7.64 (d, J=7.0 Hz, 2H), 7.39 (t, J=7.3 Hz, 2H), 7.31 (t, J=7.3 Hz, 2H), 5.77 (m, 1H), 5.32 (d, J=17.2 Hz, 1H), 5.13(d, J=10.3 Hz, 1H), 4.39 (m, 2H), 4.0-4.3 (m, 4H), 3.70 (m, 1H), 2.92 (m, 1H), 2.05-2.35 (m, 3H), 1.84 (m, 1H), 1.35-1.50 (m, 10H), 1.20(m, 2H), 1.05(m, 2H). LC-MS (retention time: 1.833 minutes.), MS m/z 665 (MH⁺).

Step 2: Preparation of Intermediate 3.

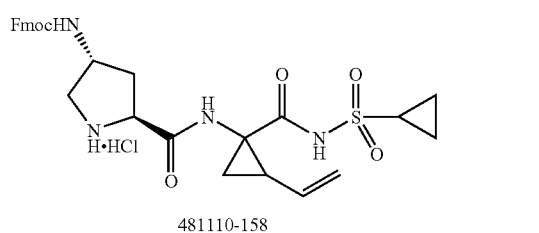

intermediate 3

481110-158

To a suspension of 2-(1-cyclopropanesulfonylaminocarbonyl-2-vinyl-cyclopropylcarbamoyl)-4-(9H-fluoren-9-ylmethoxycarbonylamino)-pyrrolidine-1-carboxylic acid tert-butyl ester (1.44 g, 2.16 mmol) in dioxane (10 mL) was added 5 mL of 4N HCl in dioxane. The mixture was stirred at room temperature for 2 days. It was then concentrated to give a white solid (1.5 g, >100% yield) as the product. 481110-158: ¹H NMR(DMSO-d₆, 300 MHz) 67.90 (d, J=7.3 Hz, 2H), 7.76(s, 1H), 7.69 (d, J=7.0 Hz, 2H), 7.43 (t, J=7.3 Hz, 2H), 7.34 (t, J=7.3 Hz, 2H), 5.59 (m, 1H), 5.30 (d, J=16.8 Hz, 0.5H), 5.27 (d, J=16.8 Hz, 0.5H), 5.13(d, J=10.3 Hz, 1H), 4.0-4.5 (m, 6H), 3.82 (m, 1H), 2.94 (m, 1H), 2.24 (m, 3H), 1.78 (m, 1H), 1.32 (m, 1H), 0.88-1.17(m, 4H). LC-MS (retention time: 1.443 minutes.), MS m/z 565 (MH⁺).

Step 3:

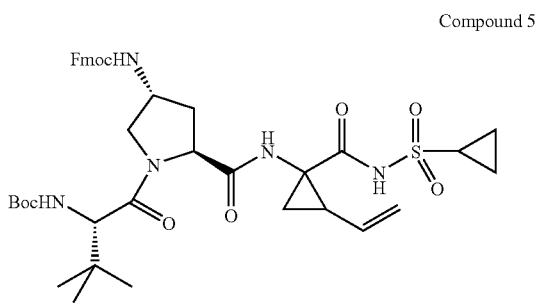

Compound 5

To a solution of [5-(1-cyclopropanesulfonylaminocarbonyl-2-vinyl-cyclopropylcarbamoyl)-pyrrolidin-3-yl]-carbamic acid 9H-fluoren-9-ylmethyl ester hydrochloride (1.5 g, 2.5 mmol) in 15 mL of CH₃CN was added N-Boc-tert-leucine (0.69 g, 3.0 mmol), DIEA (1.09 mL, 6.25 mmol) and the coupling reagent PyAOP (1.95 g, 3.75 mmol). The solution was stirred at room temperature overnight. It was then washed with water and extracted twice with ethyl acetate. The combined organic layers were washed with brine, dried over MgSO₄, filtered, and concentrated to give a yellow oil. It was purified by flash column eluting with 25% hexane in ethyl acetate to yield a white solid as the product Compound 5 as a 1:1 mixture of diastereoiosmers (1.23 g, 63% yield).

(48110-113, 48110-159):¹H NMR(CD₃OD, 500 MHz) δ:7.80 (d, J=7.0 Hz, 2H), 7.64 (m, 2H), 7.39 (m, 2H), 7.30 (m, 2H), 6.60 (m, br, 1H), 5.74 (m, 1H), 5.30 (d, J=17.1 Hz, 1H), 5.12 (d, J=9.5 Hz, 1H), 4.25-4.45 (m, br, 4H), 4.15-4.25(m, br, 2H), 3.89 (m, br, 1H), 2.92 (s, br, 1H), 2.03-2.27 (m, 3H), 1.77-1.90(m, 1H), 1.41 (m, 10H), 0.94-1.22 (m, 13H). LC-MS (retention time: 1.963 minutes.), MS m/z 778 (MH⁺).

Example 20

Compound 6 was prepared as follows.

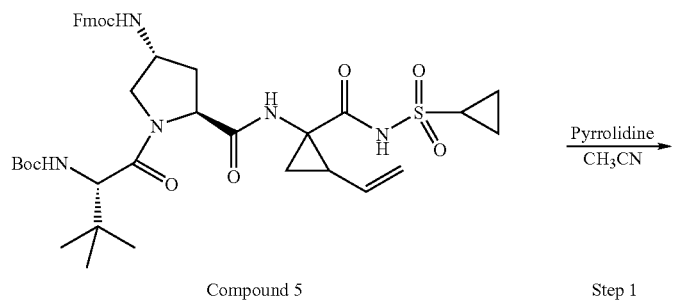

Compound 5     Step 1

-continued

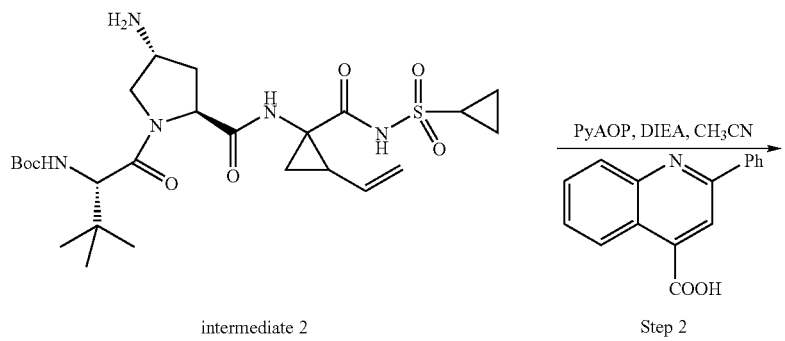

intermediate 2     Step 2

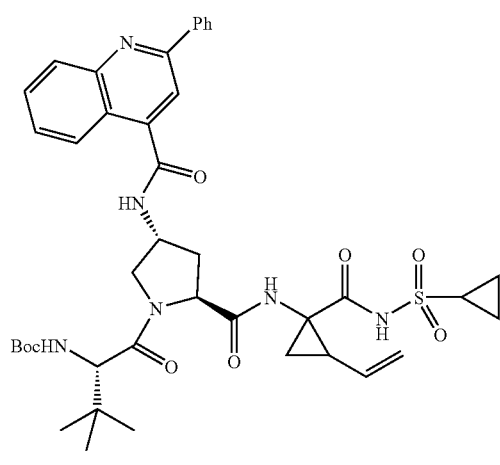

Compound 6

Step 1: Preparation of intermediate 2.

intermediate 2

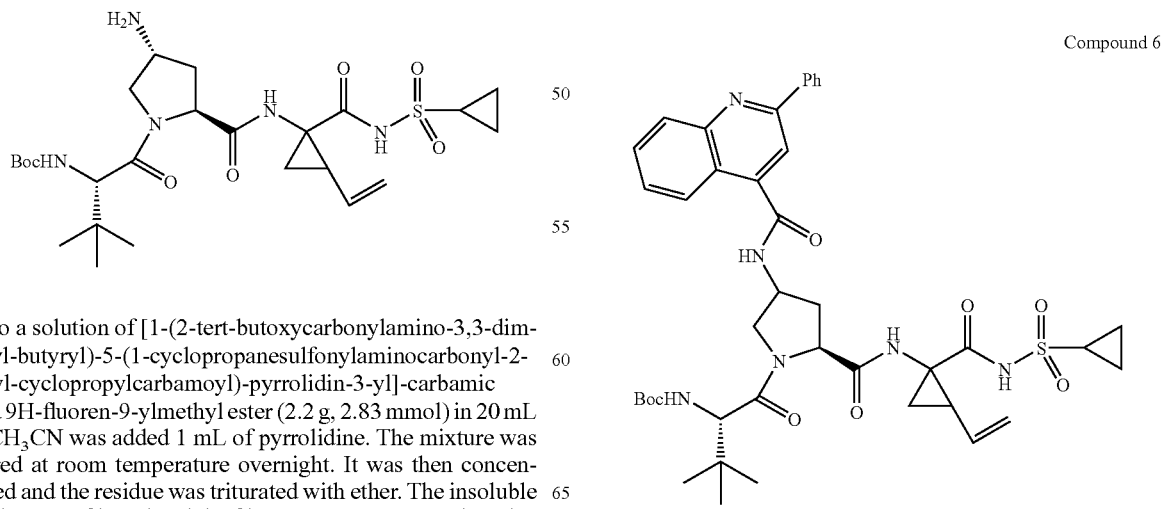

To a solution of [1-(2-tert-butoxycarbonylamino-3,3-dimethyl-butyryl)-5-(1-cyclopropanesulfonylaminocarbonyl-2-vinyl-cyclopropylcarbamoyl)-pyrrolidin-3-yl]-carbamic acid 9H-fluoren-9-ylmethyl ester (2.2 g, 2.83 mmol) in 20 mL of $CH_3CN$ was added 1 mL of pyrrolidine. The mixture was stirred at room temperature overnight. It was then concentrated and the residue was triturated with ether. The insoluble product was filtered and the filtrate was concentrated to give a yellowish thick oil as crude product (intermediate 2, 48110-141) to carry on (1.3 g, 83% yield). LC-MS (retention time: 1.830 minutes.), MS m/z 556 (MH$^+$).

Step 2:

Compound 6

To a solution of {1-[4-amino-2-(1-cyclopropanesulfonylaminocarbonyl-2-vinyl-cyclopropylcarbamoyl)-pyrrolidine-1-carbonyl]-2,2-dimethyl-propyl}-carbamic acid tert-butyl ester (intermediate 2, 40 mg, 0.072 mmol) in 5 mL of CH₃CN was added 2-phenyl-4-quinolinecarboxylic acid (21.5 mg, 0.0864 mmol), DIEA (0.019 mL, 0.108 mmol) and the coupling reagent PyAOP (56.3 mg, 0.108 mmol). The solution was stirred at room temperature for 2 days. It was then concentrated, washed with water and extracted twice with ethyl acetate. The combined organic layers were washed with brine, dried over MgSO₄, filtered, and concentrated. The crude product was purified by preparative HPLC column to yield a colorless oil as the product Compound 6, (48110-142) as a 1:1 mixture of diastereoisomers (11.2 mg, 20% yield).

¹H NMR(CDCl₃, 500 MHz) δ:8.10-8.20 (m, 3H), 8.07 (t, J=7.9 Hz, 1H), 7.90 (d, J=3.7 Hz, 1H), 7.73(m, 1H), 7.57 (m, 1H), 7.42-7.54(m, 3H), 5.67 (m, 1H), 5.33 (d, J=17.1 Hz, 0.5H), 5.24 (d, J=17.1 Hz, 0.5H), 5.14 (m, 1H), 4.83 (m, br, 1H), 4.55 (m, br, 1H), 4.33(m, br, 1H), 4.02 (m, 1H), 3.84 (m,br, 1H), 2.83 (s, br, 1H), 2.65 (m, 1H), 2.53 (m, 1H), 2.06-2.18 (m, 1H), 1.93 (m, 1H), 1.37 (m, 1H), 1.29 (m, 9H), 0.93-1.16(m, 13H). LC-MS (retention time: 2.083 minutes.), MS m/z 787 (MH⁺).

Example 21

Compound 7 was prepared as follows.

To a suspension of [1-(2-tert-butoxycarbonylamino-3,3-dimethyl-butyryl)-5-(1-cyclopropanesulfonylaminocarbonyl-2-vinyl-cyclopropylcarbamoyl)-pyrrolidin-3-yl]-carbamic acid 9H-fluoren-9-ylmethyl ester (Compound 5, 1.0 g, 1.29 mmol) in dioxane (10 mL) was added 5 mL of 4N HCl in dioxane. The mixture was stirred at room temperature overnight. It was then concentrated to give a white solid, which was used in the next step without purification.

To a mixture of the above white solid in 10 mL of CH₃CN was added cyclopropylacetic acid (0.15 g, 1.54 mmol), DIEA (0.56 mL, 3.21 mmol) and the coupling reagent PyAOP (1.0 g, 1.93 mmol). The solution was stirred at room temperature overnight. It was then washed with water and extracted twice with ethyl acetate. The combined organic layers were washed with brine, dried over MgSO₄, filtered, and concentrated to give a yellow oil. It was purified by flash column eluting with 25% hexane in ethyl acetate to yield Compound 7, (48110-160) as a 1:1 mixture of diastereoisomers (0.63 g, 65% yield).

LC-MS (retention time: 1.880 minutes.), MS m/z 760 (MH⁺).

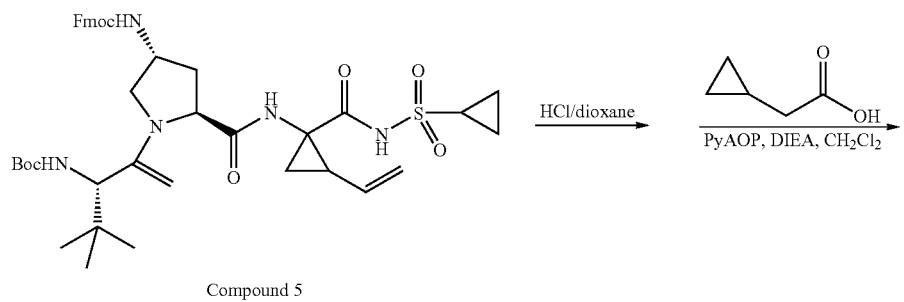

Compound 5

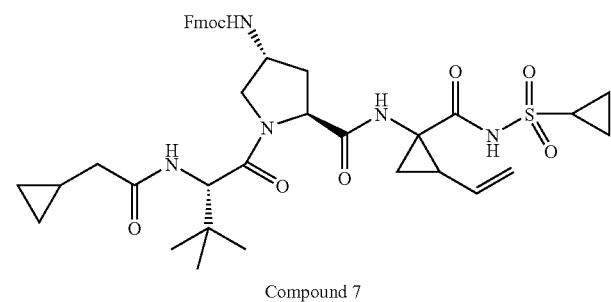

Compound 7

Example 22

Compound 8 was prepared as follows.

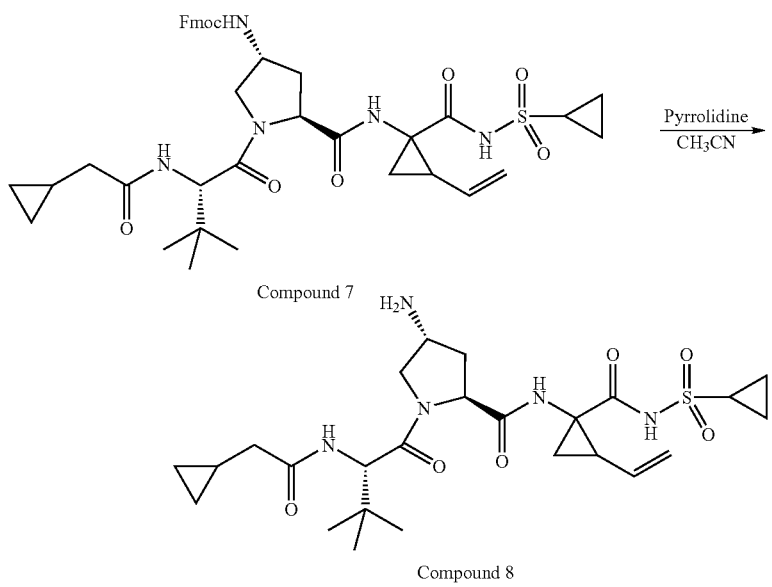

Compound 7

Compound 8

To a solution of Compound 7 (0.63 g, 0.83 mmol) in 20 mL of CH$_3$CN was added 1 mL of pyrrolidine. The mixture was stirred at room temperature overnight. It was then concentrated and the residue was triturated with ether. The insoluble product was filtered and then purified by preparative HPLC column to provide Compound 8 (48110-161), (0.32 g, 58% yield).

$^1$H NMR(CD$_3$OD, 300 MHz) δ:5.72 (m, 1H), 5.31 (d, J=17.2 Hz, 1H), 5.15 (d, J=9.9 Hz, 1H), 4.49 (m, 2H), 4.08(m, br, 3H), 2.95 (m, 1H), 2.2-2.45 (m, 3H), 2.18 (d, J=7.0 Hz, 2H), 1.86 (m, 1H), 1.39 (m, 1H), 0.80-1.25 (m, 14H), 0.54 (m, 2H), 0.20 (m, 2H).

LC-MS (retention time: 1.217 minutes.), MS m/z 538 (MH$^+$).

Example 23

Compound 9 was prepared as follows.

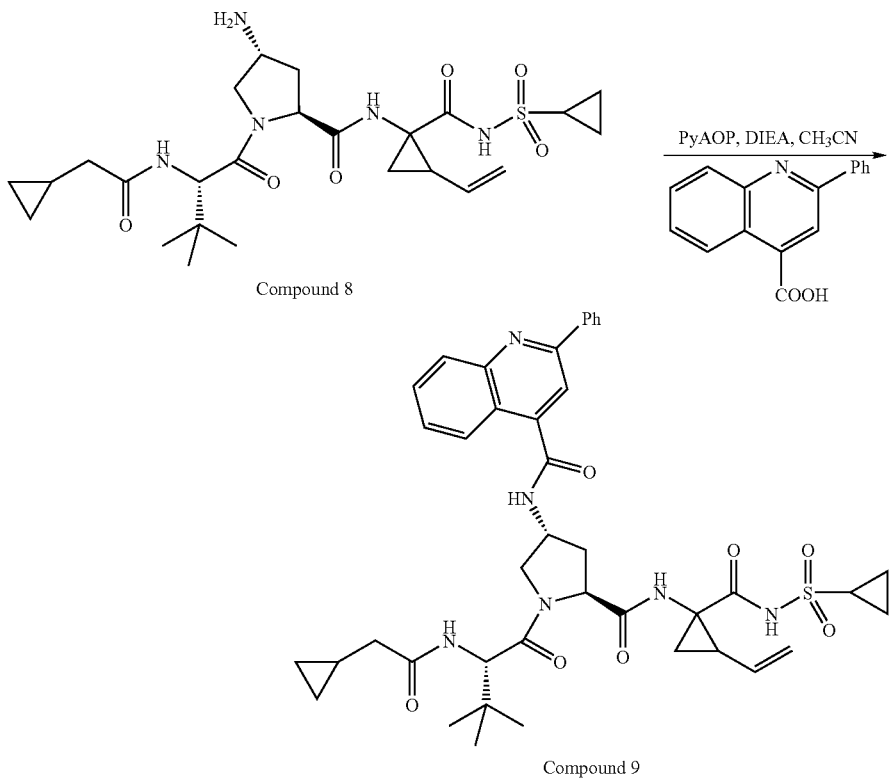

Compound 8

Compound 9

To a solution of Compound 8 (20 mg, 0.03 mmol) in 5 mL of CH₃CN was added 2-phenyl-4-quinolinecarboxylic acid (11.1 mg, 0.04 mmol), DIEA (0.01 mL, 0.05 mmol) and the coupling reagent PyAOP (29.1 mg, 0.05 mmol). The solution was stirred at room temperature for overnight. It was then concentrated, washed with water and extracted twice with ethyl acetate. The combined organic layers were washed with brine, dried over MgSO₄, filtered, and concentrated. The crude product was purified by preparative HPLC column to yield a yellow oil as 1:1 diatereomers (Compound 9)(18 mg, 56% yield).

(Compound 9, 48110-164): $^1$H NMR(CD₃OD, 500 MHz) δ:8.26-8.34 (m, 3H), 8.18 (m, 2H), 7.99(m, 1H), 7.81 (m, 1H), 7.66(m, 3H), 5.74 (m, 1H), 5.32 (m, 1H), 5.14 (m, 1H), 4.88 (m, 1H), 4.57 (m, 1H), 4.48 (m, 1H), 4.23(m, 1H), 4.11 (m, 1H), 2.95 (m, 1H), 2.46 (m, 1H), 2.21-2.38 (m, 2H), 2.02 (m, 2H), 1.90 (dd, J=8.2 Hz, 5.5 Hz, 0.5H), 1.82 (dd, J=8.2 Hz, 5.2 Hz, 0.5H), 1.38-1.46 (m, 1H), 1.00-1.23(m, 13H), 0.79 (m, 1H), 0.37 (m, 2H), 0.06 (m, 2H).

LC-MS (retention time: 1.673 minutes.), MS m/z 769 (MH⁺).

Examples 24 and 25

Compounds 10 and 11 were prepared as follows.

Following the general procedure of acid-amine coupling as shown in Example 23, Compound 8(30 mg, 0.0558 mmol) was treated with 4-quionlinecarboxylic acid (11.6 mg, 0.067 mmol), DIEA (0.014 mL, 0.084 mmol) and the coupling reagent PyAOP (43.7 mg, 0.067 mmol) in acetonitrile (3 mL). After purification by Prep.HPLC column, two diastereomers as TFA salts were afforded as white solid.

Compound 10 (48110-165-1, lower Rf isomer) (7 mg, 16% yield):

LC-MS (retention time: 1.200 minutes.), MS m/z 693 (MH⁺).

Compound 11 (48110-165-2, higher Rf isomer) (4.1 mg, 9% yield):

LC-MS (retention time: 1.677 minutes.), MS m/z 693 (MH⁺).

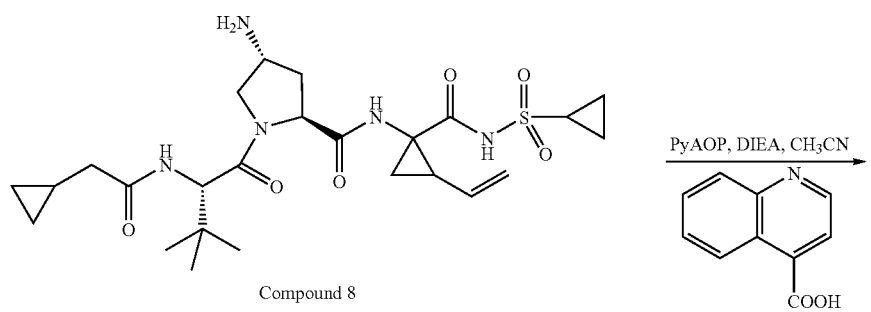

Compound 8

PyAOP, DIEA, CH₃CN

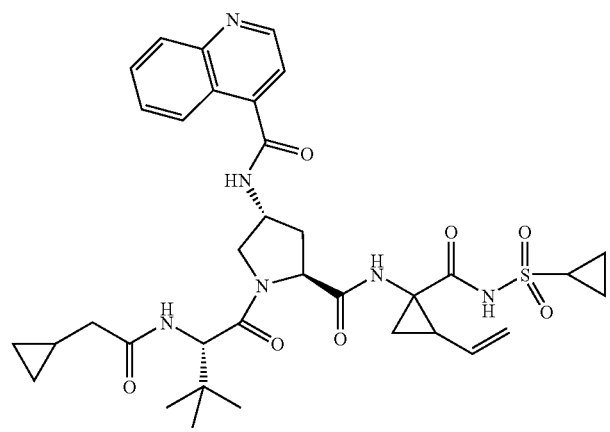

Compound 10 and 11

Example 26

Compound 12 was prepared as follows.

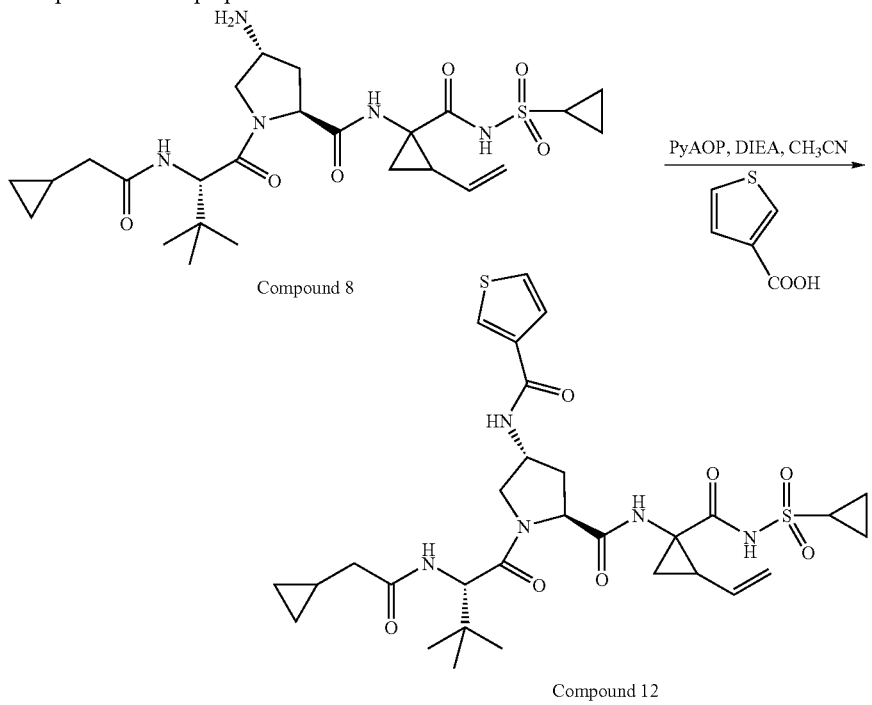

Following the general procedure of acid-amine coupling as shown in Example 23, Compound 8(20 mg, 0.03 mmol) was treated with 3-thiophenecarboxylic acid (4.6 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, a white solid was obtained as final 1:1 diastereomers (Compound 12) (9.1 mg, 47% yield).

(Compound 12, 48110-168A): LC-MS (retention time: 1.323 minutes.), MS m/z 648 (MH$^+$).

Example 27

Compound 13 was prepared as follows.

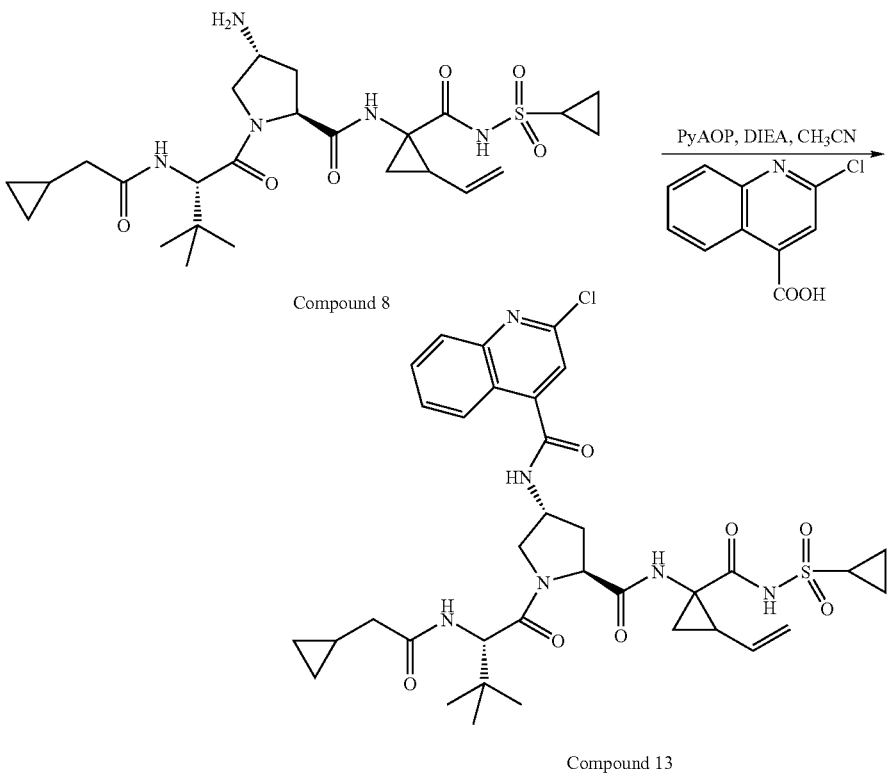

Following the general procedure of acid-amine coupling as shown in Example 23, Compound 8 (20 mg, 0.03 mmol) was treated with 2-chloro-4-carboxy quinoline (7.5 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, 1:1 diastereomix (Compound 13) was obtained (11 mg, 44% yield).

(Compound 13, 48110-168B): $^1$H NMR(CD$_3$OD, 300 MHz) δ: diastereomer mixture. LC-MS (retention time: 1.437 minutes.), MS m/z 727 (MH$^+$).

Examples 28 and 29

Compounds 14 and 15 were prepared as follows.

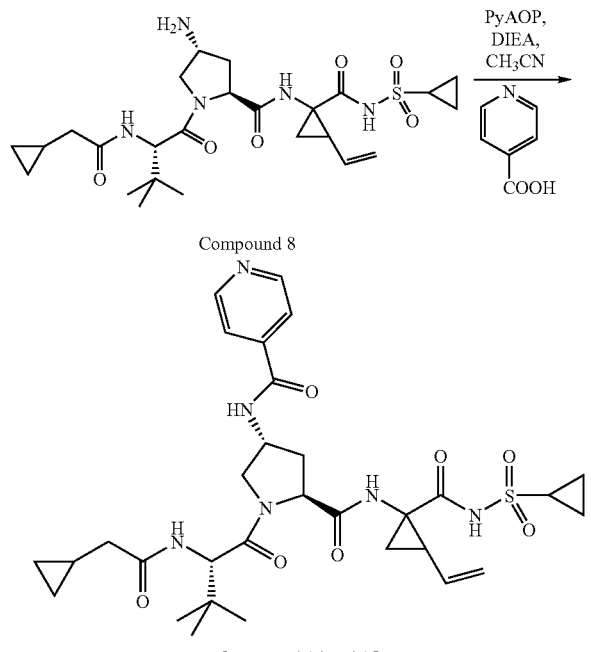

Compound 8

Compound 14 and 15

Following the general procedure of acid-amine coupling as shown in Example 23, Compound 8 (20 mg, 0.03 mmol) was treated with isonicotinic acid (4.4 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, two diastereomers as colorless thick oil were obtained as TFA salts.

Compound 14 (48110-168C1, lower Rf isomer) (4.9 mg, 21% yield): $^1$H NMR(CD$_3$OD, 300 MHz) δ:8.80 (m, 2H), 8.05 (d, J=5.5 Hz, 2H), 5.73 (m, 1H), 5.30 (d, J=16.8 Hz, 1H), 5.14 (d, J=9.9 Hz, 1H), 4.73 (m, 1H), 4.54 (m, 1H), 4.45 (m, 1H), 4.00-4.18 (m, 2H), 2.94 (m, 1H), 2.38 (m, 1H), 2.22 (m, 2H), 2.17 (d, J=7.0 Hz, 2H), 1.89 (dd, J=7.7 Hz, 5.5 Hz, 1H), 1.38 (m, 1H), 1.23 (m,1H), 0.94-1.14 (m, 13H), 0.51 (m, 2H), 0.19 (m, 2H). LC-MS (retention time: 1.123 minutes.), MS m/z 643 (MH$^+$).

Compound 15 (48110-168C2, higher Rf isomer) (3.7 mg, 16% yield): $^1$H NMR(CD$_3$OD, 300 MHz) δ:8.78 (m, 2H), 8.02 (d, J=5.5 Hz, 2H), 5.74 (m, 1H), 5.33 (d, J=16.8 Hz, 1H), 5.15 (d, J=9.9 Hz, 1H), 4.76 (m, 1H), 4.52 (m, 1H), 4.43 (m, 1H), 4.00-4.20 (m, 2H), 2.96 (m, 1H), 2.40 (m, 1H), 2.21-2.31 (m, 2H), 2.17 (d, J=6.6 Hz, 2H), 1.81 (dd, J=8.0 Hz, 5.5 Hz, 1H), 1.38 (m, 1H), 1.29 (m, 1H), 0.8-1.2 (m, 13H), 0.51 (m, 2H), 0.19 (m, 2H). LC-MS (retention time: 1.173 minutes.), MS m/z 643 (MH$^+$).

Example 30

Compound 16 was prepared as follows.

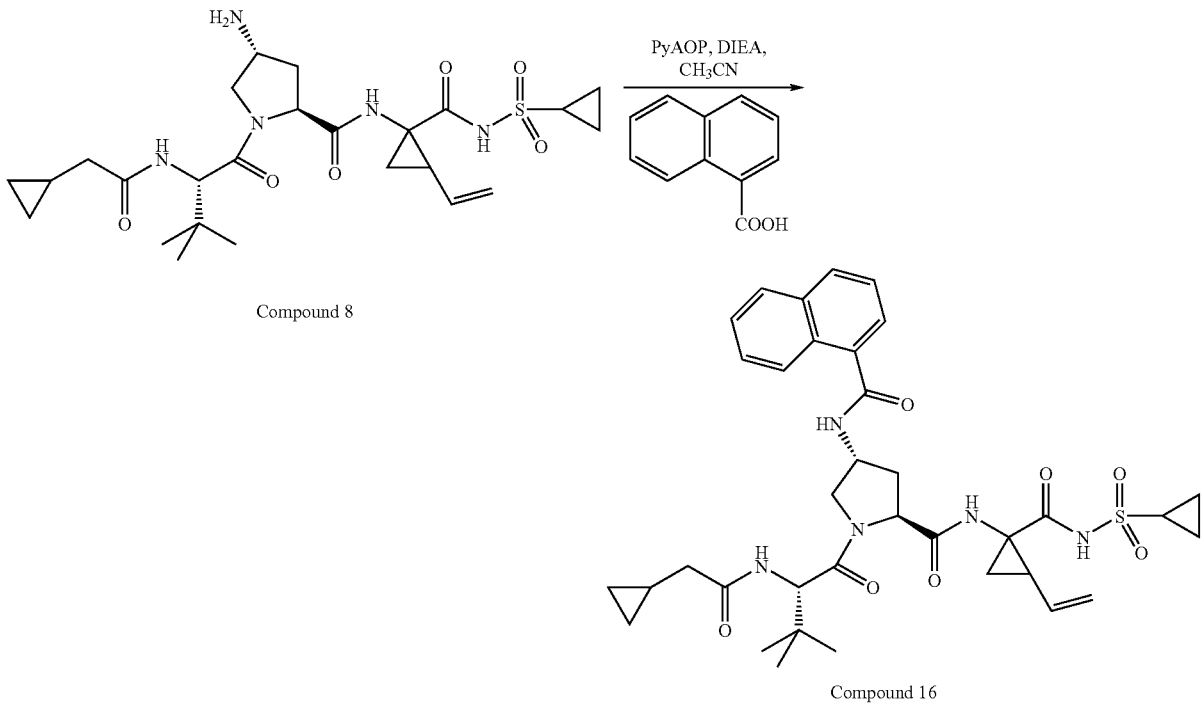

Compound 16

Following the general procedure of acid-amine coupling as shown in Example 23, Compound 8 (20 mg, 0.03 mmol) was treated with 1-naphthoic acid (6.2 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, an off-white solid was obtained as final 1:1 diastereomers (Compound 16) (9.1 mg, 44% yield). (48110-169A): LC-MS (retention time: 1.430 minutes.), MS m/z 692 (MH+).

Examples 31 and 32

Compounds 17 and 18 were prepared as follows.

Following the general procedure of acid-amine coupling as shown in Example 23, Compound 8 (20 mg, 0.03 mmol) was treated with 2-methyl-imidazo[1,2-a]pyridine-3-carboxylic acid (6.3 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, two diastereomers as white solid were obtained as TFA salts.

Compound 17 (48110-169B1, lower Rf isomer) (3.5 mg, 14% yield):
  LC-MS (retention time: 1.527 minutes.), MS m/z 696 (MH+).

Compound 18 (48110-169B2, higher Rf isomer) (2 mg, 8% yield):
  LC-MS (retention time: 1.550 minutes.), MS m/z 696 (MH+).

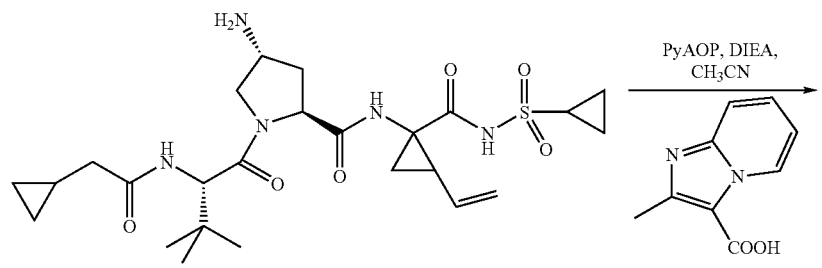

Compound 8

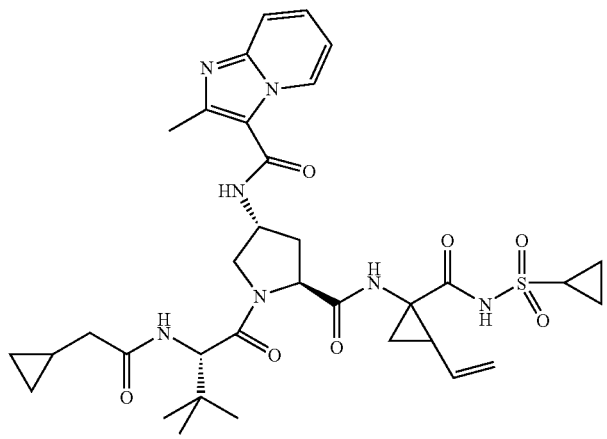

Compound 17 and 18

Example 33

Compound 19 was prepared as follows.

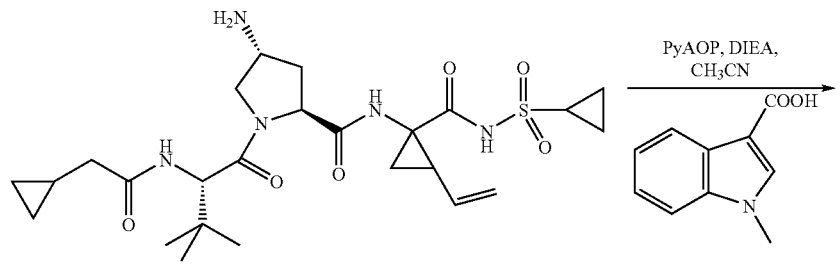

Compound 8

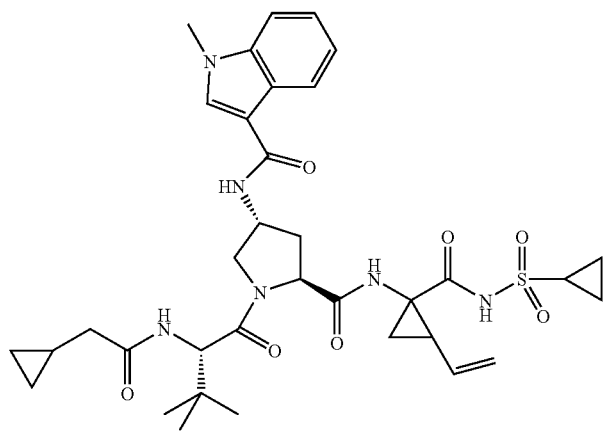

Compound 19

Following the general procedure of acid-amine coupling as shown in Example 23, Compound 8 (20 mg, 0.03 mmol) was treated with 1-methylindole-3-carboxylic acid (4.6 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, a white solid was obtained as final 1:1 diastereomers (Compound 19) (7.1 mg, 29% yield).

(Compound 19, 48110-169C): LC-MS (retention time: 1.91 minutes.), MS m/z 695 (MH$^+$).

Example 34

Compound 20 was prepared as follows.

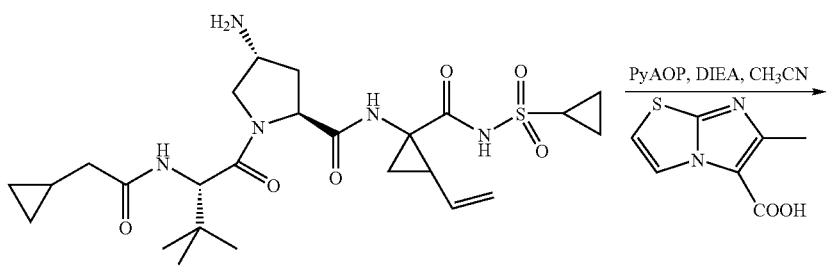

Compound 8

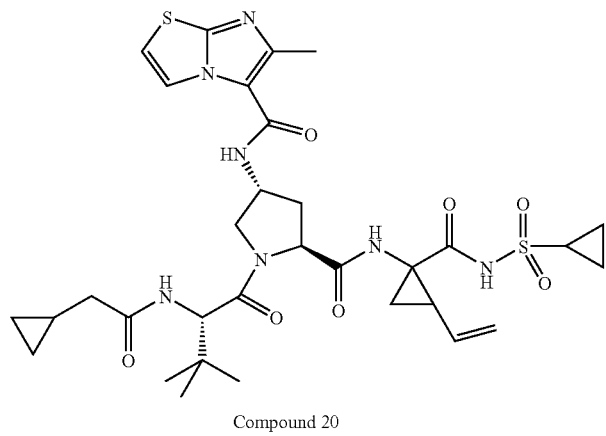

Compound 20

Following the general procedure of acid-amine coupling as shown in Example 23, Compound 8 (20 mg, 0.03 mmol) was treated with 6-methyl-imidazo[2,1-b]thiazole-5-carboxylic acid (6.6 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, a colorless thick oil as TFA salt was obtained as final 1:1 diastereomers (Compound 20) (10.4 mg, 42% yield). (48110-171A): LC-MS (retention time: 1.187 minutes.), MS m/z 702 (MH+).

Example 35

Compound 21 was prepared as follows.

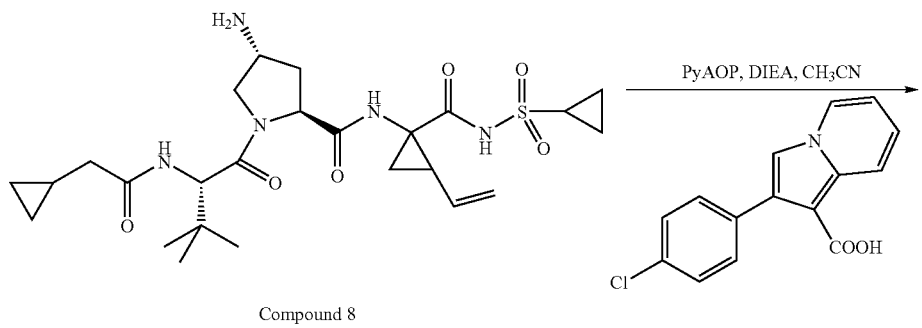

Compound 8

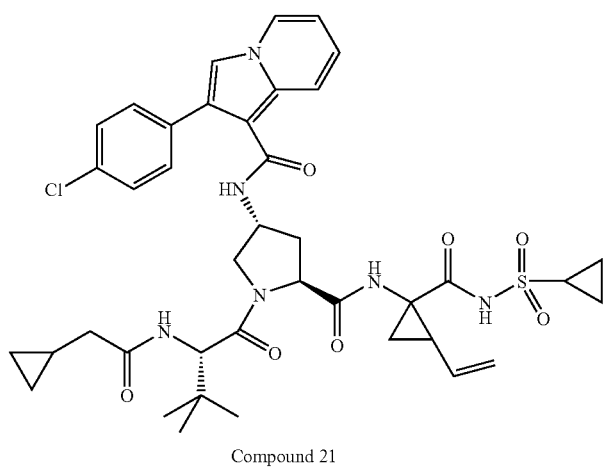

Compound 21

Following the general procedure of acid-amine coupling as shown in Example 23, Compound 8 (20 mg, 0.03 mmol) was treated with 2-(4-Chlorophenyl)-indolizine-1-carboxylic acid (9.8 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, a greenish solid as TFA salt was obtained as final 1:1 diastereomers (Compound 21) (2.3 mg, 8.5% yield).

(Compound 21, 48110-171B): $^1$H NMR(CD$_3$OD, 500 MHz) δ: diastereomer mixture. LC-MS (retention time: 1.627 minutes.), MS m/z 791 (MH$^+$).

Example 36

Compound 22 was prepared as follows.

Following the general procedure of acid-amine coupling as shown in Example 23, Compound 8 (20 mg, 0.03 mmol) was treated with 4-chloro-1,3-dimethyl-1H-pyrazolo[3,4-b]pyridine-5-carboxylic acid (8.1 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, a colorless oil as TFA salt was obtained as final 1:1 diastereomers (Compound 22) (6.2 mg, 24% yield).

(Compound 22, 48110-171C): $^1$H NMR(CD$_3$OD, 500 MHz) δ: diastereomer mixture. LC-MS (retention time: 1.287 minutes.), MS m/z 746 (MH$^+$).

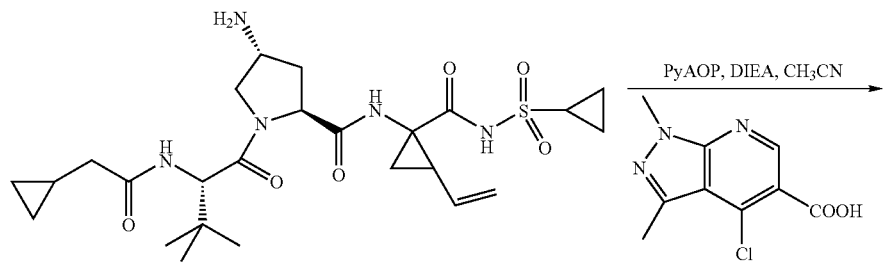

Compound 8

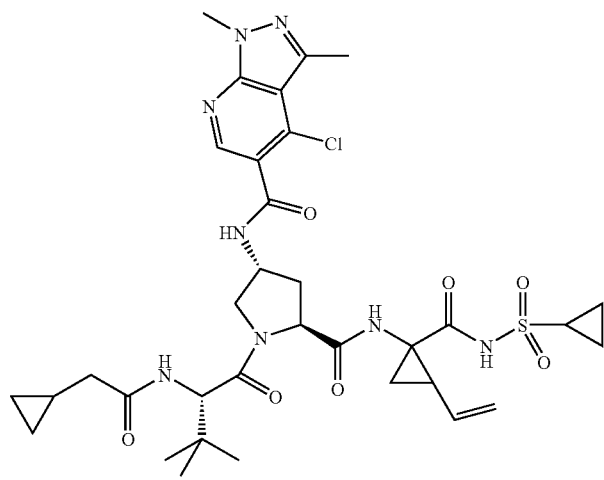

Compound 22

Example 37

Compound 23 was prepared as follows.

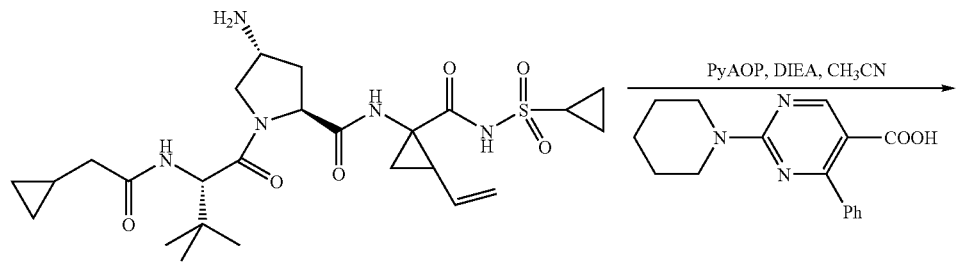

Compound 8

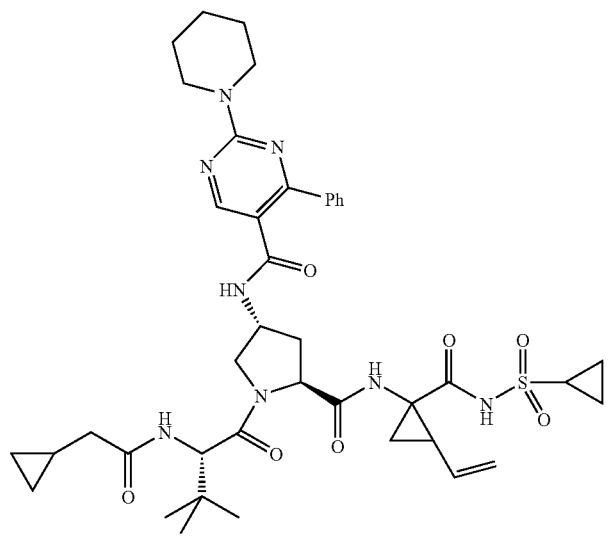

Compound 23

Following the general procedure of acid-amine coupling as shown in Example 23, Compound 8 (20 mg, 0.03 mmol) was treated with 4-phenyl-2-piperidin-1-yl-pyrimidine-5-carboxylic acid hydrochloride (11.5 mg, 0.036 mmol), DIEA (0.013 mL, 0.075 mmol) and the coupling reagent PyAOP (23.5 mg, 0.045 mmol) in acetonitrile (3 mL). After purification by Prep.HPLC column, an off-white solid as TFA salt was obtained as final 1:1 diastereomers (Compound 23) (10.4 mg, 42% yield).

(Compound 23, 48110-171D): LC-MS (retention time: 1.633 minutes.), MS m/z 804(MH$^+$).

Example 38

Compound 24 was prepared as follows.

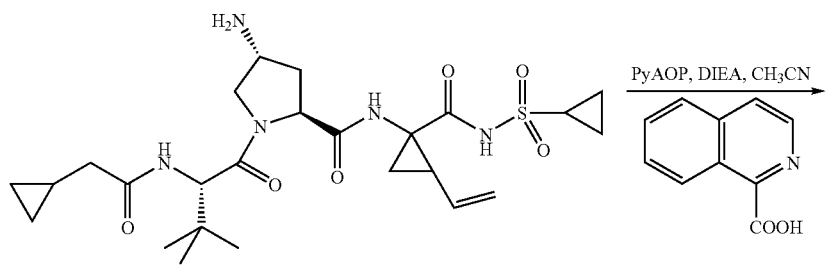

Compound 8

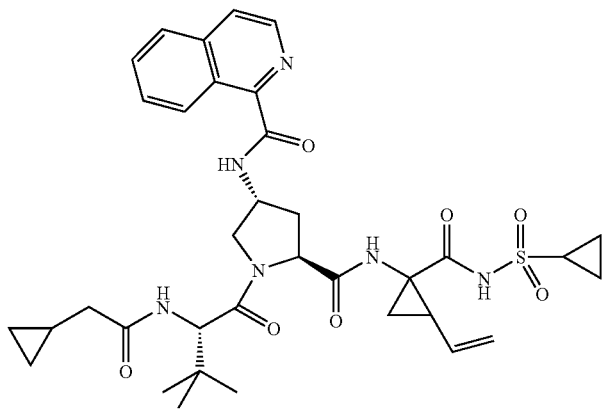

Compound 24

Following the general procedure of acid-amine coupling as shown in Example 23, Compound 8 (25 mg, 0.033 mmol) was treated with isoquinoline-1-carboxylic acid (7.8 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, an off-white solid as TFA salt was obtained as final 1:1 diastereomers (Compound 24) (17.8 mg, 59% yield).

(Compound 24, 48110-186A): LC-MS (retention time: 1.547 minutes.), MS m/z 693(MH$^+$).

Example 39

Compound 25 was prepared as follows.

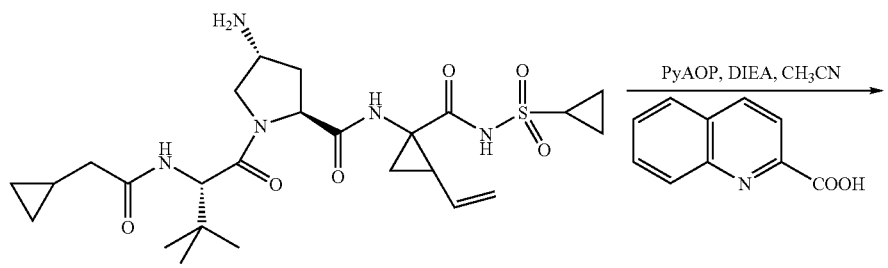

Compound 8

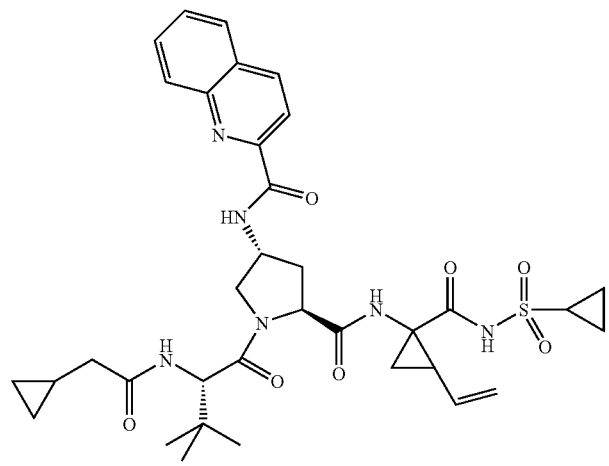

Compound 25

Following the general procedure of acid-amine coupling as shown in Example 23, Compound 8 (25 mg, 0.033 mmol) was treated with quinoline-2-carboxylic acid (7.8 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, a white solid as TFA salt was obtained as final 1:1 diastereomers (Compound 25) (18.9 mg, 63% yield).

(Compound 25, 48110-186B): LC-MS (retention time: 1.627 minutes.), MS m/z 693(MH$^+$).

Following the general procedure of acid-amine coupling as shown in Example 23, Compound 8 (25 mg, 0.033 mmol) was treated with 1-methyl-1H-indole-2-carboxylic acid (7.9 mg, 0.045 mmol), DEEA (0.0163 mL, 0.094 mmol) and the coupling reagent PyAOP (29.3 mg, 0.056 mmol) in acetonitrile (3 mL). After purification by Prep.HPLC column, a white solid was obtained as final 1:1 diastereomers (Compound 26) (15.8 mg, 52% yield).

(Compound 26, 48110-186C): $^1$H NMR(CD$_3$OD, 500 MHz) δ: 7.55 (d, J=7.9 Hz, 1H), 7.44 (d, J=8.6 Hz, 1H), 7.29 (t, J=7.6 Hz, 1H), 7.16 (S, 1H), 7.09(t, J=7.6 Hz, 1H), 5.73 (m, 1H), 5.32 (m, 1H), 5.13 (m, 1H), 4.70 (m, 1H), 4.45 (m, 1H), 4.12 (m, 1H), 3.95-4.08 (m, 5H), 2.95 (m, 1H), 2.41 (m, 1H), 2.1-2.3 (m, 4H), 1.90 (dd, J=7.9 Hz, 5.5 Hz, 0.5H), 1.81 (dd, J=7.9 Hz, 5.2 Hz, 0.5H), 1.40 (m, 1H), 0.98-1.3 (m, 14H), 0.50 (m, 2H), 0.18 (m, 2H). LC-MS (retention time: 1.723 minutes.), MS m/z 695(MH$^+$).

Example 40

Compound 26 was prepared as follows.

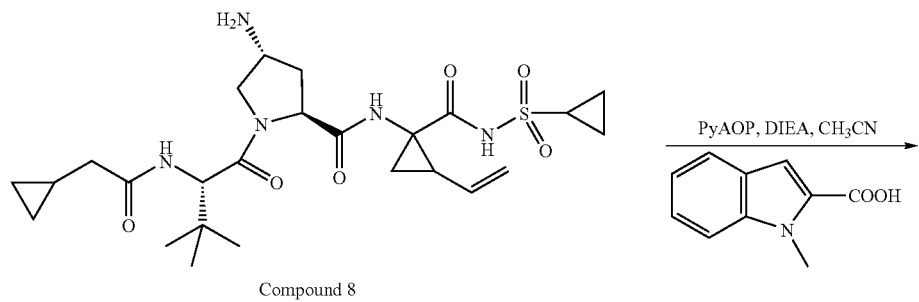

Compound 8

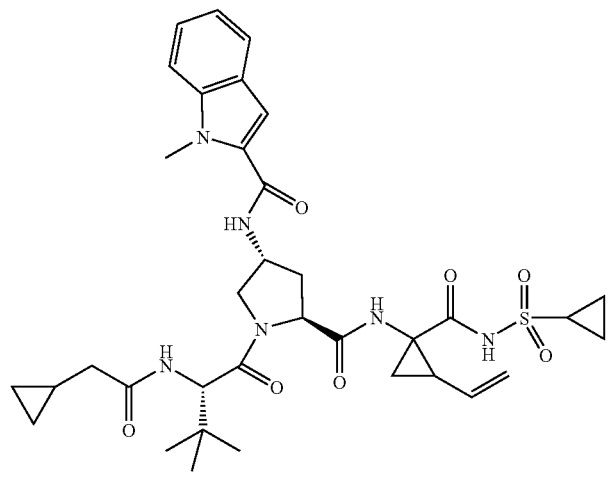

Compound 26

Example 41

Compound 27 was prepared as follows.

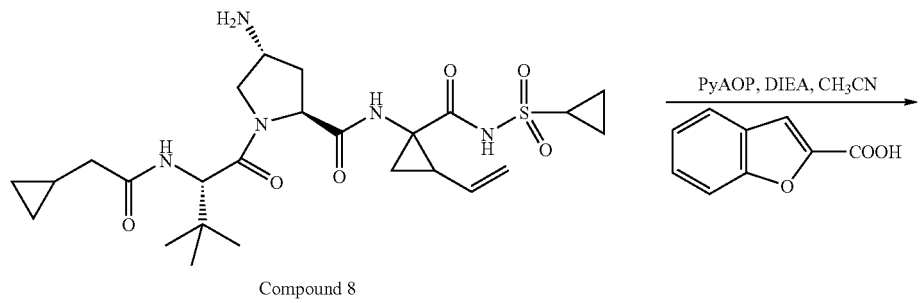

Compound 8

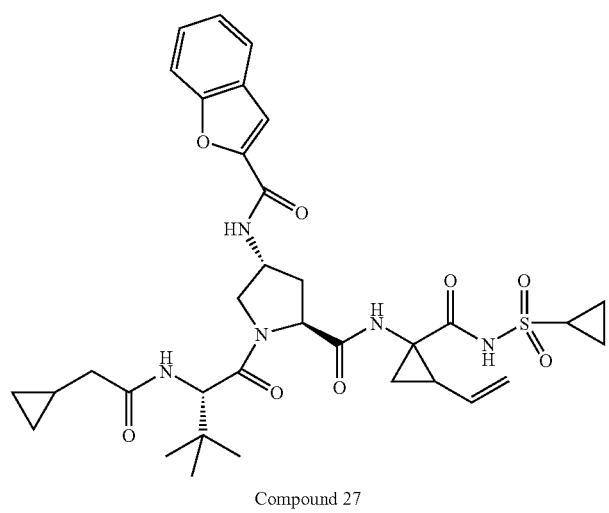

Compound 27

Following the general procedure of acid-amine coupling as shown in Example 23, Compound 8 (25 mg, 0.033 mmol) was treated with coumarilic acid (7.3 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, a yellowish solid was obtained as final 1:1 diastereomers (Compound 27) (17.9 mg, 70% yield).

(Compound 27, 48110-186D): LC-MS (retention time: 1.630 minutes.), MS m/z 682(MH+).

Example 42

Compound 28 was prepared as follows.

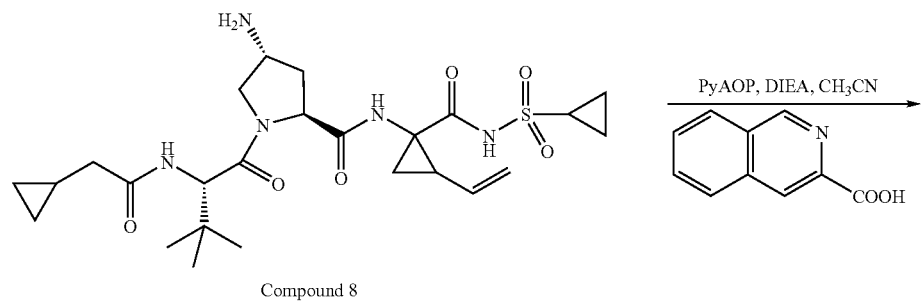

Compound 8

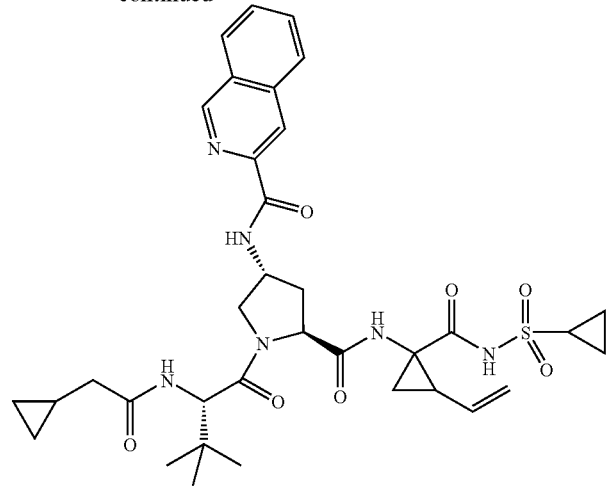

Compound 28

Following the general procedure of acid-amine coupling as shown in Example 23, Compound 8 (25 mg, 0.033 mmol) was treated with isoquinoline-3-carboxylic acid hydrate (8.6 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, a white solid as TFA salt was obtained as final 1:1 diastereomers (Compound 28) (19.9 mg, 66% yield).

(Compound 28, 48110-188A): $^1$H NMR(CD$_3$OD, 500 MHz) δ: 9.37 (s, 1H), 8.65 (s, 1H), 8.26 (d, J=8.2 Hz, 1H), 8.14 (d, J=8.2 Hz, 1H), 7.95 (t, J=7.6 Hz, 1H), 7.87t, J=7.6 Hz, 1H), 5.75 (m, 1H), 5.32 (m, 1H), 5.14 (m, 1H), 4.84 (m, 1H), 4.63 (m, 1H), 4.50 (m, 1H), 4.08-4.18 (m, 2H), 2.95 (m, 1H), 2.43 (m, 1H), 2.1-2.36 (m, 4H), 1.90 (dd, J=7.9 Hz, 5.8 Hz, 0.5H), 1.82 (dd, J=7.9 Hz, 5.2 Hz, 0.5H), 1.43 (m, 1 H), 1.01-1.32 (m, 13H), 0.97 (m, 1H), 0.49 (m, 2H), 0.17 (m, 2H).

LC-MS (retention time: 1.573 minutes.), MS m/z 693(MH$^+$).

Example 43

Compound 29 was prepared as follows.

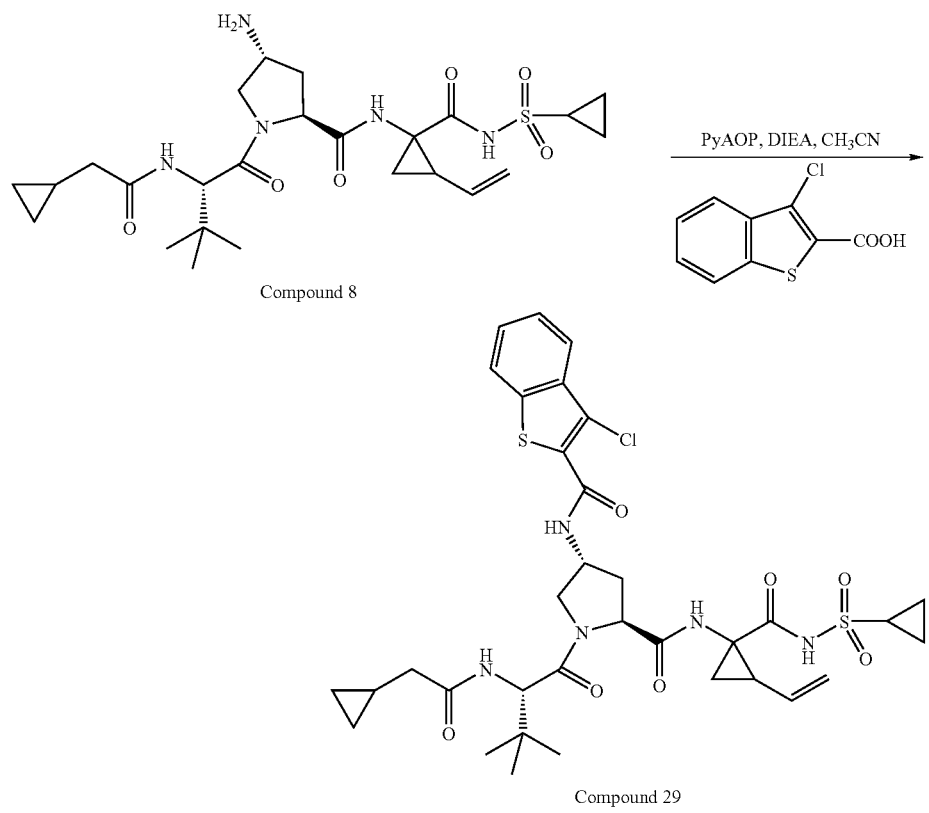

Compound 8

Compound 29

Following the general procedure of acid-amine coupling as shown in Example 23, Compound 8 (25 mg, 0.033 mmol) was treated with 3-chloro-benzo[b]thiophene-2-carboxylic acid (9.6 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, an off-white solid was obtained as final 1:1 diastereomers (Compound 29) (22.1 mg, 81% yield).

(Compound 29, 48110-188C): LC-MS (retention time: 1.720 minutes.), MS m/z 732(MH⁺).

Example 44

Compound 30 was prepared as follows.

Following the general procedure of acid-amine coupling as shown in Example 23, Compound 8(25 mg, 0.033 mmol) was treated with 2,3-dihydro-benzofuran-7-carboxylic acid (7.4 mg, 0.045 mmol), DIEA (0.0163 mL, 0.094 mmol) and the coupling reagent PyAop (29.3 mg, 0.056 mmol) in acetonitrile (3 mL). After purification by Prep.HPLC column, a white solid was obtained as final 1:1 diastereomers (Compound 30) (18 mg, 70% yield).

(Compound 30, 48110-188D): LC-MS (retention time: 1.547 minutes.), MS m/z 684(MH⁺).

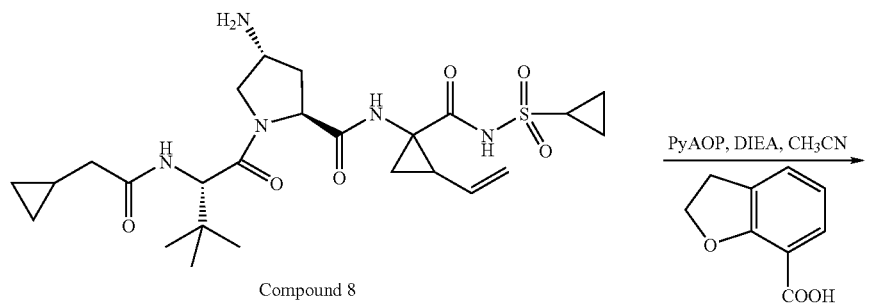

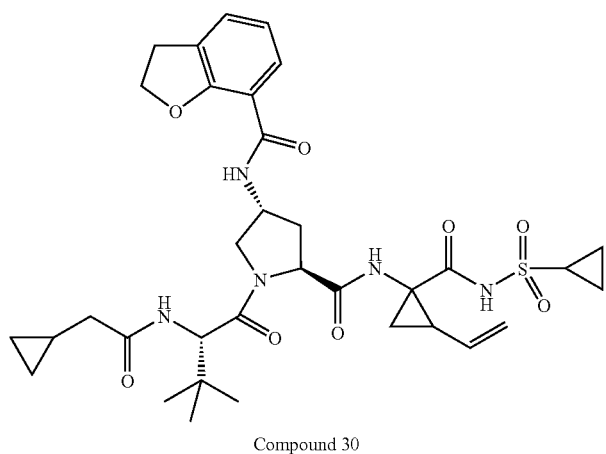

Example 45

Compound 31 was prepared as follows.

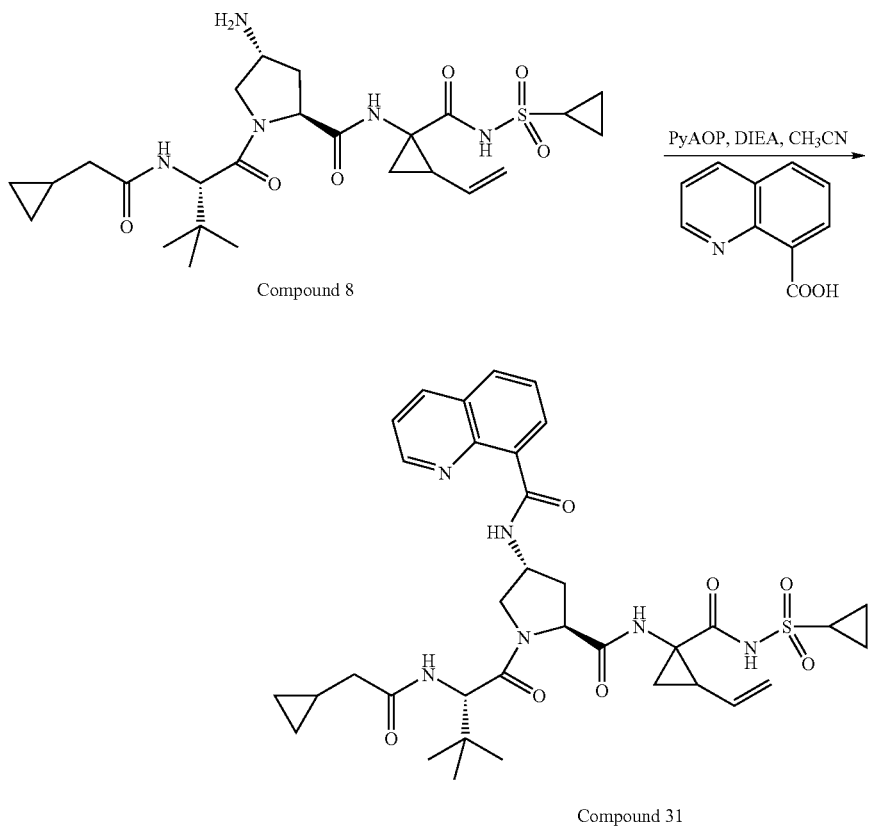

Following the general procedure of acid-amine coupling as shown in Example 23, Compound 8 (20 mg, 0.03 mmol) was treated with quinoline-8-carboxylic acid (7.8 mg, 0.045 mmol), DIEA (0.026 mL, 0.15 mmol) and the coupling reagent HOBt (6.9 mg, 0.045 mmol) and HBTU (17.1 mg, 0.045 mmol) in acetonitrile (3 mL). After purification by Prep.HPLC column, a colorless film as TFA salt was obtained as final 1:1 diastereomers (Compound 31) (14.6 mg, 60% yield).

(Compound 31, 48110-191): $^1$H NMR(CD$_3$OD, 300 MHz) δ: 9.11 (m, 1H), 8.83 (d, J=8.1 Hz, 1H), 8.70 (d, J=7.3 Hz, 1H), 8.32 (d, J=8.1 Hz, 1H), 7.8-7.9(m, 2H), 5.74 (m, 1H), 5.32 (m, 1H), 5.15 (m, 1H), 4.80 (m, 1H), 4.65 (m, 1H), 4.53 (m, 1H), 4.23 (m, 1H), 4.12 (m, 1H), 2.95 (m, 1H), 2.48 (m, 1H), 2.2-2.4 (m, 2H), 2.07 (d, J=7.0 Hz, 2H), 1.90 (dd, J=7.7 Hz, 5.5 Hz, 0.5H), 1.82 (dd, J=8.1 Hz, 5.5 Hz, 0.5H), 1.42 (m, 1H), 0.95-1.34 (m, 13H), 0.87 (m, 1H), 0.43 (m, 2H), 0.11 (m, 2H).

LC-MS (retention time: 1.457 minutes.), MS m/z 693(MH$^+$).

Example 46

Compound 32 was prepared as follows.

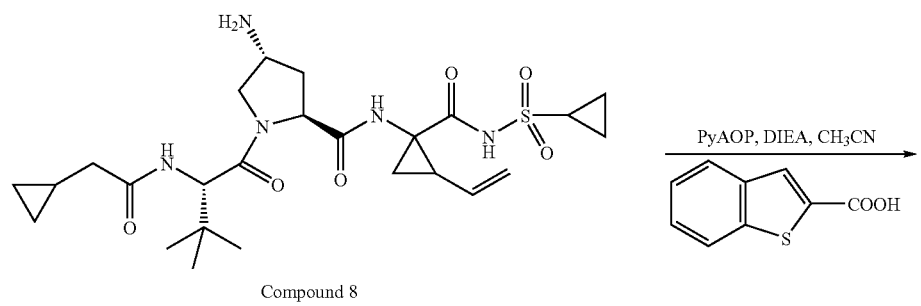

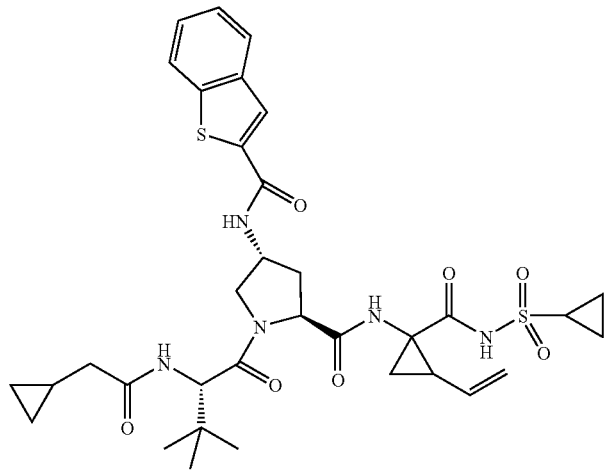

Compound 32

Following the general procedure of acid-amine coupling as shown in Example 23, Compound 8 (25 mg, 0.033 mmol) was treated with benzo[b]thiophene-2-carboxylic acid (8.0 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, a white solid was obtained as final 1:1 diastereomers (Compound 32) (17.8 mg, 68% yield).

(Compound 32, 48110-192A): $^1$H NMR(CD$_3$OD, 500 MHz) δ:8.12 (s, 1H), 7.90 (d, J=27.9 Hz, 1H), 7.83 (d, J=7.6 Hz, 1H), 7.42(m, 2H), 5.73 (m, 1H), 5.31 (m, 1H), 5.13 (m, 1H), 4.70 (m, 1H), 4.55 (m, 1H), 4.45(m, 1H), 4.14 (m, 1H), 4.05 (m, 1H), 2.95 (m, 1H), 2.43 (m, 1H), 2.15-2.28 (m, 4H), 1.89 (dd, J=7.9 Hz, 5.5 Hz, 0.5H), 1.81 (dd, J=7.9 Hz, 5.2 Hz, 0.5H), 1.40 (m, 1H), 1.0-1.33 (m, 14H), 0.53 (m, 2H), 0.22 (m, 2H). LC-MS (retention time: 1.740 minutes.), MS m/z 698(MH$^+$).

Example 47

Compound 33 was prepared as follows.

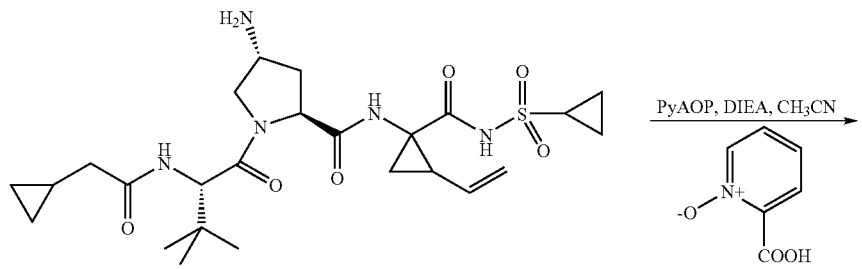

Compound 8

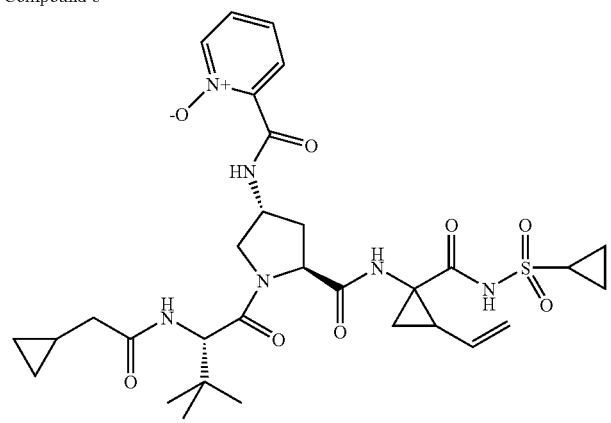

Compound 33

Following the general procedure of acid-amine coupling as shown in Example 23, Compound 8 (25 mg, 0.033 mmol) was treated with 1-oxy-pyridine-2-carboxylic acid (6.3 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, a colorless film was obtained as final 1:1 diastereomers (Compound 33) (9.2 mg, 37% yield).

(Compound 33, 48110-192B): $^1$H NMR(CD$_3$OD, 300 MHz) δ: 8.35 (m, 2H), 7.64(m, 2H), 5.76(m, 1H), 5.31 (m, 1H), 5.14 (m, 1H), 4.76 (m, 1H), 4.63 (m, 1H), 4.43(m, 1H), 4.08 (m, 2H), 2.96 (m, 1H), 2.02-2.43(m, 5H), 1.89 (dd, J=8.1 Hz, 5.9 Hz, 0.5H), 1.80 (dd, J=7.7 Hz, 5.1 Hz, 0.5H), 1.43 (m, 1H), 0.85-1.35 (m, 14H), 0.49 (m, 2H), 0.15 (m, 2H). LC-MS (retention time: 1.417 minutes.), MS m/z 659(MH$^+$).

Example 48

Compound 34 was prepared as follows.

Following the general procedure of acid-amine coupling as shown in Example 23, Compound 8 (25 mg, 0.033 mmol) was treated with 1-oxy-quinoline-2-carboxylic acid (8.5 mg, 0.045 mmol), DIEA (0.0163 mL, 0.094 mmol) and the coupling reagent PyAOP (29.3 mg, 0.056 mmol) in acetonitrile (3 mL). After purification by Prep.HPLC column, a colorless film was obtained as final 1:1 diastereomers (Compound 34) (16 mg, 60% yield).

(Compound 34, 48110-192C): $^1$H NMR(CD$_3$OD, 300 MHz) δ: 8.70 (d, J=8.8 Hz, 1H), 8.29 (d, J=8.8 Hz, 1H), 8.09(m, 2H), 7.91 (m, 1H), 7.82 (m, 1H), 5.76 (m, 1H), 5.32 (m, 1H), 5.14 (m, 1H), 4.80 (m, 1H), 4.66 (m, 1H), 4.50(m, 1H), 4.05-4.20 (m, 2H), 2.96 (m, 1H), 2.19-2.51 (m, 3H), 2.08 (m, 2H), 1.89 (dd, J=7.7 Hz, 5.5 Hz, 0.5H), 1.81 (dd, J=8.1 Hz, 5.5 Hz, 0.5H), 1.45 (m, 1H), 0.95-1.32 (m, 13H), 0.87 (m, 1H), 0.40 (m, 2H), 0.10 (m, 2H). LC-MS (retention time: 1.577 minutes.), MS m/z 709(MH$^+$).

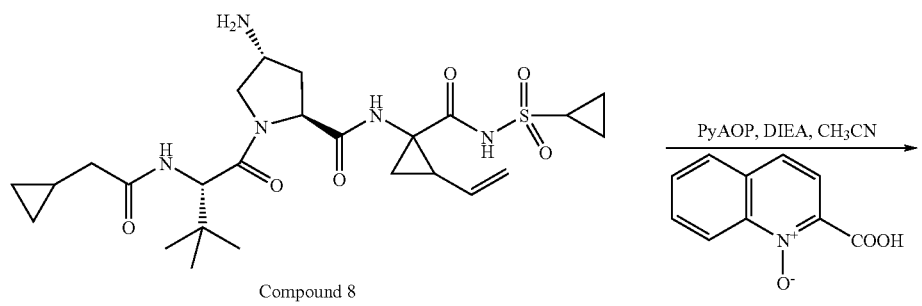

Compound 8

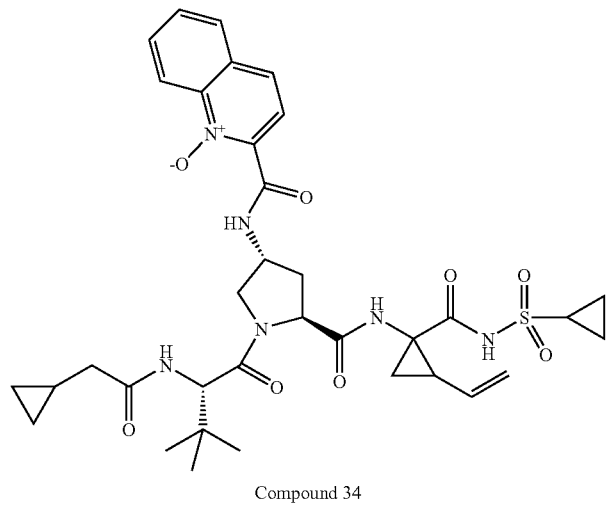

Compound 34

Example 49

Compound 35 was prepared as follows.

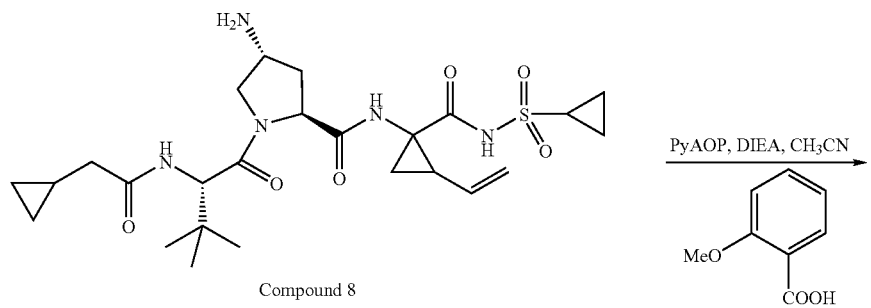

Compound 8

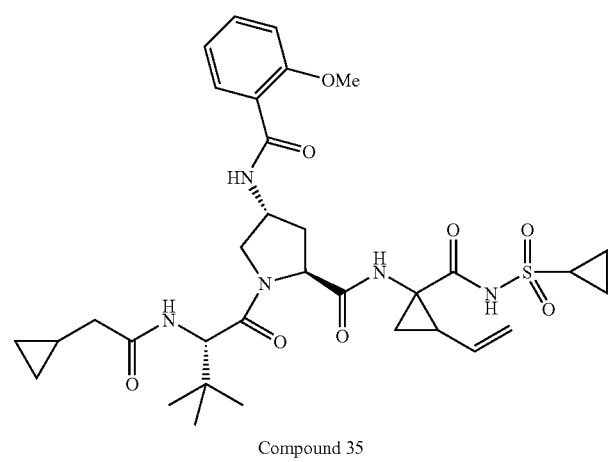

Compound 35

Following the general procedure of acid-amine coupling as shown in Example 23, Compound 8 (20 mg, 0.03 mmol) was treated with 2-methoxy-benzolic acid (6.85 mg, 0.045 mmol), DIEA (0.021 mL, 0.12 mmol) and the coupling reagent HOBt (6.9 mg, 0.045 mmol) and HBTU (17.1 mg, 0.045 mmol) in acetonitrile (3 mL). After purification by Prep.HPLC column, a colorless film was obtained as final 1:1 diastereomers (Compound 35) (12.3 mg, 61% yield).

(Compound 35, 48110-193A): LC-MS (retention time: 1.507 minutes.), MS m/z 672(MH$^+$).

Example 50

Compound 36 was prepared as follows.

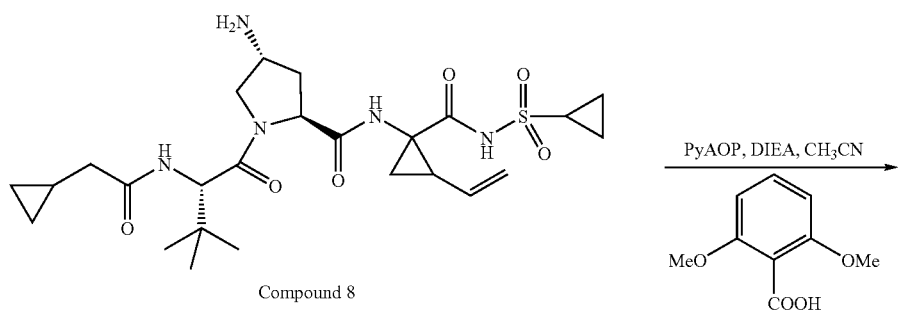

Compound 8

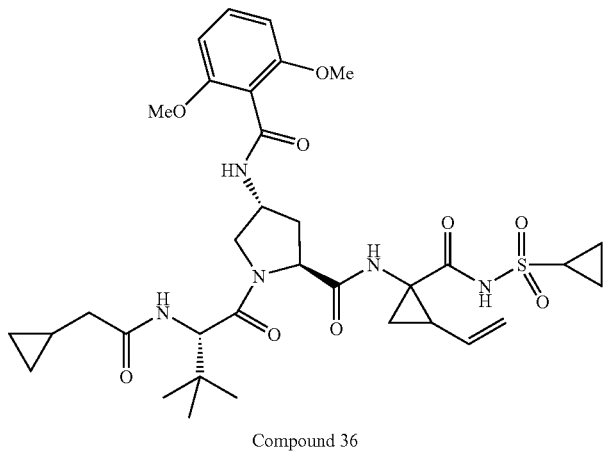

Compound 36

Following the general procedure of acid-amine coupling as shown in Example 23, Compound 8 (20 mg, 0.03 mmol) was treated with 2,6-dimethoxybenzoic acid (8.2 mg, 0.045 mmol), DIEA (0.021 mL, 0.12 mmol) and the coupling reagent HOBt (6.9 mg, 0.045 mmol) and HBTU (17.1 mg, 0.045 mmol) in acetonitrile (3 mL). After purification by Prep.HPLC column, a colorless film was obtained as final 1:1 diastereomers (Compound 36) (17.0 mg, 81% yield). (Compound 36, 48110-193B): LC-MS (retention time: 1.460 minutes.), MS m/z 702(MH$^+$).

Example 51

Compound 37 was prepared as follows.

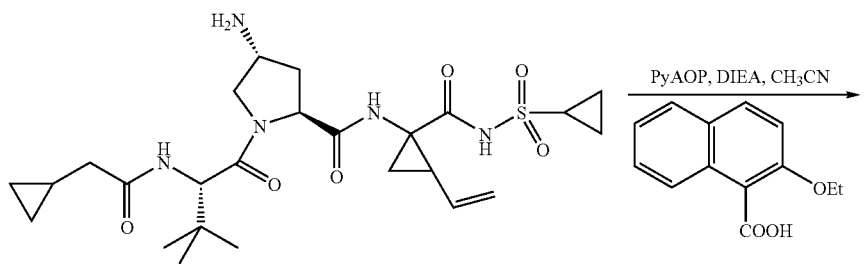

Compound 8

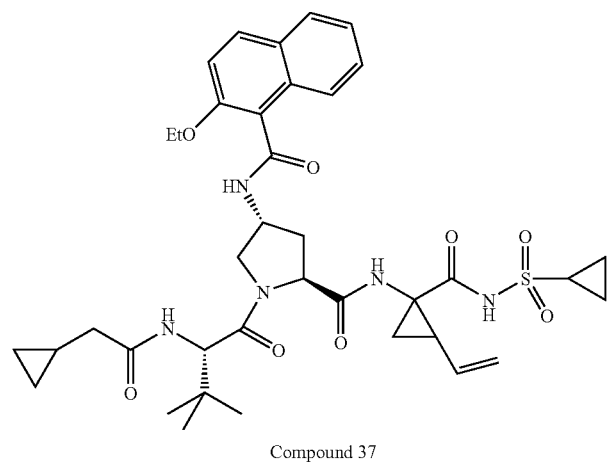

Compound 37

Following the general procedure of acid-amine coupling as shown in Example 23, Compound 8 (20 mg, 0.03 mmol) was 2-ethoxy-naphthalene-1-carboxylic acid (9.73 mg, 0.045 mmol), DIEA (0.021 mL, 0.12 mmol) and the coupling reagent HOBt (6.9 mg, 0.045 mmol) and HBTU (17.1 mg, 0.045 mmol) in acetonitrile (3 mL). After purification by Prep.HPLC column, a colorless film was obtained as final 1:1 diastereomers (Compound 37) (9.5 mg, 43% yield). (Compound 37, 48110-193C): $^1$H NMR(CD$_3$OD, 500 MHz) δ: 7.92 (d, J=9.2 Hz, 1H), 7.82 (d, J=8.2 Hz, 1H), 7.75 (d, J=8.5 Hz, 1H), 7.50 (m, 1H), 7.40 (d, J=9.2 Hz, 1H), 7.36 (m, 1H), 5.76 (m, 1H), 5.33 (m, 1H), 5.14 (m, 1H), 4.85 (m, 1H), 4.60 (m, 1H), 4.41(m, 1H), 4.25 (q, J=7.0 Hz, 2H), 4.14 (m, 1H), 4.02 (m, 1H), 2.95 (m, 1H), 2.45 (m, 1H), 2.23-2.34 (m, 2H), 2.07 (m, 2H), 1.90 (dd, J=8.2 Hz, 5.5 Hz, 0.5H), 1.81 (dd, J=8.2 Hz, 5.2 Hz, 0.5H), 1.43 (m, 1H), 1.42 (t, J=7.0 Hz, 3H), 0.97-1.32 (m, 13H), 0.86(m, 1H), 0.44 (m, 2H), 0.11 (m, 2H). LC-MS (retention time: 1.637 minutes.), MS m/z 736(MH$^+$).

Example 52

Compound 38 was prepared as follows.

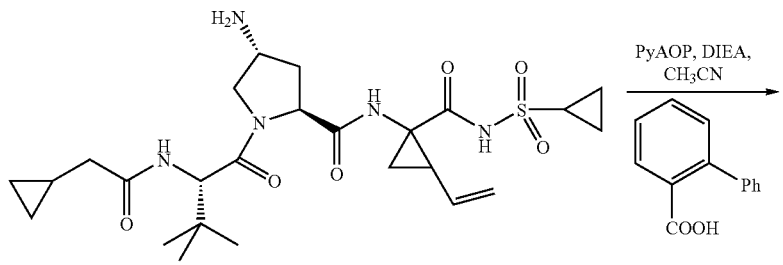

Compound 8

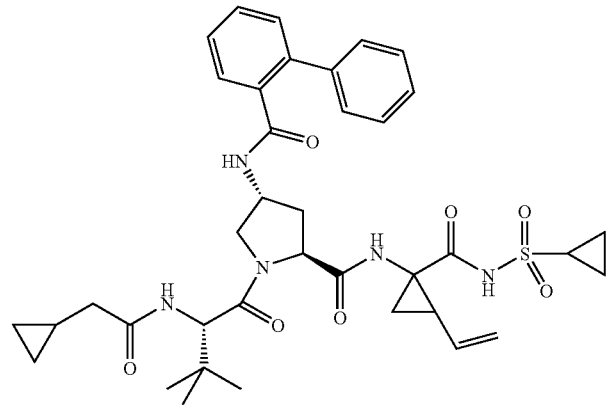

Compound 38

Following the general procedure of acid-amine coupling as shown in Example 23, Compound 8 (20 mg, 0.03 mmol) was treated with biphenyl-2-carboxylic acid (8.92 mg, 0.045 mmol), DIEA (0.021 mL, 0.12 mmol) and the coupling reagent HOBt (6.9 mg, 0.045 mmol) and HBTU (17.1 mg, 0.045 mmol) in acetonitrile (3 mL). After purification by Prep.HPLC column, a colorless film was obtained as final 1:1 diastereomers (Compound 38) (17.3 mg, 80% yield). (Compound 38, 48110-193D): LC-MS (retention time: 1.680 minutes.), MS m/z 718(MH$^+$).

Example 53

Compound 39 was prepared as follows.

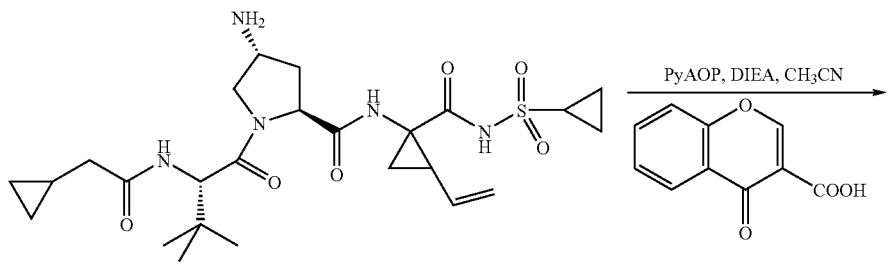

Compound 8

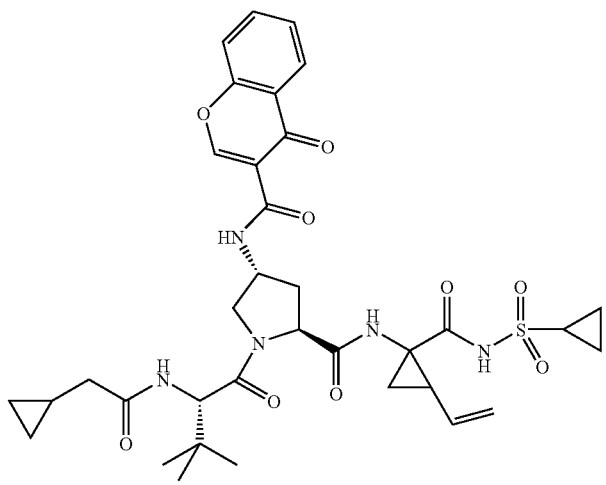

Compound 39

Following the general procedure of acid-amine coupling as shown in Example 23, Compound 8 (20 mg, 0.03 mmol) was treated with chromone-3-carboxylic acid (6.85 mg, 0.045 mmol), DIEA (0.013 mL, 0.075 mmol) and the coupling reagent PyAOP (23.5 mg, 0.045 mmol) in acetonitrile (3 mL). After purification by Prep.HPLC column, an off-white solid was obtained as final 1:1 diastereomers (Compound 39) (14.5 mg, 68% yield). (Compound 39, 48110-195A): LC-MS (retention time: 1.570 minutes.), MS m/z 710(MH$^+$).

Example 54

Compound 40 was prepared as follows.

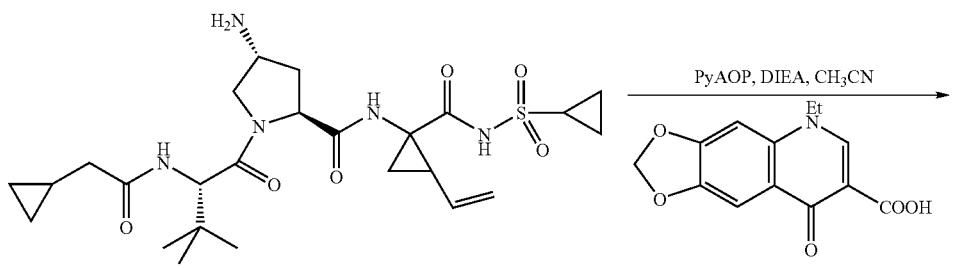

Compound 8

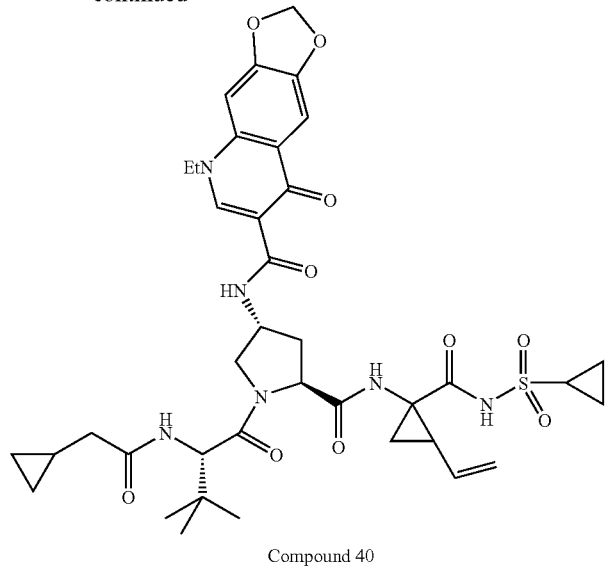

Compound 40

Following the general procedure of acid-amine coupling as shown in Example 23, Compound 8 (20 mg, 0.03 mmol) was treated with oxolinic acid (9.40 mg, 0.045 mmol), DIEA (0.013 mL, 0.075 mmol) and the coupling reagent PyAOP (23.5 mg, 0.045 mmol) in acetonitrile (3 mL). After purification by Prep.HPLC column, a white solid as TFA salt was obtained as final 1:1 diastereomers (Compound 40) (8.0 mg, 30% yield). (Compound 40, 48110-195B): LC-MS (retention time: 1.563 minutes.), MS m/z 781(MH$^+$).

Example 55

Compound 41 was prepared as follows.

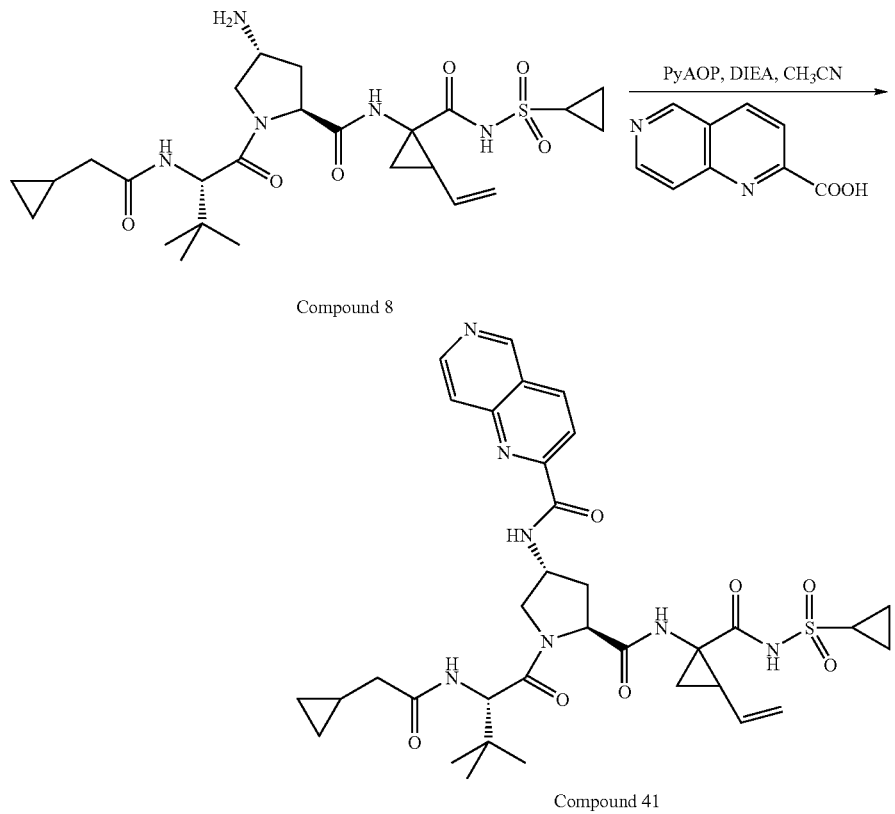

Compound 41

Following the general procedure of acid-amine coupling as shown in Example 23, Compound 8 (20 mg, 0.03 mmol) was [1,6]naphthyridine-2-carboxylic acid (7.8 mg, 0.045 mmol), DIEA (0.026 mL, 0.15 mmol) and the coupling reagent HOBt (6.9 mg, 0.045 mmol) and HBTU (17.1 mg, 0.045 mmol) in acetonitrile (3 mL). After purification by Prep.HPLC column, a yellowish solid as TFA salt was obtained as final 1:1 diastereomers (Compound 41) (15 mg, 62% yield). (Compound 41, 50177-003): LC-MS (retention time: 1.537 minutes.), MS m/z 694(MH+).

Example 56

Compound 42 was prepared as follows.

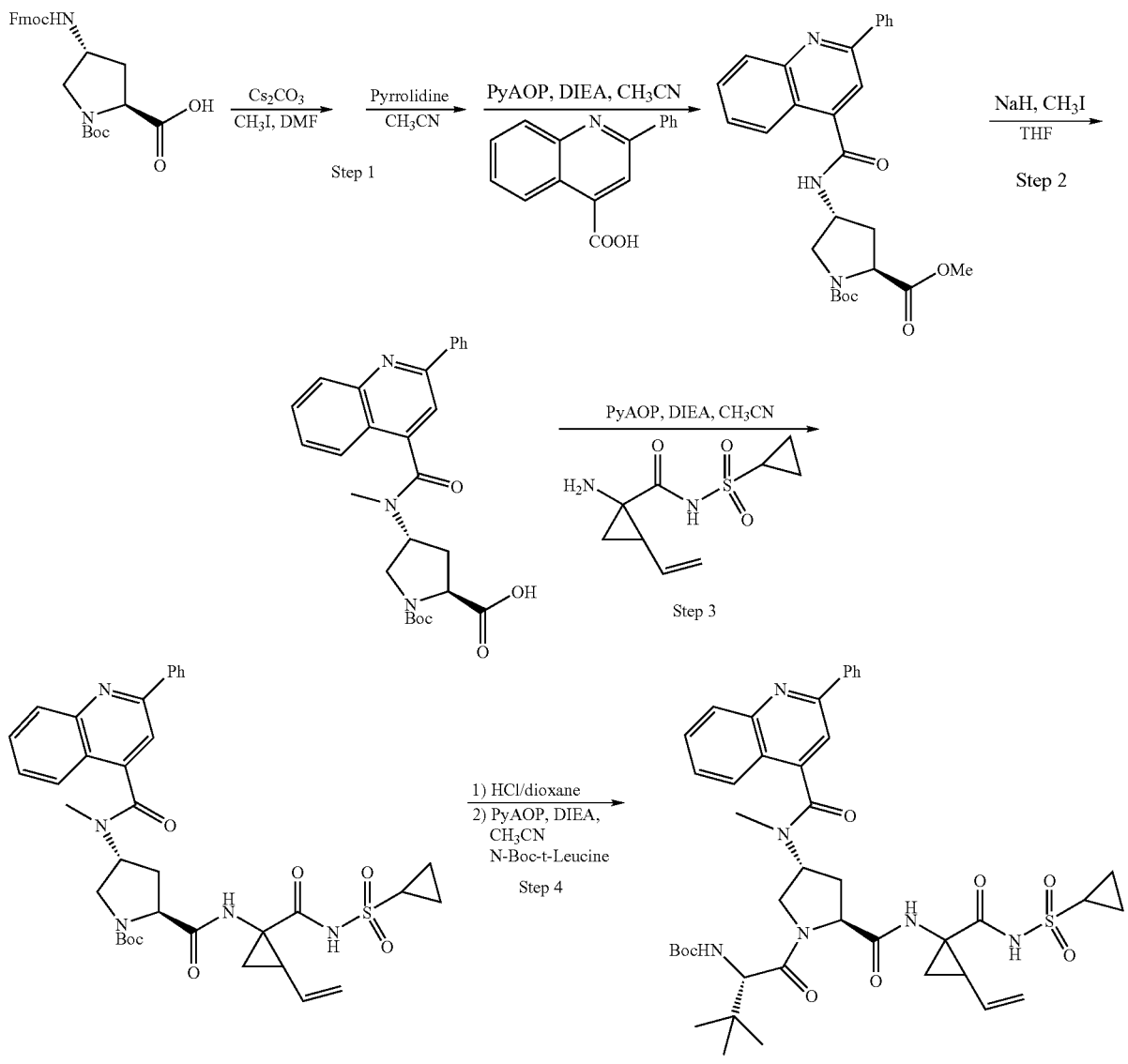

Step 1:

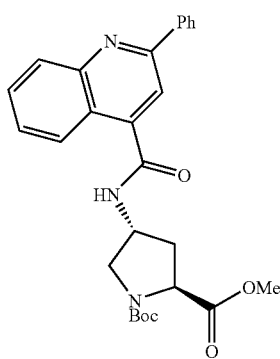

To a solution of Fmoc(2S,4R)-4-amino-1-Boc-pyrrolidine-2-carboxylic acid (300 mg, 0.663 mmol) in DMF (5 mL), cesium carbonate (475 mg, 1.459 mmol) and methyl iodide (0.1 mL, 1.658 mmol) were added. The reaction mixture was stirred at room temperature for overnight. Then it was treated with water and extracted with ethyl acetate. The organic layer was separated, washed with brine and dried over $MgSO_4$. Evaporation of solvent gave a colorless thick oil. It was then dissolved in acetonitrile (5 mL) and pyrrolidine (1 mL) was added. The reaction mixture was stirred at room temperature for 3 hours. LC/MS shown completion of deprotection of Fmoc. It was then concentrated and put on high vacuum to pump out excess pyrrolidine. Then it was redissolved in acetonitrile (5 mL). PyAOP (519 mg, 0.995 mmol), 2-phenyl-4-quinolinecarboxylic acid (198 mg, 0.796 mmol) and DIEA (0.17 mL, 0.995 mmol) were added. This reaction mixture was stirred at room temperature for overnight. It was then concentrated down, washed with water and extracted with ethyl acetate. The organic layer was separated, washed with brine and dried over $MgSO_4$, and filtered. Evaporation of solvent gave yellowish oil as crude product. It was then purified by flash column chromatography (silica gel, 2:1 ethyl acetate:hexanes) to provide a light yellow solid (0.22 g, 70% yield). (48110-177 & 48110-178): $^1$H NMR(CDCl$_3$, 300 MHz) δ: 8.07-8.26 (m, 4H), 7.87 (s, 1H), 7.77 (t, J=8.1 Hz, 1H), 7.44-7.65 (m, 4H), 6.30(m, br, 1H), 4.88 (m, 1H), 4.44 (m, 1H), 3.98 (m, 1H), 3.78 (s, 3H), 3.54 (m, 1H), 2.35-2.50 (m, 2H), 1.34-1.5 (m, 9H). LC-MS (retention time: 1.530 minutes.), MS m/z 476(MH$^+$).

Step 2:

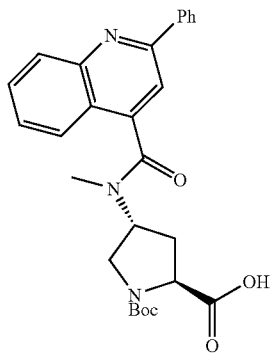

To a solution of 4-[(2-Phenyl-quinoline-4-carbonyl)-amino]-pyrrolidine-1,2-dicarboxylic acid 1-tert-butyl ester 2-methyl ester (95 mg, 0.2 mmol) in THF (10 mL), NaH (10 mg in 60% suspension in mineral oil, 0.24 mmol) was added. The reaction mixture was stirred at room temperature for an hour. Then methyl iodide (0.019 mL, 0.3 mmol) was added. The reaction mixture was stirred at room temperature for overnight. Then it was quenched with water, added 1N HCl and extracted with ethyl acetate. The organic layer was separated, washed with brine and dried over MgSO4. Evaporation of solvent gave a yellowish solid (90 mg, 95% yield). 48110-180: $^1$H NMR(DMSO-d$_6$, 300 MHz) δ: exists in rotamers, broad peaks. LC-MS (retention time: 1.460 minutes.), MS m/z 476(MH$^+$).

Step 3:

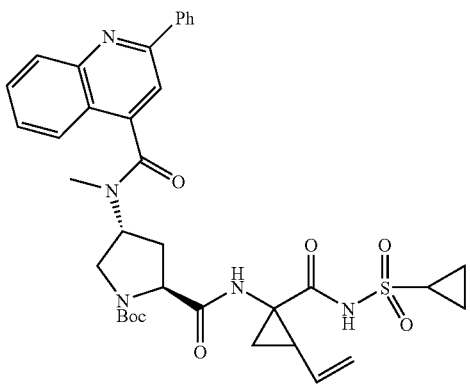

To a solution 4-[methyl-(2-phenyl-quinoline-4-carbonyl)-amino]-pyrrolidine-1,2-dicarboxylic acid 1-tert-butyl ester (80 mg, 0.168 mmol) in CH$_3$CN (10 mL) was added (1-cyclopropane-sulfonylaminocarbonyl-2-vinyl-cyclopropyl)-carbamic acid trifluoroacetic acid salt (75 mg, 0.219 mmol), DIEA (0.073 mL, 0.42 mmol) and the coupling reagent PyAOP (131 mg, 0.252 mmol). The solution was stirred at room temperature overnight. Then it was concentrated, washed with water and extracted with ethyl acetate twice. The combined organic layers were washed with brine, dried over MgSO$_4$, filtered, and concentrated to give the crude product which was purified by Prep. TLC plate (eluted with dichloromethane with 5% methanol) to provide a white solid as a mixture of diastereoisomers (62 g, 54% yield). (48110-183): $^1$H NMR(CD$_3$OD, 300 MHz) δ: exists in rotamers, broad peaks. LC-MS (retention time: 2.765 minutes.), MS m/z 688 (MH$^+$).

Step 4:

Compound 42

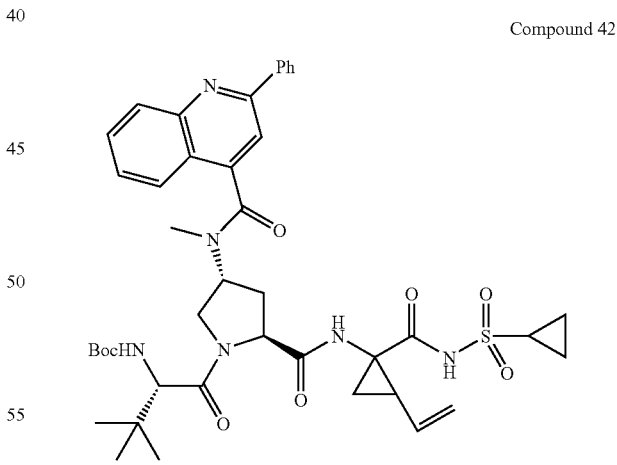

To 2-(1-cyclopropanesulfonylaminocarbonyl-2-vinyl-cyclopropylcarbamoyl)-4-[methyl-(2-phenyl-quinoline-4-carbonyl)-amino]-pyrrolidine-1-carboxylic acid tert-butyl ester (50 mg, 0.0727 mmol) was added 3 mL of 4N HCl in dioxane. The mixture was stirred at room temperature overnight. It was then concentrated and dissolved in CH$_3$CN (5 mL). N-Boc-tert-leucine (20.2 mg, 0.0873 mmol), DIEA (0.032 mL, 0.182 mmol) and the coupling reagent PyAOP (56.9 mg, 0.109 mmol) were added. The solution was stirred at room

Example 57

Compound 43 was prepared as follows.

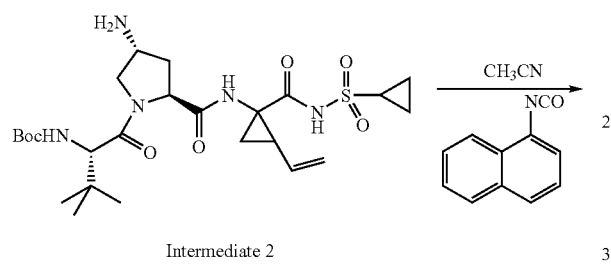

Intermediate 2

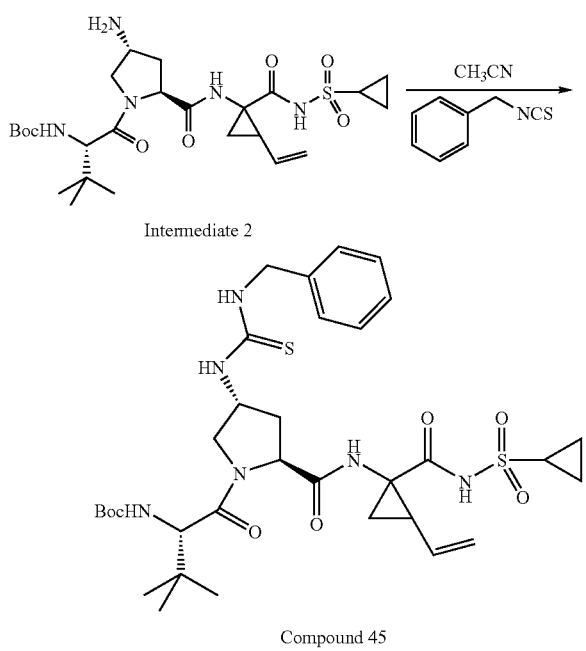

Compound 43

To a solution of intermediate 2 (40 mg, 0.072 mmol) in acetonitrile (3 mL), 1-naphthylisocynate (18.3 mg, 0.108 mmol) was added. The reaction mixture was stirred at room temperature for 4 hours. Then the mixture was concentrated and the residue was purified by Prep. HPLC column to provide white solid as 1:1 diastereomers (Compound 43) (15 mg, 29% yield). (48110-149): $^1$H NMR(CD$_3$OD, 500 MHz) δ: diastereomer mixture, broad peaks. LC-MS (retention time: 1.777 minutes.), MS m/z 725 (MH$^+$).

Example 58

Compound 44 was prepared as follows.

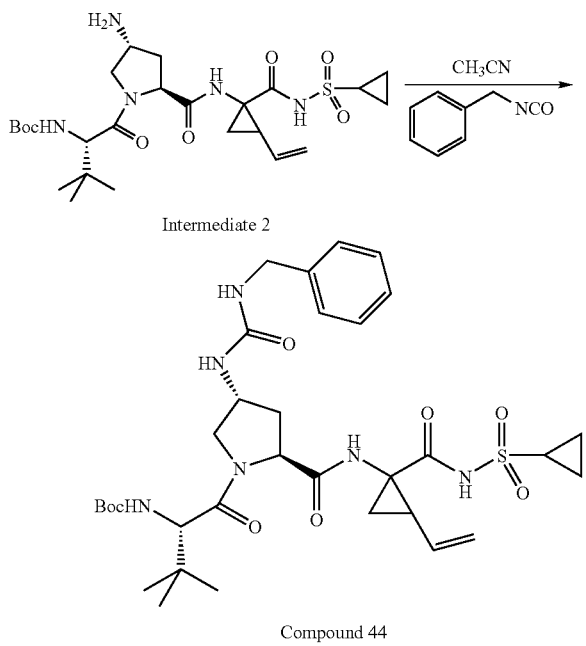

To a solution of intermediate 2 (40 mg, 0.072 mmol) in acetonitrile (3 mL), benzyl isocynate (0.013 mL, 0.108 mmol) was added. The reaction mixture was stirred at room temperature for 4 hours. Then the mixture was concentrated and the residue was purified by Prep. HPLC column to provide white solid as 1:1 diastereomers (Compound 44) (3.8 mg, 7.7% yield). (Compound 44, 48110-150A): $^1$H NMR (CD$_3$OD, 500 MHz) δ: diastereomer mixture, broad peaks. LC-MS (retention time: 1.980 minutes.), MS m/z 689 (MH$^+$).

Example 59

Compound 45 was prepared as follows.

To a solution of intermediate 2 (40 mg, 0.072 mmol) in acetonitrile (3 mL), benzyl isothiocynate (0.014 mL, 0.108 mmol) was added. The reaction mixture was stirred at room temperature for 4 hours. Then the mixture was concentrated and the residue was purified by Prep. HPLC column to provide white solid as 1:1 diastereomers (Compound 45) (5.3 mg, 10.4% yield). (Compound 45, 48110-150B): $^1$H NMR (CD$_3$OD, 500 MHz) δ: diastereomer mixture, broad peaks. LC-MS (retention time: 2.083 minutes.), MS m/z 705 (MH$^+$).

Example 60

Compound 46 was prepared as follows.

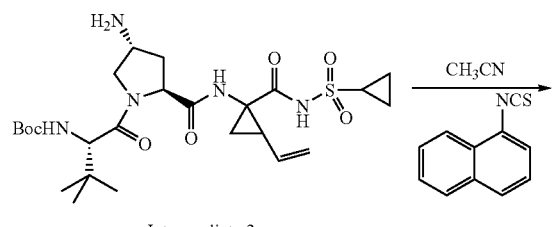

Intermediate 2

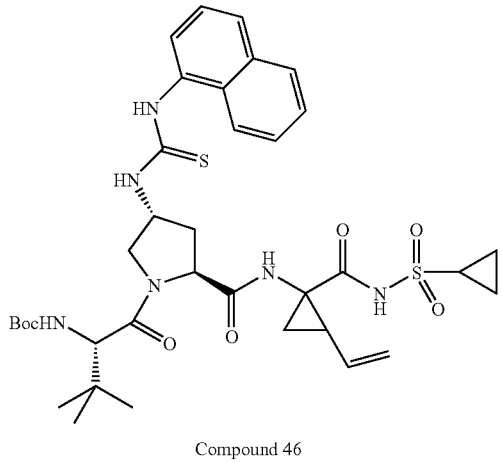

Compound 46

To a solution of intermediate 2 (40 mg, 0.072 mmol) in acetonitrile (3 mL), 1-naphthyl isothiocyanate (20 mg, 0.108 mmol) was added. The reaction mixture was stirred at room temperature for 4 hours. Then the mixture was concentrated and the residue was purified by flash column chromatography (silica gel, 2:1 ethyl acetate:hexanes) to provide white solid as 1:1 diastereomers (Compound 46) (9 mg, 17% yield). (Compound 46, 48110-152): $^1$H NMR(CD$_3$OD, 300 MHz) δ: diastereomer mixture. LC-MS (retention time: 1.743 minutes.), MS m/z 741 (MH$^+$).

Example 61

Compound 47 was prepared as follows.

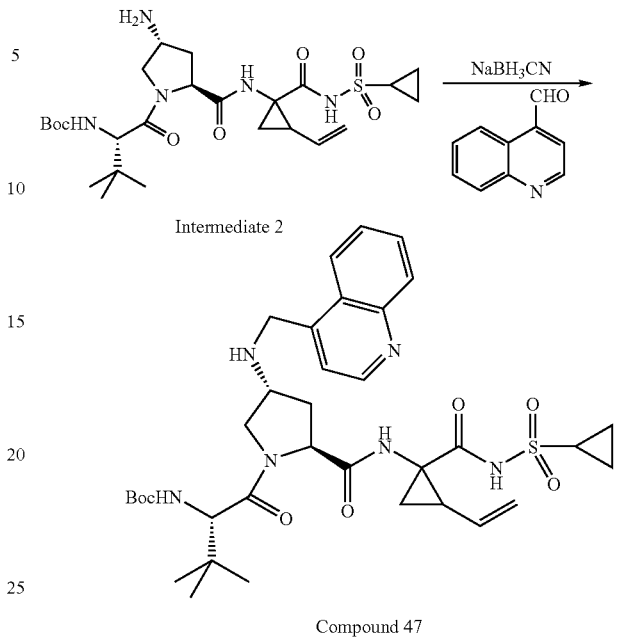

Compound 47

To a solution of intermediate 2 (40 mg, 0.072 mmol) in 1:1 CH$_2$Cl$_2$:methanol (5 mL), 4-quinoline carboxaldehyde (17 mg, 0.108 mmol) was added. The reaction mixture was stirred at 70° C. for 1 hour. Then sodium cyanoborohydride (6.8 mg, 0.108 mmol) was added. The reaction mixture was heated at 70° C. for overnight. Then it was concentrated and the residue was purified by Prep. TLC plate (eluted with CH$_2$Cl$_2$ with 5% methanol) to provide yellowish solid as 1:1 diastereomers (Compound 47) (17 mg, 34% yield). (Compound 47, 48110-143): $^1$H NMR(CD$_3$OD, 500 MHz) δ: diastereomer mixture, broad peaks. LC-MS (retention time: 1.337 minutes.), MS m/z 697 (MH$^+$).

Example 62

Compound 48 was prepared as follows.

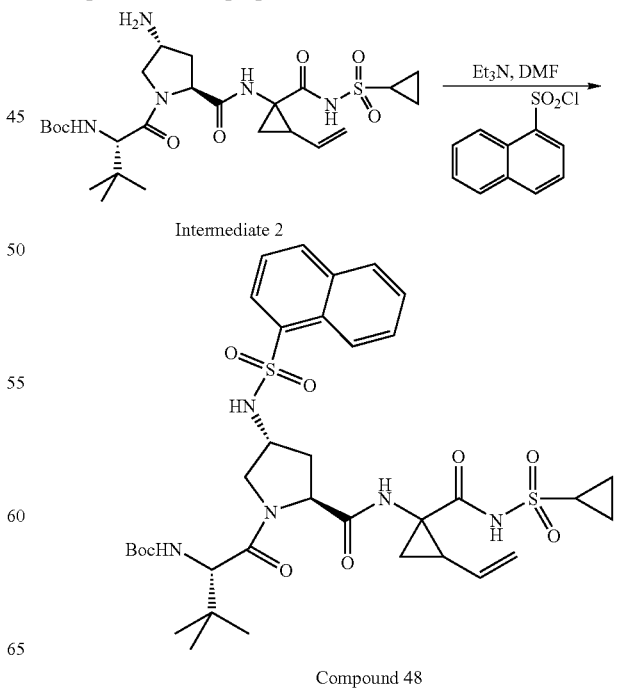

Compound 48

To a solution of intermediate 2 (40 mg, 0.072 mmol) in DMF (3 mL), 1-naphthalenesulfonyl chloride (24.5 mg, 0.108 mmol) and triethylamine (0.015 mL, 0.108 mmol) were added. The reaction mixture was stirred at room temperature for overnight. Then it was concentrated and the residue was purified by Prep. HPLC column to give white solid as 1:1 diastereomers (Compound 48) (4 mg, 7.4% yield). (Compound 48, 48110-151): $^1$H NMR(CD$_3$OD, 500 MHz) δ: diastereomer mixture. LC-MS (retention time: 2.047 minutes.), MS m/z 768 (M+Na$^+$).

Example 63

Compound 49 was prepared as follows.

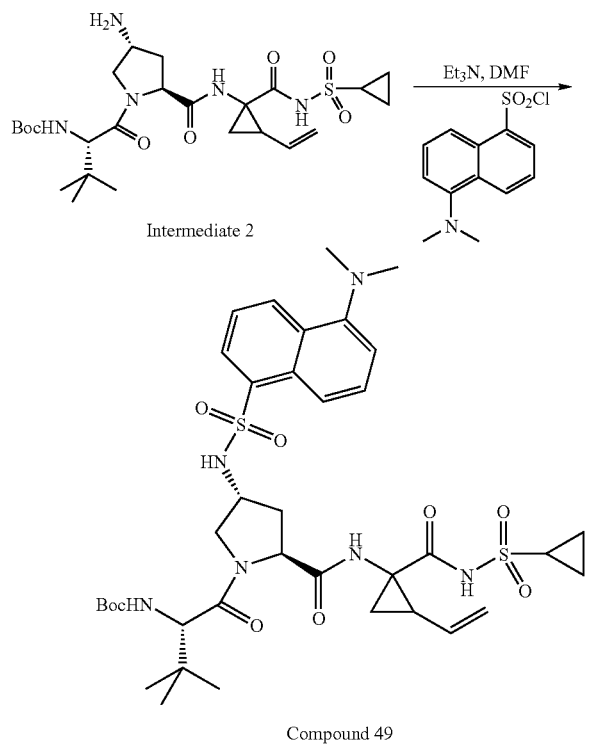

Compound 49

To a solution of intermediate 2 (40 mg, 0.072 mmol) in DMF (3 mL), dansyl chloride (29.1 mg, 0.108 mmol) and triethylamine (0.015 mL, 0.108 mmol) were added. The reaction mixture was stirred at room temperature for overnight. Then it was concentrated and the residue was purified by Prep. HPLC column to give yellowish solid as 1:1 diastereomers (Compound 49) (4.1 mg, 7.2% yield). (Compound 49, 48110-148): $^1$H NMR(CD$_3$OD, 500 MHz) δ: diastereomer mixture, broad peaks. LC-MS (retention time: 1.727 minutes.), MS m/z 789 (MH$^+$).

Example 64

Compound 50 was prepared as follows.

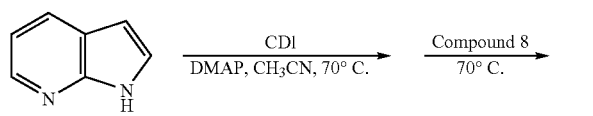

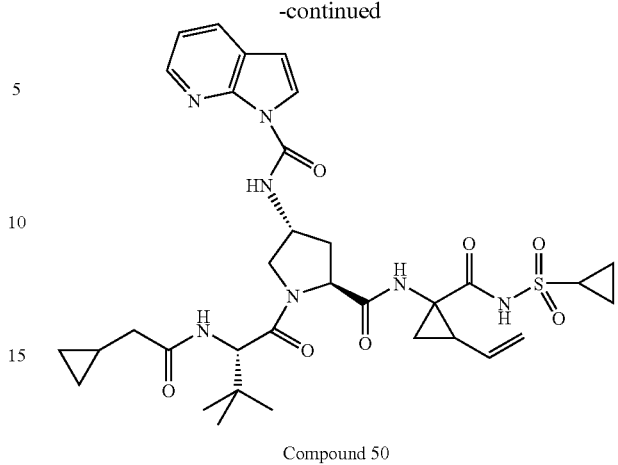

Compound 50

To a solution of 7-azaindole (7.09 mg, 0.06 mmol) in acetonitrile (5 mL), CDI (10.7 mg, 0.066 mmol) and DMAP (5 mg) were added. The reaction mixture was stirred at 70° C. for 8 hours. Then Compound 8 (20 mg, 0.03 mmol) was added. The resulting mixture was heated at 70° C. for overnight. Then it was cooled, concentrated and purified by Prep. HPLC to provide yellowish film as 1:1 diastereomers (Compound 50)(4.1 mg, 17% yield). (Compound 50, 48110-196A): $^1$H NMR(CD$_3$OD, 300 MHz) δ: 8.31 (d, J=4.4 Hz, 1H), 8.08 (d, J=7.7 Hz, 1H), 7.93 (d, J=3.7 Hz, 1H), 7.28 (dd, J=7.7 Hz, 4.7 Hz, 1H), 6.66 (d, J=3.7 Hz, 1H), 5.75 (m, 1H), 5.32(m, 1H), 5.14 (m, 1H), 4.76 (m, 1H), 4.69 (m, 1H), 4.52(m, 1H), 4.20 (m, 1H), 4.09 (m, 1H), 2.95 (m, 1H), 2.45 (m, 1H), 2.20-2.36 (m, 2H), 2.04 (d, J=7.0 Hz, 2H), 1.90 (dd, J=7.7 Hz, 5.9 Hz, 0.5H), 1.80 (dd, J=8.1 Hz, 5.5 Hz, 0.5H), 1.44 (m, 1H), 0.95-1.34 (m, 13H), 0.86(m, 1H), 0.41 (m, 2H), 0.10 (m, 2H).

LC-MS (retention time: 1.570 minutes.), MS m/z 682(MH$^+$).

Example 65

Compound 51 was prepared as follows.

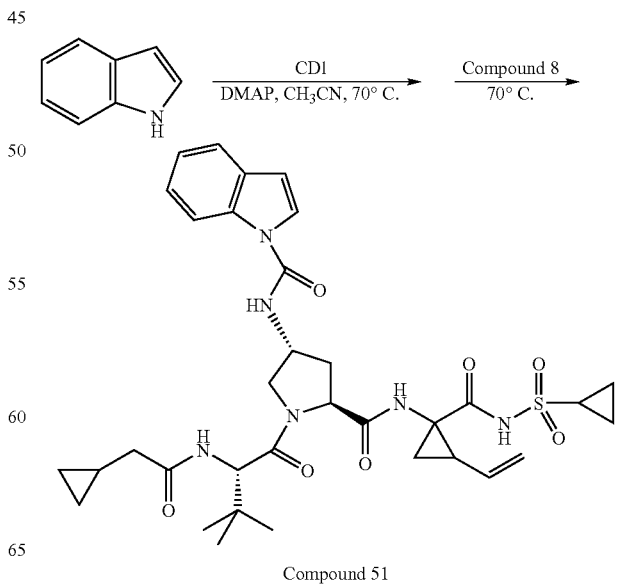

Compound 51

To a solution of indole (11 mg, 0.0935 mmol) in acetonitrile (5 mL), CDI (15.2 mg, 0.0935 mmol) and DMAP (5 mg) were added. The reaction mixture was stirred at 70° C. for 8 hours. Then Compound 8 (25 mg, 0.0374 mmol) was added. The resulting mixture was heated at 70° C. for overnight. Then it was cooled, concentrated and purified by Prep. HPLC to provide white solid as 1:1 diastereomers (Compound 51) (12 mg, 47% yield). (Compound 51, 50177-007): $^1$H NMR (CD$_3$OD, 300 MHz) δ 8.21 (d, J=8.1 Hz, 1H), 7.84 (d, J=3.3 Hz, 1H), 7.55 (d, J=7.7 Hz, 1H), 7.25 (t, J=7.3 Hz, 1H), 7.17 (t, J=7.3 Hz, 1H), 6.60 (d, J=3.7 Hz, 1H), 5.73 (m, 1H), 5.33 (d, J=16.8 Hz, 0.5H), 5.30 (d, J=16.8 Hz, 0.5H), 5.13 (m, 1H), 4.65 (m, 1H), 4.54 (m, 1H), 4.46 (m, 1H), 4.19 (m, 1H), 4.06 (m, 1H), 2.94 (m, 1H), 2.47 (m, 1H), 2.25 (m, 2H), 2.18 (d, J=7.0 Hz, 2H), 1.90 (dd, J=8.1 Hz, 5.5 Hz, 0.5H), 1.81 (dd, J=7.3 Hz, 5.1 Hz, 0.5H), 1.40 (m, 1H), 0.92-1.32 (m, 14H), 0.52 (m, 2H), 0.19 (m, 2H).

LC-MS (retention time: 1.647 minutes.), MS m/z 681 (MH$^+$).

Example 66

Compound 52 was prepared as follows.

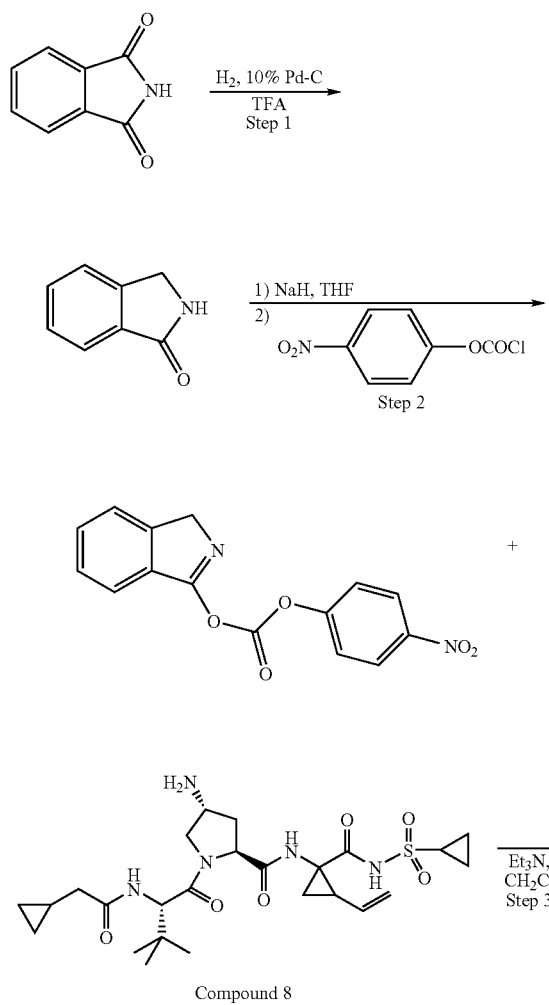

Compound 8

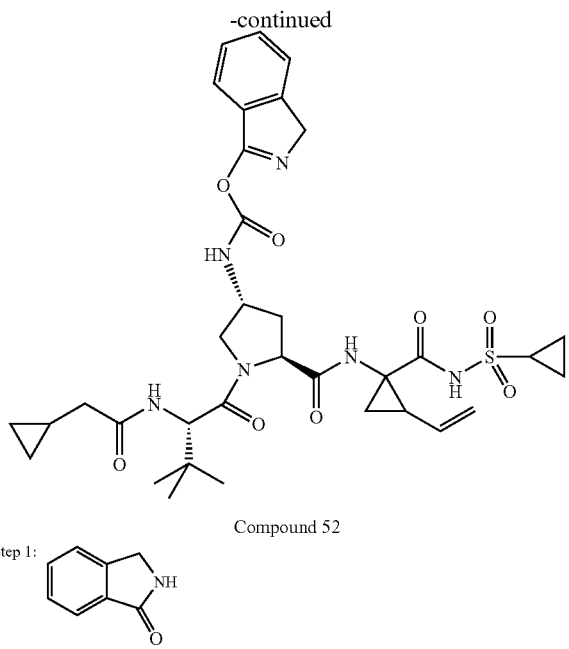

Compound 52

Step 1:

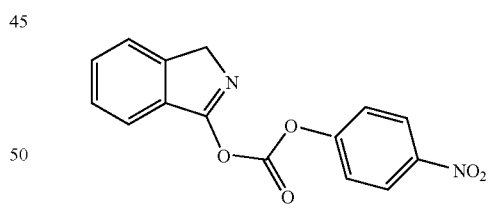

A solution of phthalimide (1.0 g, 6.8 mmol) and TFA (5 mL) in ethyl acetate (100 mL) was added 10% Pd—C (1 g). The reaction mixture was hydrogenated at 55 psi for 2 days. Catalyst was then filtered through diatomaceous earth (Celite®) and the filtrate was concentrated to give yellowish solid as crude product (0.37 g). 120 mg of them was then purified by Prep. TLC (eluted with dichloromethane) to give pure 2,3-dihydro-isoindol-1-one (65 mg).

50177-008: $^1$H NMR(CDCl$_3$, 300 MHz) δ 7.88 (d, J=7.2 Hz, 1H), 7.58 (t, J=7.3 Hz, 1H), 7.49 (m, 2H), 6.72 (s, br, 1H), 4.47 (s, 2H).

LC-MS (retention time: 0.737 minutes.), MS m/z 134(MH$^+$).

Step 2:

To a suspension of NaH (18 mg, 60% dispension in mineral oil, 0.454 mmol) in THF (10 mL), 2,3-dihydro-isoindol-1-one (55 mg, 0.413 mmol) was added. The reaction mixture was stirred at room temperature for 1 hours. The p-nitrophenyl chloroformate (91.5 mg, 0.454 mmol) was added and the reaction mixture was stirred at room temperature for overnight. Solvent was concentrated and the residue was washed with methanol. White solid was collected as pure product carbonic acid 3H-isoindol-1-yl ester 4-nitro-phenyl ester (37 mg, 30% yield).

50177-014: $^1$H NMR(CDCl$_3$, 500 MHz) δ 8.31 (d, J=7.1 Hz, 2H), 7.99 (d, J=7.7 Hz, 1H), 7.58 (t, J=7.6 Hz, 1H), 7.57 (m, 2H), 7.48 (d, J=7.1 Hz, 2H), 4.98 (s, 2H).

Step 3:

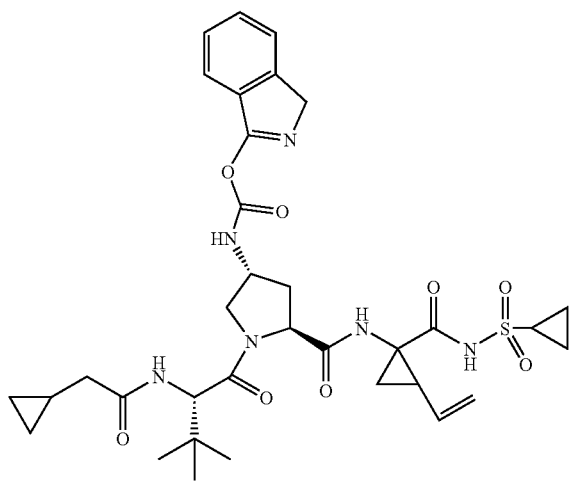

Compound 52

To a solution of carbonic acid 3H-isoindol-1-yl ester 4-nitro-phenyl ester (13.5 mg, 0.0449 mmol) in $CH_2Cl_2$, Compound 8 (25 mg, 0.0374 mmol) and triethylamine (0.011 mL, 0.0823 mmol) were added. The reaction mixture was stirred at room temperature for overnight. Then it was concentrated and the residue was purified by Prep. HPLC column to give white solid as final product as a mixture of diastereoisomers (Compound 52) (11 mg, 42% yield).

(Compound 52, 50177-016): $^1H$ NMR($CD_3OD$, 300 MHz) δ:7.81 (d, J=7.3 Hz, 1H), 7.73 (t, J=7.3 Hz, 1H), 7.65 (d, J=7.3 Hz, 1H), 7.55 (t, J=7.3 Hz, 1H), 5.75 (m, 1H), 5.33(d, J=17.2 Hz, 0.5H), 5.32 (d, J=16.8 Hz, 0.5H), 5.13 (d, J=9.5 Hz, 1H), 4.84 (s, 2H), 4.63 (m, 2H), 4.45 (m, 1H), 4.12(m, 1H), 4.02 (m, 1H), 2.95 (m, 1H), 2.15-2.43 (m, 3H), 2.07 (d, J=7.0 Hz, 2H), 1.89 (dd, J=7.7 Hz, 5.5 Hz, 0.5H), 1.81 (dd, J=7.7 Hz, 5.1 Hz, 0.5H), 1.42 (m, 1H), 0.93-1.35 (m, 13H), 0.87 (m, 1H), 0.43 (m,2H), 0.11 (m,2H).

LC-MS (retention time: 1.547 minutes.), MS m/z 697($MH^+$).

Example 67

Compound 53 was prepared as follows.

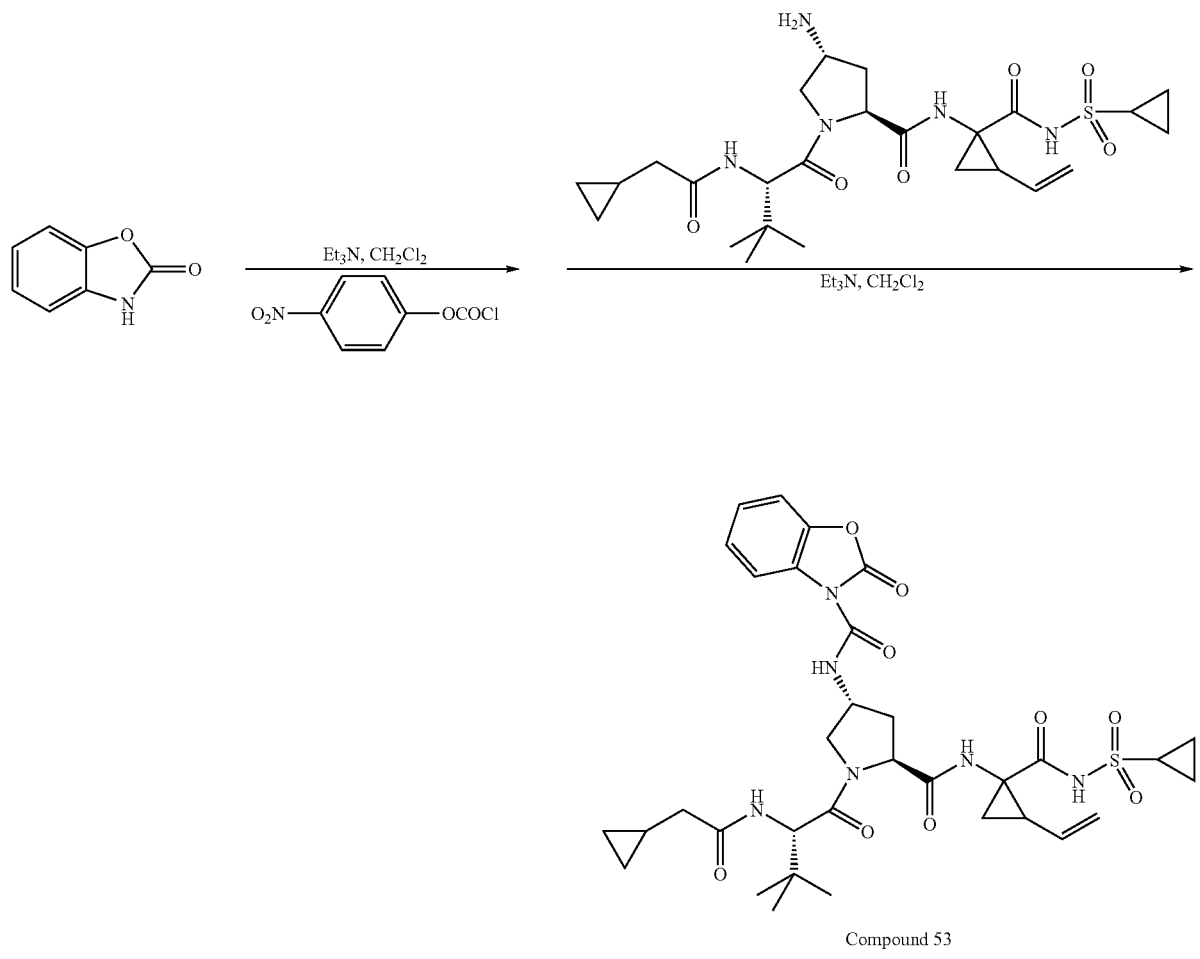

Compound 53

To a solution of 2-benzoxazolinone (10.1 mg, 0.0748 mmol) in CH$_2$Cl$_2$ (5 mL), 4-nitrophenylchloroformate (16.6 mg, 0.0823 mmol) and triethylamine (0.0125 mL, 0.09 mmol) were added. The reaction mixture was stirred at room temperature for 2 hours. Then Compound 8 (25 mg, 0.0374 mmol) and triethylamine (0.011 mL, 0.0785 mmol) were added. The reaction mixture was stirred at room temperature for overnight. Then it was concentrated and the residue was purified by Prep. HPLC column to give white solid as final product as 1:1 diasteoromers (Compound 53) (9.2 mg, 35% yield).

(Compound 53, 50177-010): $^1$H NMR(CD$_3$OD, 500 MHz) δ 8.27 (s, br, 1H), 8.00 (m, 1H), 7.24-7.34 (m, 3H), 5.75 (m, 1H), 5.33(d, J=16.8 Hz, 0.5H), 5.30 (d, J=17.1 Hz, 0.5H), 5.14 (m, 1H), 4.68 (m, 1H), 4.60 (m, 1H), 4.44(m, 1H), 4.14 (m, 1H), 4.06 (m, 1H), 2.95 (m, 1H), 2.37 (m, 1H), 2.20-2.33 (m, 2H), 2.04-2.17 (m, 2H), 1.89 (dd, J=7.6 Hz, 5.5 Hz, 0.5H), 1.81 (dd, J=7.6 Hz, 5.2 Hz, 0.5H), 1.41 (m, 1H), 0.98-1.32 (m, 13H), 0.93 (m, 1H), 0.47(m, 2H), 0.14 (m, 2H).

LC-MS (retention time: 1.573 minutes.), MS m/z 699(MH$^+$).

Example 68

Compound 54 was prepared as follows.

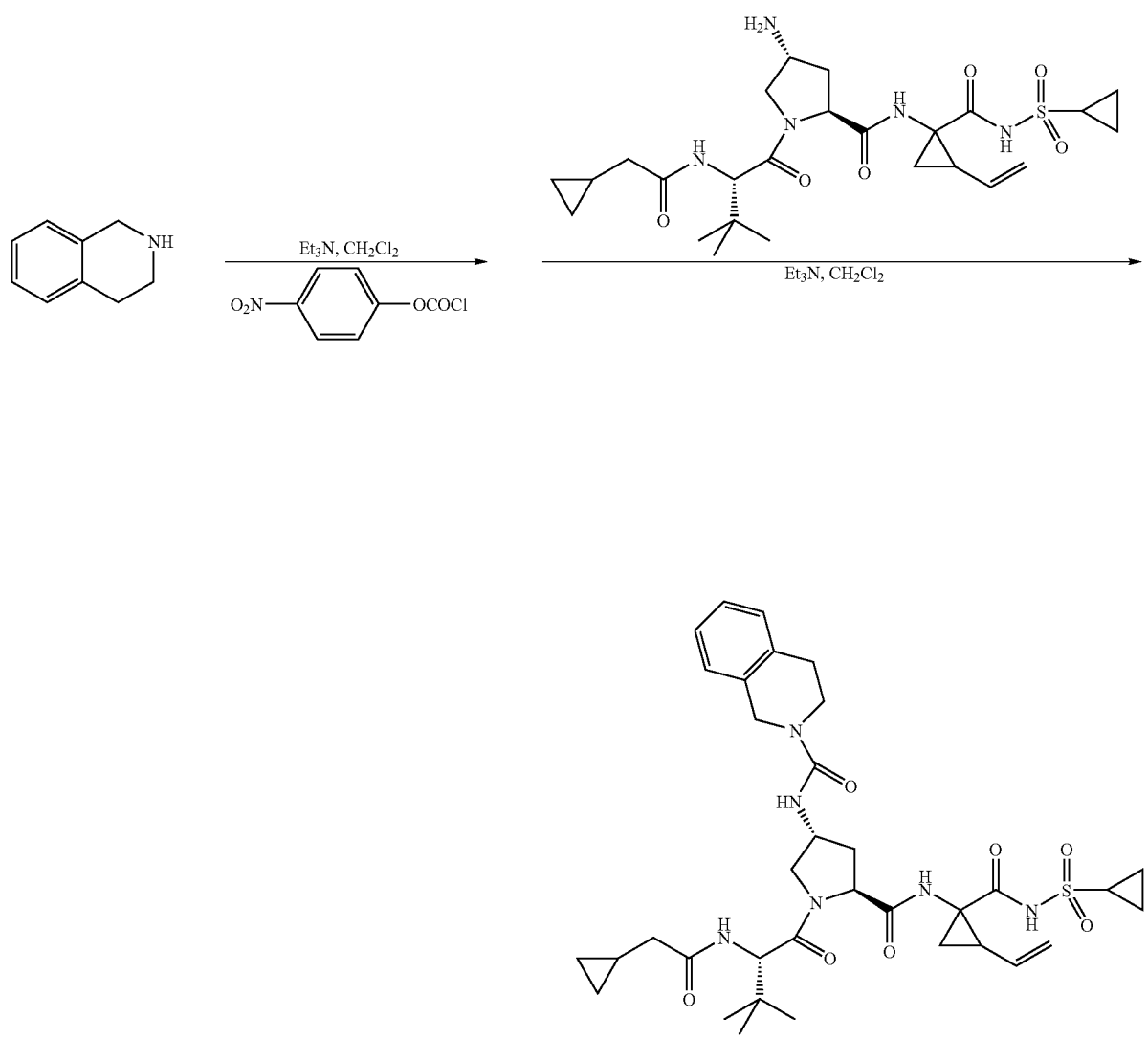

Compound 54

To a solution of 1,2,3,4-tetrahydroisoquinoline (0.005 mL, 0.0412 mmol) in CH$_2$Cl$_2$ (5 mL), 4-nitrophenylchloroformate (9.0 mg, 0.0449 mmol) and triethylamine (0.006 mL, 0.0449 mmol) were added. The reaction mixture was stirred at room temperature for 2 hours. Then Compound 8 (25 mg, 0.0374 mmol) and triethylamine (0.011 mL, 0.0785 mmol) were added. The reaction mixture was stirred at room temperature for overnight. Then it was concentrated and the residue was purified by Prep. HPLC column to give white solid as the final product as 1:1 diasteoromers (Compound 54)(6 mg, 23% yield).

(Compound 54, 50177-030): LC-MS (retention time: 1.803 minutes.), MS m/z 695(M−H$^-$).

Example 69

Compound 55 was prepared as follows.

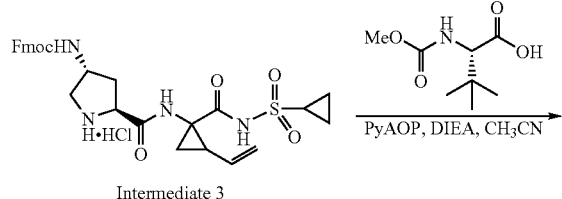
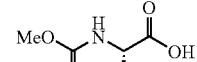

Intermediate 3

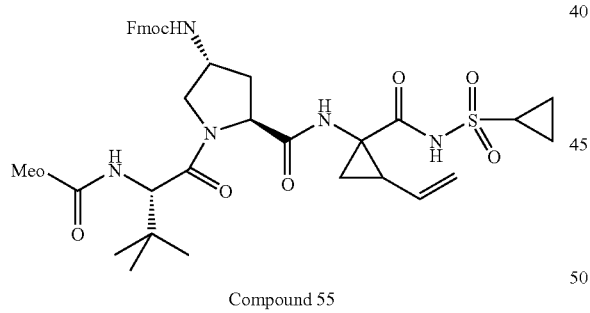

Compound 55

To a solution of intermediate 3 (300 mg, 0.5 mmol) in 5 mL of CH$_3$CN was added 2-Methoxycarbonylamino-3,3-dimethyl-butyric acid (142 mg, 0.75 mmol), DIEA (0.44 mL, 2.5 mmol) and the coupling reagent HOBt (115 mg, 0.75 mmol) and HBTU (284 mg, 0.75 mmol). The solution was stirred at room temperature overnight. It was then washed with water and extracted twice with ethyl acetate. The combined organic layers were washed with brine, dried over MgSO$_4$, filtered, and concentrated to give a yellow oil. It was purified by Prep. HPLC to yield a yellowish solid as the product (Compound 55) (300 mg, 82% yield).

(Compound 55, 50177-095): $^1$H NMR(CD$_3$OD, 500 MHz) δ: 7.79 (d, J=7.63 Hz, 2H), 7.64 (m, 2H), 7.39 (m, 2H), 7.30 (m, 2H), 5.73 (m, 1H), 5.31 (m, 1H), 5.13 (m, 1H), 4.44 (m, 1H), 4.19-4.37 (m, br, 4H), 3.84-3.94(m, br, 2H), 3.58(s, 3H), 2.92 (m, 1H), 2.21 (m, 2H), 2.08 (m, 1H), 1.87 (dd, J=7.94, 5.80 Hz, 0.5H), 1.79 (dd, J=7.93, 5.19 Hz, 0.5H), 1.37 (m, 1H), 0.97-1.31 (m, 14H).

LC-MS (retention time: 1.963 minutes.), MS m/z 778 (MH$^+$).

Example 70

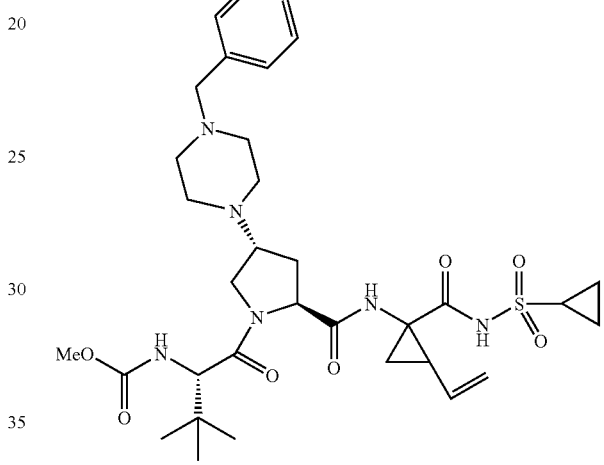

Compound 56

Example 71

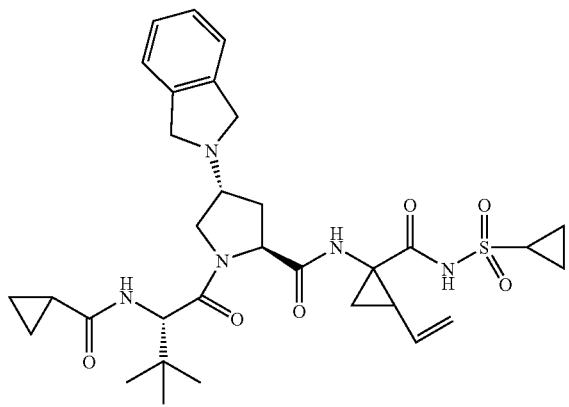

Compound 57

Example 72

Example 72: Preparation of Compound 58.

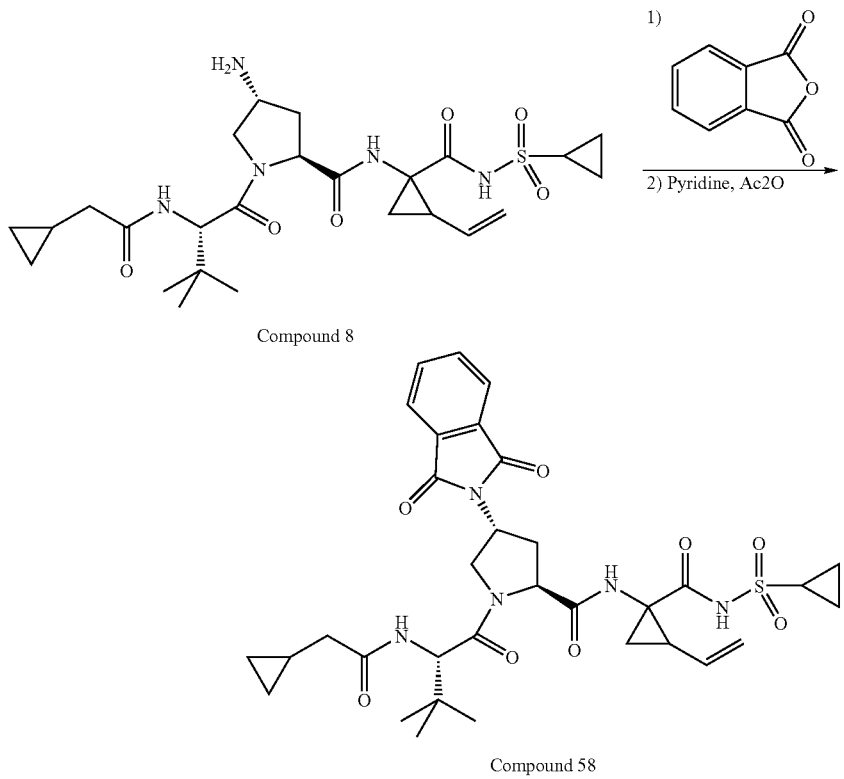

Compound 8

Compound 58

To a suspension of Compound 8 (50 mg, 0.075 mmol) in 1,2-dichloroethane (5 mL), triethylamine (0.026 mL, 0.187 mmol) was added. Then phthalic anhydride (12.2 mg, 0.0824 mmol) was added and the reaction mixture was heated at 50-60° C. for 2 h. It was then evaporated to dryness and then redissolved in pyridine (3 mL). Acetic anhydride (0.071 mL, 0.749 mmol) was added dropwise and the reaction mixture was stirred at rt. for overnight. The volatiles were evaporated and the residue was dissolved in ethyl acetate, washed with water, 1N HCl solution and saturated $NaHCO_3$ solution, and dried (MgSO4). Evaporation of solvent gave a yellowish oil which was purified by Prep. HPLC column to afford a white solid Compound 58 as final 1:1 diastereomers. (12 mg, 24% yield)

Compound 58: $^1$H NMR($CD_3OD$, 300 MHz) δ: diastereomer mixture. LC-MS (Method A, retention time: 1.683 min.), MS m/z 668($MH^+$).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 300 mM Sodium Chloride (NaCl), 0.5% Triton X-100, 1 microgram/milliliter ("µg/mL") lysozyme, 5 mM Magnesium Chloride ($MgCl_2$), 1 µg/mL DnaseI, 5 mM β-Mercaptoethanol (βME), Protease inhibitor—Ethylenediamine Tetraacetic acid (EDTA) free (Roche), homogenized and incubated for 20 minutes (min) at 4° C. The homogenate was sonicated and clarified by ultra-centrifugation at 235000 g for 1 h at 4° C. Imidazole was added to the supernatant to a final concentration of 15 mM and the pH adjusted to 8.0. The crude protein extract was loaded on a Nickel—Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/mL. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat # 22991)(FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound was determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/mL Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 minute before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

All of the compounds tested were found to inhibit the activity of the NS3/4A protease complex with $IC_{50}$'s of 1.2 µM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (PCT Patent Application No. WO 00/09543) with some modifications to the serine protease assays. All enzymes were purchased from Sigma while the substrates were from Bachem.

Each assay included a 2 h enzyme-inhibitor pre-incubation at room temperature followed by addition of substrate and hydrolysis to ~30% conversion as measured on a Spectramax Pro microplate reader. Compound concentrations varied from 100 to 0.4 µM depending on their potency.

The final conditions for each assay were the same as those described in WO 03/099274, page 623.

The percentage of inhibition was calculated using the formula:

$$[1-((UV_{inh}-UV_{blank})/(UV_{ctl}-UV_{blank}))]\times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Assession number:AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Cells were seeded the night before ($1.5\times10^4$ cells/well) in 96-well tissue-culture sterile plates. Compound and no compound controls were prepared in DMEM containing 4% FCS, 1:100 Penicillin/Streptomycin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamar Blue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The HCV protease substrate. The plate was then placed into the Cytofluor 4000 instrument which had been set to 340 nm excitation/490 nm emission, automatic mode for 21 cycles and the plate read in a kinetic mode. $EC_{50}$ determinations were carried out as described for the $IC_{50}$ determinations.

Quantitative HCV RNA Assay

As a secondary assay, $EC_{50}$ determinations from the replicon FRET assay were confirmed in a quantitative RNA assay. Cells were lyzed using the Rneasy kit (Qiagen). Purified total RNA was normalized using RiboGreen (Jones L J, Yue S T, Cheung C Y, Singer V L, Anal. Chem., 265(2):368-74 (1998)) and relative quantitation of HCV RNA expression assessed using the Taqmann procedure (Kolykhalov A A, Mihalik K, Feinstone S M, Rice C M, Journal of Virology 74, 2046-2051 (2000)) and the Platinum Quantitative RT-PCR Thermoscript One-Step kit (Invitrogen cat # 11731-015). Briefly, RNA made to a volume of 5 µl ($\leq$1 ng) was added to a 20 µl Ready-Mix containing the following: 1.25× Thermoscript reaction mix (containing Magnesium Sulfate and 2-deoxynucleoside 5'-triphosphates (dNTPs)), 3 mM dNTPs, 200 nM forward primer (see WO 03/099274), 600 nM reverse primer (see WO 03/099274), 100 nM probe (see WO 03/099274), 1 µM Rox reference dye (Invitrogen cat # 12223-012) and Thermoscript Plus Platinum Taq polymerase mixture. All primers were designed with ABI Prism 7700 software and obtained from Biosearch Technologies, Novato, Calif. Samples containing known concentrations of HCV RNA transcript were run as standards. Using the following cycling protocol (50° C., 30 min; 95° C., 5 min; 40 cycles of 95° C., 15 sec, 60° C., 1 min), HCV RNA expression was quantitated as described in the Perkin Elmer manual using the ABI Prism 7700 Sequence Detector.

Representative compounds of the disclosure were assessed in the HCV enzyme assays, HCV replicon cell assay and/or in several of the outlined specificity assays. For example, Compound 9 was found to have an $IC_{50}$ of 47 nanomolar (nM) against the NS3/4A BMS strain in the enzyme assay. Similar potency values were obtained with the published H77 ($IC_{50}$ of 41 nM) and J4L6S ($IC_{50}$ of 30 nM) strains. The $EC_{50}$ value in the replicon assay was 2250 nM.

In the specificity assays, the same compound was found to have the following activity: HLE>100 µM; PPE>100 µM; Chymotrypsin=65 µM; Cathepsin B>100 µM. These results indicate this family of compounds are highly specific for the NS3 protease and many of these members inhibit HCV replicon replication.

The compounds of the current disclosure were tested and found to have activities in the ranges as follows:

IC50 Activity Ranges (NS3/4A BMS Strain): A is >15 micromolar (μM); B is 0.15-15 μM; C is <0.15 μM EC50 Activity Range (for compounds tested): A is >15 μM; B is 0.15-15 μM; C is <0.15 μM Note that by using the Example number and the Compound number shown in Table 2 below the structures of compounds and their corresponding activities can be found herein.

In accordance with the present disclosure, in one embodiment the compounds have a biological activity (EC$_{50}$) of 100 μM or less, and in another embodiment 1 μM or less.

TABLE 2

| Example Number | Cmpd Number | IC 50 Range | EC50 Range |
|---|---|---|---|
| 15 | 1 | B | |
| 16 | 2 | A | |
| 17 | 3 | C | B |
| 18 | 4 | C | B |
| 19 | 5 | B | B |
| 20 | 6 | C | B |
| 21 | 7 | B | A |
| 22 | 8 | | |
| 23 | 9 | C | B |
| 24 | 10 | B | A |
| 25 | 11 | B | |
| 26 | 12 | B | A |
| 27 | 13 | B | A |
| 28 | 14 | B | A |
| 29 | 15 | B | |
| 30 | 16 | C | A |
| 31 | 17 | C | A |
| 32 | 18 | B | A |
| 33 | 19 | C | A |
| 34 | 20 | C | A |
| 35 | 21 | C | B |
| 36 | 22 | C | A |
| 37 | 23 | B | |
| 38 | 24 | B | A |
| 39 | 25 | C | B |
| 40 | 26 | C | B |
| 41 | 27 | C | B |
| 42 | 28 | C | B |
| 43 | 29 | C | B |
| 44 | 30 | B | A |
| 45 | 31 | C | B |
| 46 | 32 | C | B |
| 47 | 33 | B | A |
| 48 | 34 | C | B |
| 49 | 35 | B | A |
| 50 | 36 | B | |
| 51 | 37 | B | A |
| 52 | 38 | B | A |
| 53 | 39 | C | B |
| 54 | 40 | C | A |
| 55 | 41 | C | A |
| 56 | 42 | B | |
| 57 | 43 | C | A |
| 58 | 44 | B | A |
| 59 | 45 | B | A |
| 60 | 46 | B | |
| 61 | 47 | C | A |
| 62 | 48 | B | A |
| 63 | 49 | B | A |
| 64 | 50 | C | B |
| 65 | 51 | C | B |
| 66 | 52 | C | B |
| 67 | 53 | C | A |
| 68 | 54 | B | |
| 70 | 56 | A | |
| 71 | 57 | B | |
| 72 | 58 | B | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I)

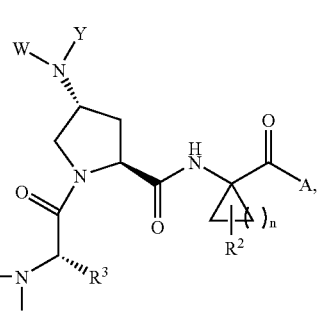

or an enantiomer, diastereoisomer, or a pharmaceutically acceptable salt thereof, wherein A is alkoxy, hydroxy, —N(H)SO$_m$R$^1$, or

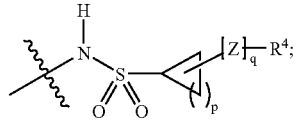

m is 1 or 2;
p is 1, 2 or 3;
q is 0 or 1;
R$^1$ is alkyl, aryl, cycloalkyl, (cycloalkyl)alkyl, heterocyclyl, or —NR$^7$R$^8$;
R$^4$ is alkyl, aryl, arylalkyl, cycloalkenyl, cycloalkyl, halo, heterocyclyl, or trialkylsilyl; wherein the alkyl is optionally substituted with alkenyl, alkoxy, alkynyl, aryl, arylalkyl, aryloxy, cycloalkenyl, cycloalkyl, halo, heterocyclyl, or hydroxy; provided that when R$^4$ is halo or trialkylsilyl then q is 0;
R$^7$ and R$^8$ are each independently alkoxy, alkyl, aryl, arylalkyl, cycloalkyl, (cycloalkyl)alkyl, haloalkyl, heteroaryl, or heteroarylalkyl;
Z is

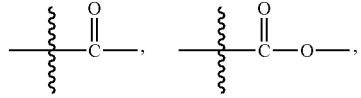

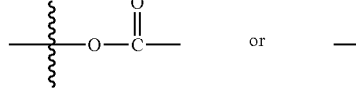

wherein each group is drawn with its left end attached to the cycloalkyl ring and its right end attached to R$^4$ R[11] is hydrogen, alkenyl, alkyl, or aryl, each optionally substituted with alkoxy, amido, amino, cyano, halo, nitro, or phenyl;

n is 1 or 2;

R[2] is hydrogen, alkenyl, alkyl, or cycloalkyl, each optionally substituted with one to three halo groups;

W is hydrogen, alkyl, or alkylcarbonyl; wherein the alkyl can be optionally substituted with alkoxy, amino, carboxy, cyano, or halo;

Y is —C(=O)R[9], —C(O)N(R[10])R[9], —C(NH)N(R[10])R[9], —S(O)$_2$R[9], —S(O)$_2$N(R[10])R[9], arylalkyl, heterocyclyl, or heterocyclylalkyl; provided that when W is hydrogen, Y is other than aryl, arylalkyl, or heterocyclyl;

R[9] and R[10] are independently hydrogen, alkyl, aryl, arylalkyl, heterocyclyl, or heterocyclylalkyl, wherein the alkyl is optionally substituted with alkoxy, amino, cyano, carboxy, or halo; or R[9] and R[10], together with the nitrogen atom to which they are attached, form a three- to seven-membered ring optionally containing zero to two additional heteroatoms selected from nitrogen, oxygen, and sulfur;

R[3] is hydrogen, alkenyl, alkoxy, alkyl, alkylamino, alkylsulfanylalkyl, alkylsulfinylalkyl, alkylsulfonylalkyl, alkynyl, aryl, arylalkyl, carboxyalkyl, cyanoalkyl, cycloalkenyl, cycloalkenylalkyl, cycloalkyl, (cycloalkyl)alkyl, haloalkyl, heterocyclylalkyl, or hydroxyalkyl, wherein the cycloalkyl and cycloalkyl part of the (cycloalkyl)alkyl can be optionally substituted with alkenyl, alkoxy, alkyl, alkylaminoalkyl, or hydroxy;

B is hydrogen, alkyl, aryl, heteroaryl, heterocyclyl, R[5]—(C=O)—, R[5](C=O)—, R[5]—N(R[6])—C(=O)—, R[5]—N(R[6])—C(=S)—, R[5]SO$_2$—, or R[5]—N(R[6])—SO$_2$—;

R[5] is
(i) alkyl optionally substituted with alkoxy, alkylamino, alkylcarbonyl, amido, (lower alkyl)amido, amino, carboxy, dialkylamino, formyl, one to three halo groups, hydroxy, OC(=O)alkyl, phenyl, or phenyloxy, wherein the phenyloxy is optionally substituted with halo or alkoxy;
(ii) cycloalkyl or (cycloalkyl)alkyl, wherein the cycloalkyl and the cycloalkyl part of the (cycloalkyl)alkyl can be optionally substituted with alkoxycarbonyl, alkylamino, amido, (lower alkyl)amido, amino, carboxy, dialkylamino, or hydroxy;
(iii) aryl, arylalkyl, heteroaryl, or heteroarylalkyl, all optionally substituted with alkyl, amido, (lower alkyl)amido, alkylamino, amino, dialkylamino, halo, hydroxy, or nitro;
(iv) heterocyclyl or heterocyclylalkyl, wherein the heterocyclyl and the heterocyclyl part of the heterocyclylalkyl are optionally substituted with alkyl, alkylamino, amido, (lower alkyl)amido, amino, dialkylamino, or hydroxy;
(v) bicyclo(1.1.1)pentane; or
(vi) —C(=O)Oalkyl, alkenyl, or alkynyl; and R[6] is hydrogen or alkyl optionally substituted with one to three halo groups.

2. The compound of claim 1 wherein

A is alkoxy, hydroxy, or —N(H)SO$_m$R[1];

m is 2;

R[1] is alkyl, aryl, cycloalkyl, (cycloalkyl)alkyl, or heterocyclyl;

n is 1;

R[2] is alkenyl, alkyl, or cycloalkyl, each optionally substituted with one to three halo groups;

W is hydrogen or alkyl;

Y is —C(=O)R[9], —C(=S)N(R[10])R[9], —S(O)$_2$R[9];

R[9] and R[10] are independently hydrogen, alkyl, aryl, arylalkyl, heterocyclyl, or heterocyclylalkyl;

R[3] is alkenyl, alkoxy, or alkyl;

B is hydrogen, alkyl, R[5]—(C=O)—, R[5](C=O)—, or R[5]—N(R[6])—C(=O)—;

R[5] is (cycloalkyl)alkyl or alkyl, wherein the alkyl is optionally substituted with alkoxy, alkylamino, amino, carboxy, dialkylamino, one to three halo groups, hydroxy, or phenyl;

and

R[6] is hydrogen.

3. A compound of Formula (II)

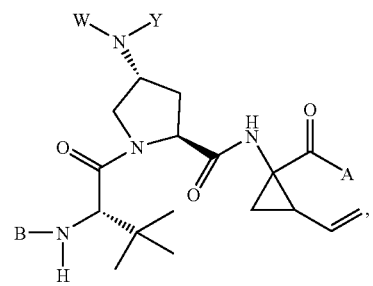

(II)

or an enantiomer, diastereomer, or pharmaceutically acceptable salt theref, wherein A is hydroxy, or —N(H)SO$_2$R[1];

R[1] is cycloalkyl;

W is hydrogen or alkyl;

Y is —C(=O)R[9], —C(=S)N(R[10])R[9], —S(O)$_2$R[9];

R[9] and R[10] are independently hydrogen, aryl, arylalkyl, heterocyclyl, or heterocyclylalkyl;

B is R[5]—(C=O)—, or R[5](C=O)—; and

R[5] is (cycloalkyl)alkyl or alkyl.

4. A compound of Formula (III)

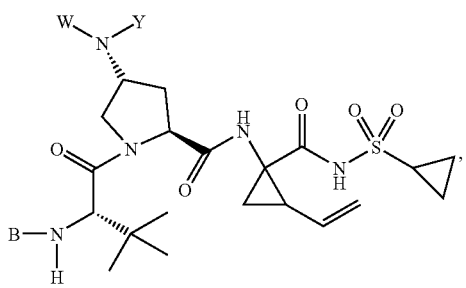

(III)

or an enantiomer, diastereomer, or pharmaceutically acceptable salt theref, wherein W is hydrogen or alkyl;

Y is —C(=O)R[9], —C(=O)OR[9], —C(O)N(R[10])R[9], —S(O)$_2$R[9];

R[9] and R[0] are independently hydrogen, aryl, arylalkyl, heterocyclyl, or heterocyclylalkyl;

B is R[5]—(C=O)—; and

R[5] is (cycloalkyl)alkyl.

5. A compound which is
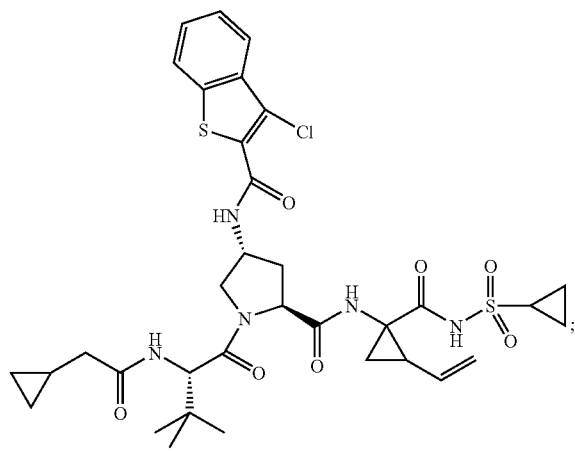
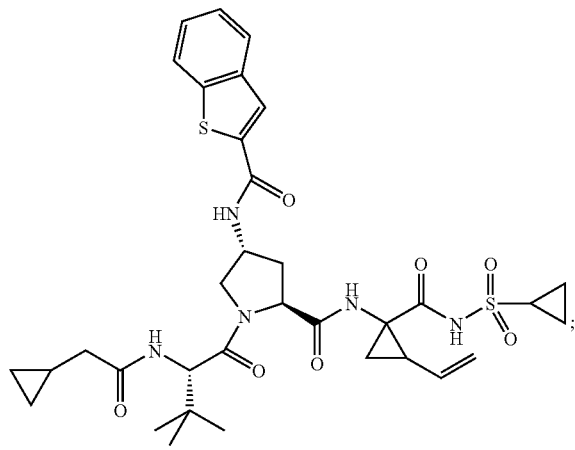
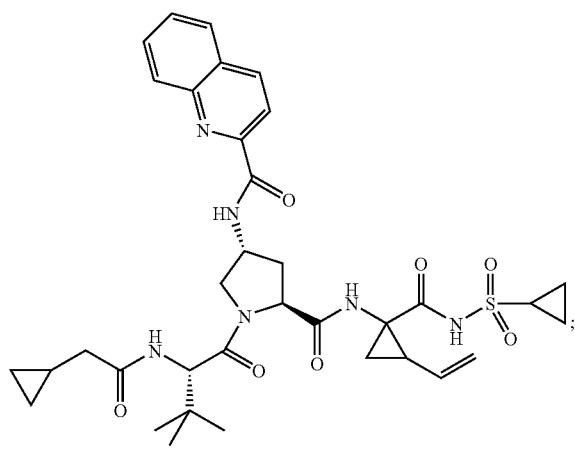
-continued
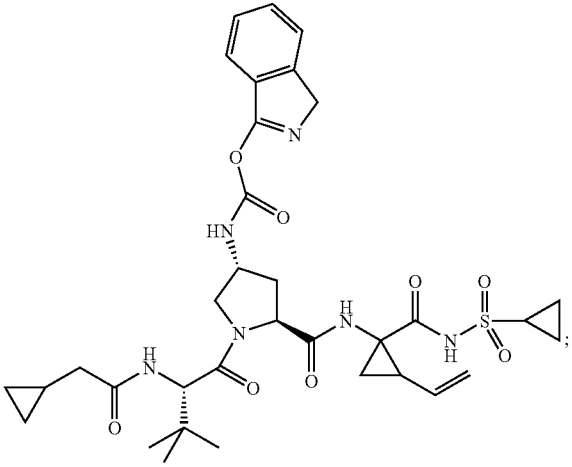
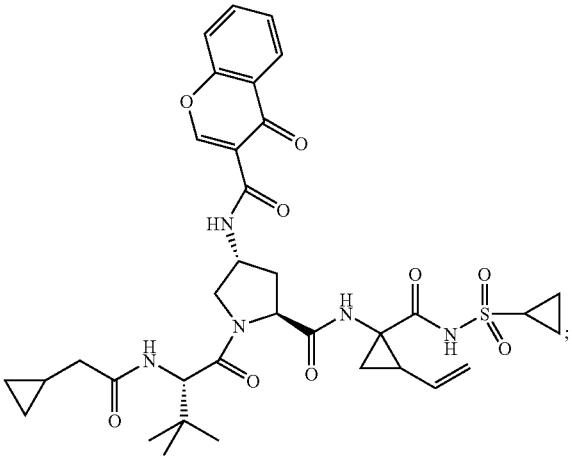
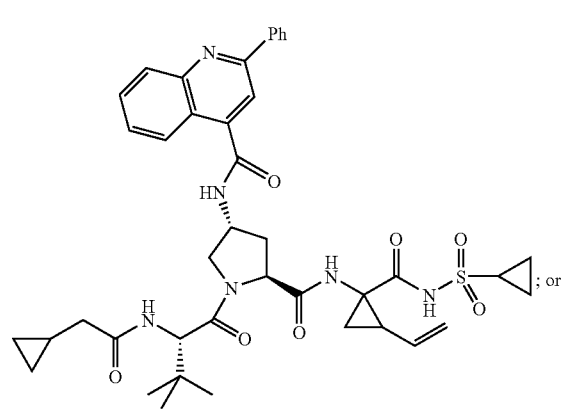

-continued

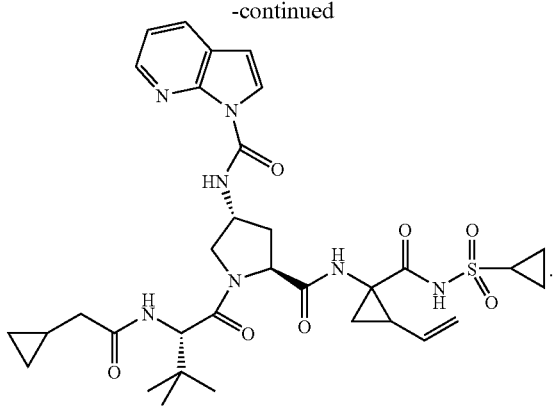

6. A composition comprising the compound of claim 1 and a pharmaceutically acceptable carrier.

7. The composition according to the claim 6 further comprising an interferon and ribavirin.

8. The composition according to claim 6 further comprising a second compound having anti-HCV activity.

9. The composition according to claim 8 wherein the second compound having anti-HCV activity is an interferon.

10. The composition according to claim 9 wherein the interferon is selected from interferon alpha 2B, pegylated interferon alpha, consensus interferon, interferon alpha 2A, and lymphoblastiod interferon tau.

11. The composition according to claim 8 wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

12. The composition according to claim 8 wherein the second compound having anti-HCV activity is a small molecule compound.

13. The composition according to claim 8 wherein the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

14. A method of inhibiting the function of HCV serine protease comprising contacting the HCV serine protease with the compound of claim 1.

15. A method of treating an HCV infection in a patient, comprising administering to the patient a therapeutically effective amount of the compound of claim 1.

16. The method of claim 15 wherein the compound is effective to inhibit the function of the HCV serine protease.

17. The method of claim 15 further comprising administering a second compound having anti-HCV activity prior to, after, or simultaneously with the compound of claim 1.

18. The method of claim 17 wherein the second compound having anti-HCV activity is an interferon.

19. The method of claim 18 wherein the interferon is selected from interferon alpha 2B, pegylated interferon alpha, consensus interferon, interferon alpha 2A, and lymphoblastiod interferon tau.

20. The method of claim 17 wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

21. The method of claim 17 wherein the second compound having anti-HCV activity is a small molecule.

22. The method of claim 17 wherein the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

23. The method of claim 17 wherein the second compound having anti-HCV activity is effective to inhibit the function of target in the HCV life cycle other than the HCV serine protease.

* * * * *

UNITED STATES PATENT AND TRADEMARK OFFICE
CERTIFICATE OF CORRECTION

| | |
|---|---|
| PATENT NO. | : 7,601,686 B2 |
| APPLICATION NO. | : 11/481536 |
| DATED | : October 13, 2009 |
| INVENTOR(S) | : Piyasena Hewawasam et al. |

It is certified that error appears in the above-identified patent and that said Letters Patent is hereby corrected as shown below:

Column 7, lines 49 and 50, change "lymphoblastiod" to -- lymphoblastoid --.

Column 7, line 59, change "Imiqimod" to -- Imiquimod --.

Column 8, line 36, change "lymphoblastiod" to -- lymphoblastoid --.

Column 8, line 49, change "Imiqimod" to -- Imiquimod --.

Claim 1:

Column 154, line 67, after "$R^4$", insert -- ; --.

Column 155, lines 14 and 15, after "aryl,", delete "arylalkyl,".

Claim 2:

Column 156, line 1, change "—$C(=S)N(R^{10})R^9$" to -- —$C(O)N(R^{10})R^9$ --.

Column 156, lines 2 and 3, after "aryl,", delete "arylalkyl,".

Column 156, line 6, change "$R^5(C=O)$—" to -- $R^5O(C=O)$— --.

Claim 3:

Column 156, line 32, change "theref" to -- thereof --.

Column 156, line 37, change "—$C(=S)N(R^{10})R^9$" to -- —$C(O)N(R^{10})R^9$ --.

Column 156, line 38, after "aryl,", delete "arylalkyl,".

Claim 4:

Column 156, line 59, change "theref" to -- thereof --.

Column 156, line 63, change "$R^0$" to -- $R^{10}$ --.

Signed and Sealed this
Twenty-fifth Day of October, 2011

David J. Kappos
*Director of the United States Patent and Trademark Office*

Claim 10:

Column 159, line 30, change "lymphoblastiod" to -- lymphoblastoid --.

Claim 11:

Column 159, line 35, change "Imiqimod" to -- Imiquimod --.

Claim 19:

Column 160, lines 21 and 22, change "lymphoblastiod" to -- lymphoblastoid --.

Claim 20:

Column 159, line 27, change "Imiqimod" to -- Imiquimod --.